(12) United States Patent
Anderson et al.

(10) Patent No.: US 11,957,586 B2
(45) Date of Patent: Apr. 16, 2024

(54) EPICARDIAL VALVE REPAIR SYSTEM

(71) Applicants: Evan Anderson, Woodside, CA (US); John MacMahon, Exeter, NH (US); Jeremy Boyette, Menlo Park, CA (US); Christopher Pell, San Francisco, CA (US); Michael Stewart, Sunnyvale, CA (US); Mark Juravic, Los Altos, CA (US); Mitre Medical Corp., Morgan Hill, CA (US)

(72) Inventors: Evan Anderson, Woodside, CA (US); John MacMahon, Exeter, NH (US); Jeremy Boyette, Menlo Park, CA (US); Christopher Pell, San Francisco, CA (US); Michael Stewart, Sunnyvale, CA (US); Mark Juravic, Los Altos, CA (US)

(73) Assignee: Mitre Medical Corp., Morgan Hill, CA (US)

( * ) Notice: Subject to any disclaimer, the term of this patent is extended or adjusted under 35 U.S.C. 154(b) by 840 days.

(21) Appl. No.: 16/964,975

(22) PCT Filed: Jan. 25, 2019

(86) PCT No.: PCT/US2019/015300
§ 371 (c)(1),
(2) Date: Jul. 25, 2020

(87) PCT Pub. No.: WO2019/148046
PCT Pub. Date: Aug. 1, 2019

(65) Prior Publication Data
US 2021/0045878 A1 Feb. 18, 2021

Related U.S. Application Data

(60) Provisional application No. 62/622,827, filed on Jan. 27, 2018, provisional application No. 62/622,831, (Continued)

(51) Int. Cl.
*A61F 2/24* (2006.01)
*A61B 17/068* (2006.01)
(Continued)

(52) U.S. Cl.
CPC .......... *A61F 2/2481* (2013.01); *A61B 17/068* (2013.01); *A61B 17/10* (2013.01);
(Continued)

(58) Field of Classification Search
CPC .... A61F 2/2481; A61F 2/2442; A61F 2/2451; A61F 2/2466; A61B 17/068; A61B 17/10; A61B 17/2812; A61B 2017/00407
See application file for complete search history.

(56) References Cited

U.S. PATENT DOCUMENTS

| 4,042,979 A | 8/1977 | Angell |
| 6,908,482 B2 | 6/2005 | McCarthy et al. |

(Continued)

FOREIGN PATENT DOCUMENTS

| WO | 2004043265 | 5/2004 |
| WO | 2019148046 | 8/2019 |

OTHER PUBLICATIONS

Fattouch et al., "Mitral valve therapy still surgical?", Eur. Heart Journal Supplements (2015) 17 (Supplement A), A43-A48.
(Continued)

*Primary Examiner* — Julian W Woo
(74) *Attorney, Agent, or Firm* — Law Office of Alan W. Cannon

(57) ABSTRACT

Devices, systems and methods for altering functioning of a tissue/organ by application of force thereto. In one preferred
(Continued)

embodiment, a device for reducing or preventing regurgitation of blood through a valve of a heart is provided. A device may include a main body having a segment adapted to apply force to a surface of tissue/organ and a member that applies counterforce to the force applied by the segment. Kits are provided in which devices having varying lengths and widths can be selected for the best fit for a particular location of treatment. A width sizing instrument may be provided. A length sizing instrument may be provided. A separate sleeve and/or pad may be provided which may be first anchored to the tissue/organ before fixing the device thereto.

29 Claims, 52 Drawing Sheets

Related U.S. Application Data filed on Jan. 27, 2018, provisional application No. 62/622,830, filed on Jan. 27, 2018.

(51) Int. Cl.
| | |
|---|---|
| *A61B 17/10* | (2006.01) |
| *A61B 90/00* | (2016.01) |
| *A61B 17/00* | (2006.01) |
| *A61B 17/064* | (2006.01) |
| *A61B 17/28* | (2006.01) |

(52) U.S. Cl.
CPC ............ *A61B 90/06* (2016.02); *A61F 2/2442* (2013.01); *A61F 2/2451* (2013.01); *A61F 2/246* (2013.01); *A61F 2/2466* (2013.01); *A61F 2/2478* (2013.01); *A61B 2017/00243* (2013.01); *A61B 2017/00398* (2013.01); *A61B 2017/00407* (2013.01); *A61B 2017/00473* (2013.01); *A61B 2017/00738* (2013.01); *A61B 2017/00858* (2013.01); *A61B 17/064* (2013.01); *A61B 2017/0649* (2013.01); *A61B 17/2812* (2013.01); *A61B 2090/061* (2016.02); *A61B 2090/0801* (2016.02); *A61F 2002/2484* (2013.01); *A61F 2210/0033* (2013.01); *A61F 2210/0076* (2013.01); *A61F 2220/0016* (2013.01); *A61F 2220/0025* (2013.01); *A61F 2220/0033* (2013.01); *A61F 2220/0083* (2013.01); *A61F 2230/0013* (2013.01); *A61F 2230/0023* (2013.01); *A61F 2250/0002* (2013.01); *A61F 2250/0003* (2013.01); *A61F 2250/0004* (2013.01); *A61F 2250/0007* (2013.01); *A61F 2250/001* (2013.01); *A61F 2250/0029* (2013.01); *A61F 2250/0036* (2013.01); *A61F 2250/006* (2013.01); *A61F 2250/0064* (2013.01)

(56) References Cited

U.S. PATENT DOCUMENTS

| | | | |
|---|---|---|---|
| 7,247,134 B2* | 7/2007 | Vidlund | ............... A61F 2/2481 600/16 |
| 7,591,826 B2 | 9/2009 | Alferness et al. | |
| 7,766,812 B2 | 8/2010 | Schroeder et al. | |
| 8,012,202 B2 | 9/2011 | Alameddine | |
| 8,262,725 B2 | 9/2012 | Subramanian | |
| 8,647,254 B2 | 2/2014 | Callas et al. | |
| 8,956,407 B2 | 2/2015 | Macoviak et al. | |
| 9,566,443 B2 | 2/2017 | De Canniere | |
| 9,615,926 B2 | 4/2017 | Lahinkski et al. | |
| 9,636,223 B2 | 5/2017 | Khalil et al. | |
| 9,724,194 B2 | 8/2017 | Callas et al. | |
| 9,795,481 B2 | 10/2017 | Callas et al. | |
| 10,485,663 B2 | 11/2019 | Callas et al. | |
| 2002/0111533 A1 | 8/2002 | Melvin | |
| 2004/0064014 A1 | 4/2004 | Melvin et al. | |
| 2005/0119735 A1 | 6/2005 | Spence et al. | |
| 2007/0066863 A1 | 3/2007 | Rafiee et al. | |
| 2010/0004504 A1 | 1/2010 | Callas et al. | |
| 2010/0010538 A1 | 1/2010 | Juravic et al. | |
| 2012/0323314 A1 | 12/2012 | Callas et al. | |
| 2013/0030522 A1 | 1/2013 | Rowe et al. | |
| 2014/0172084 A1 | 6/2014 | Callas et al. | |
| 2015/0366556 A1 | 12/2015 | Khairkhahan et al. | |
| 2018/0008412 A1 | 1/2018 | Callas et al. | |
| 2019/0231527 A1 | 8/2019 | MacMahon et al. | |
| 2019/0231528 A1 | 8/2019 | MacMahon et al. | |
| 2020/0015972 A1 | 1/2020 | Callas et al. | |

OTHER PUBLICATIONS

Grayburn et al., "Proportionate and Disproportionate Functional Mitral Regurgitation", JACC Cardiovascular Imaging, 2018, pp. 1-10.

International Search Report re PCT/US2019/015300, dated May 31, 2019.

Kashem et al., "CardiClasp: A New Passive Device to Re-Shape Cardiac Enlargement", ASAIO Journal, 2002, pp. 1-7.

Tibayan et al., "Does septal-lateral annular cinching work for chronic ischemic mitral regurgitation?", J. Throac. and Card. Surg., Mar. 2004, pp. 654-663.

\* cited by examiner

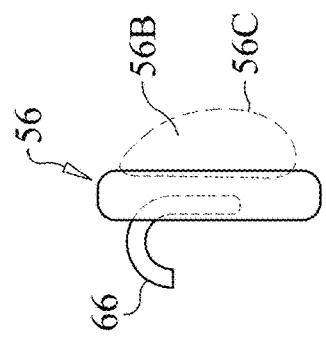
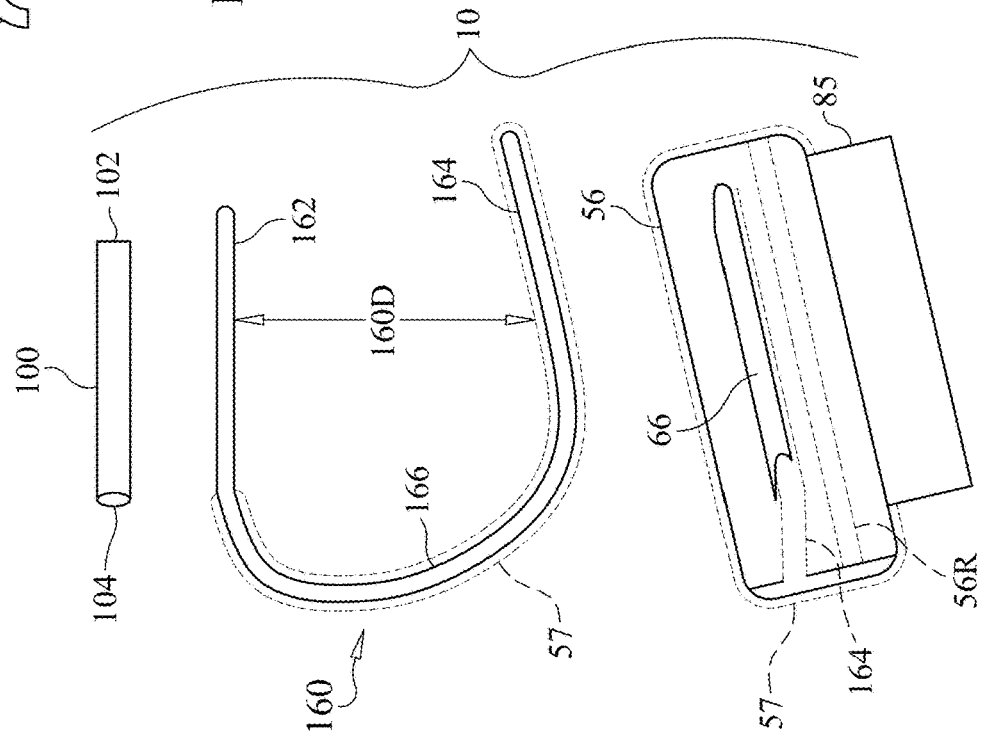
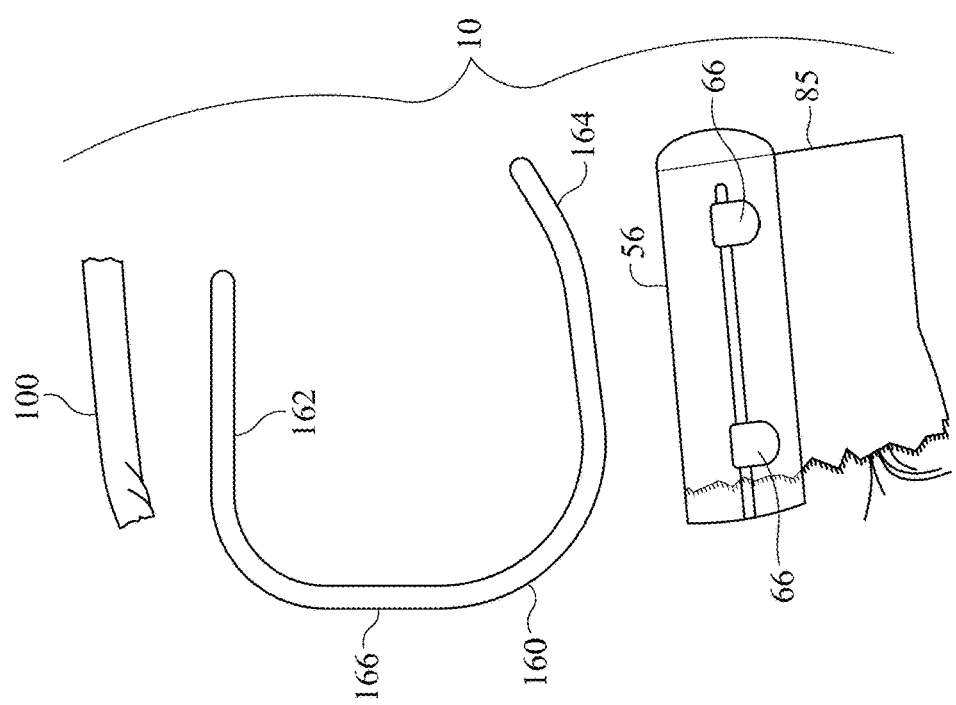

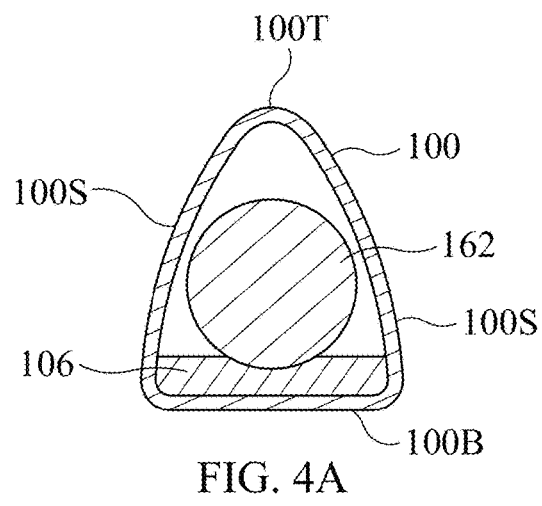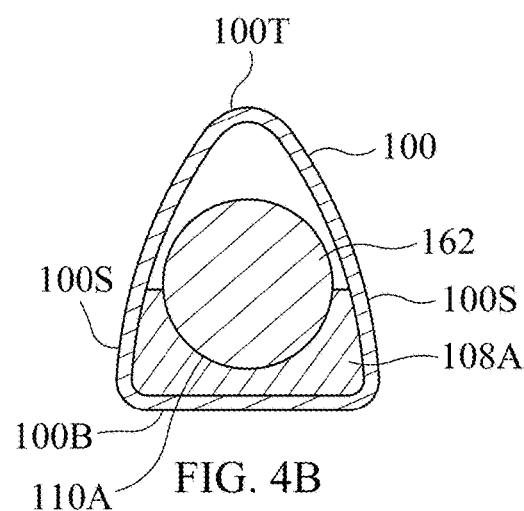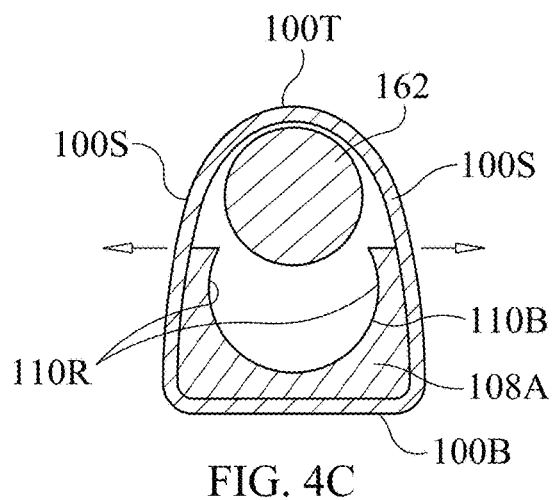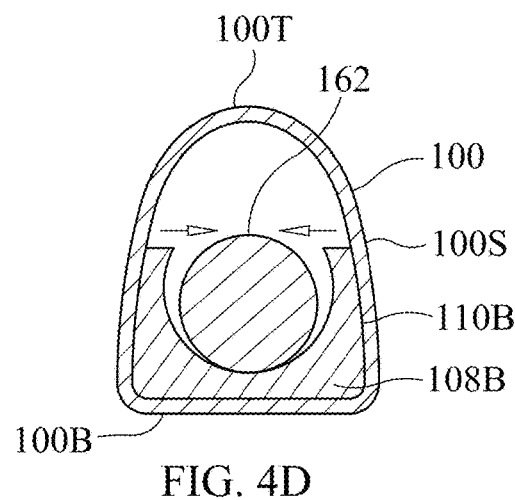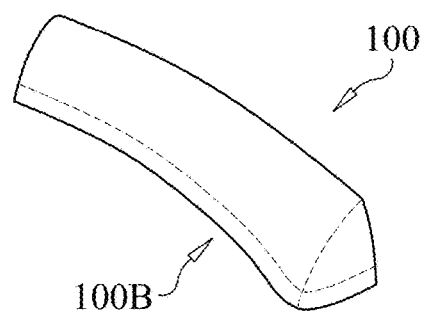

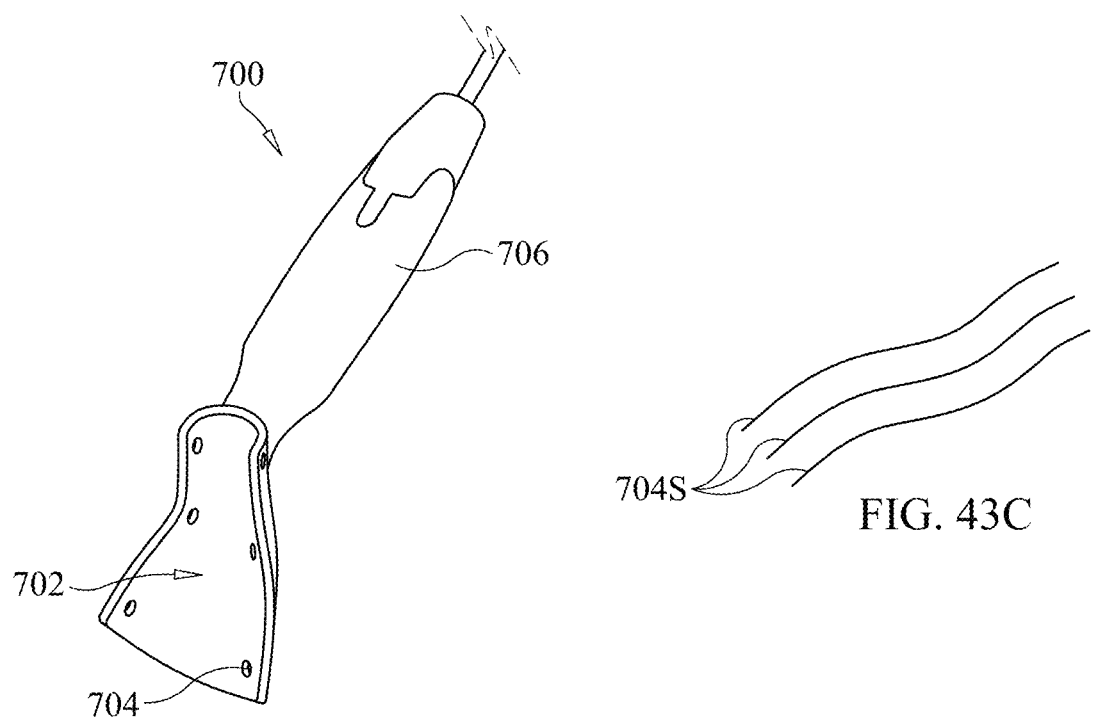
FIG. 43B
FIG. 43C
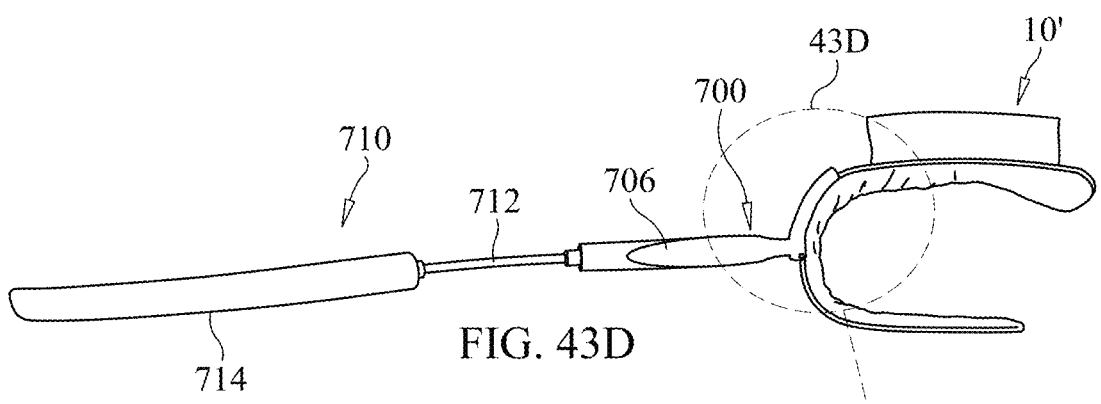
FIG. 43D
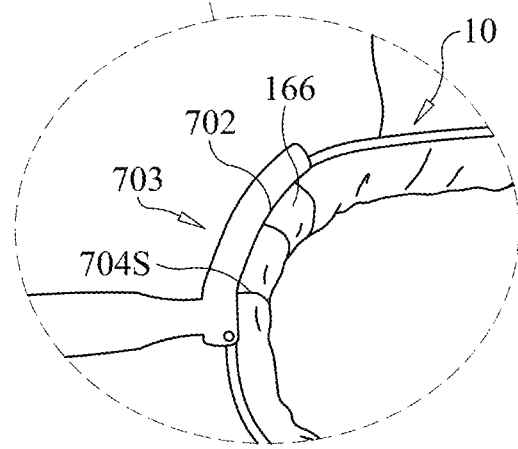
FIG. 43E

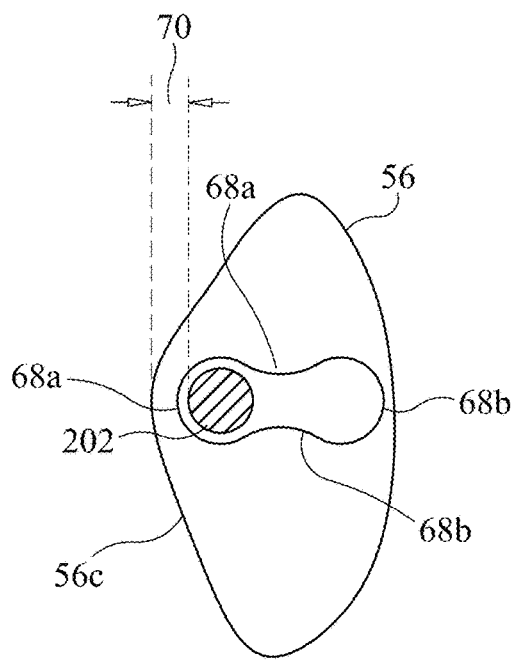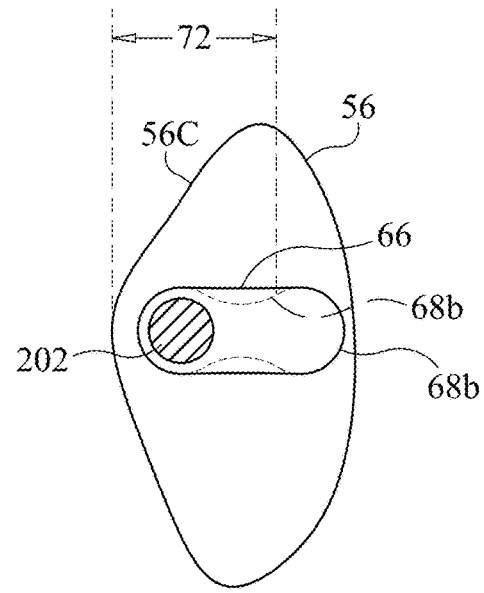
FIG. 45E  FIG. 45F
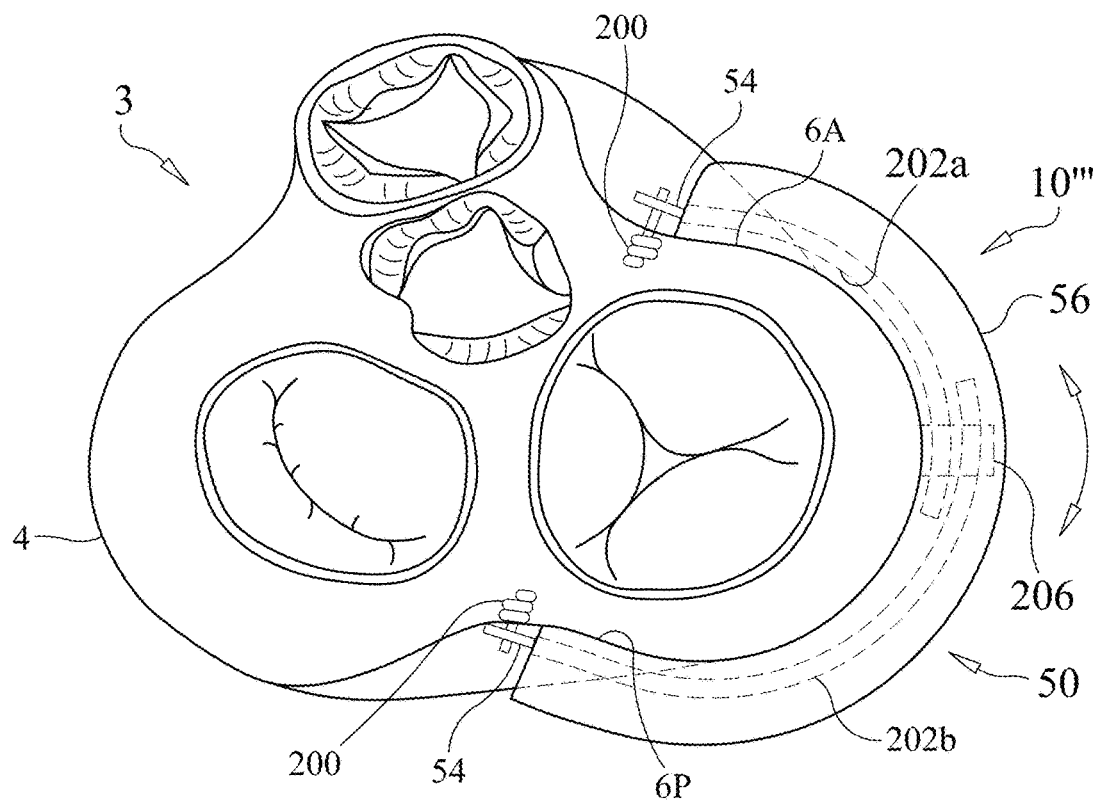
FIG. 46

EPICARDIAL VALVE REPAIR SYSTEM

CROSS-REFERENCE

This application is a 371 of International Application No. PCT/US2019/015300, filed Jan. 25, 2019, which claims the benefit of U.S. Provisional Application Nos. 62/622,827; 62/622,830; and 62/622,831, each of which were filed on Jan. 27, 2018. Each of PCT/US2019/015300; U.S. Provisional Application No. 62/622,827; U.S. Provisional Application No. 62/622,830; and U.S. Provisional Application No. 62/622,831 are hereby incorporated herein, in their entireties, by reference thereto and to which applications we claim priority under 35 USC § 119.

INCORPORATION BY REFERENCE

All publications and patent applications mentioned in this specification are herein incorporated by reference to the same extent as if each individual publication or patent application was specifically and individually indicated to be incorporated by reference. This specification specifically incorporates US Patent Application Publication Nos. 2010/0004504 A1 and 2012/0323314 A1 herein, in their entireties, by reference thereto. Also specifically incorporated by reference in their entireties, are U.S. Provisional Application Ser. Nos. 62/622,830; 62/622,831 and 62/622,830, as noted above. Further, this specification specifically incorporates the following applications in their entireties: U.S. application Ser. No. 16/258,525 titled "Atraumatic Adjustment or Replacement of a Device for Treating Valve Regurgitation", filed Jan. 25, 2019; International (PCT) Application No. PCT/US2019/015302, titled "Self Adjusting Device", filed Jan. 25, 2019; and U.S. application Ser. No. 16/258,519, titled "Manually Adjustable Device", filed Jan. 25, 2019.

FIELD OF THE INVENTION

This invention applies to the field of cardiac surgery and more specifically, to treatment of a heart valve.

BACKGROUND OF THE INVENTION

Mitral Valve Regurgitation (MR) affects 2% of the population worldwide, but less than 20% of people in developed countries who are diagnosed each year with MR undergo a cardiac surgery procedure. Left untreated, MR is a risk factor and can lead to heart failure. In addition, it is estimated that 20% of patients with heart failure and 15% of post-myocardial infarction patients have at least moderate MR.

Functional MR occurs due to enlargement of the left ventricle (LV) of the heart with a corresponding increase in the diameter of the Mitral Valve annulus. This diameter increase prevents the two leaflets of the Mitral Valve from co-apting and prevents them from properly preventing blood flow from the left ventricle to the left atrium during contraction of the heart. Recent randomized trials in heart failure and the MitraClip device found that reducing mitral regurgitation arrested the dilation of the left ventricle, common in the heart failure cycle. The cycle of heart failure includes negative feedback between the left ventricle dilation and the MR. The heart's natural response to MR is to dilate the LV and dilating the LV makes more MR. Hence these two components cycle the patient into worse cardiac output. Grayburn et al., "Proportionate and Disproportionate Functional Mitral Regurgitation" JACC: Cardiovascular Imaging, 2018 cited that longevity and improved quality of life paralleled left ventricular volume reductions. It is reasonable that designs that reduce both mitral regurgitation and cardiac volume may have profound clinical benefits.

SUMMARY OF THE INVENTION

At least one aspect of the present invention relates to a system for mitral valve repair that decreases the diameter of the heart in the septal lateral direction and/or anterior posterior direction and brings the leaflets back to a normal anatomical position. In at least one embodiment, the system does this by gently squeezing from the surface of the heart using a multi-step delivery method which may optionally use a multi-step delivery system to implant an epicardial device. The implant is decreasing both the mitral valve diameter and the volume of the left ventricle interrupting the heart failure cycle at two points.

The epicardial device in some embodiments is delivered into the body in parts and may be done using a minimally-invasive, closed chest procedure. In at least one embodiment a sleeve is secured in the transverse sinus using a fixator driving tool. In at least one embodiment, a posterior pad is secured to the ventricular wall below the level of the atrioventricular groove. Subsequently, a main body wire-form or clip is slid into the sleeve and then pulled down to engage with an engagement feature of the posterior pad. Optionally, a flap of the posterior pad may be pulled over the wire-form.

In one aspect of the present invention, an epicardial device for placement on the epicardial surface of a heart in order to reshape the annulus of the mitral valve of the heart is provided, the mitral valve lying in a plane between the left atrium and the left ventricle of the heart, the anatomy of the heart includes an aorta, a pulmonary trunk, a superior vena cava, a transverse sinus, a coronary sinus and an atrioventricular groove, the epicardial device comprising: an anterior member configured to be secured in the transverse sinus; a posterior member configured to be secured epicardially to a wall of the left ventricle; and a main body configured to be connected to the anterior member and the posterior member subsequent to at least one of securement of the anterior member in the transverse sinus and securement of the posterior member to the wall of the left ventricle.

In at least one embodiment, the main body is configured to be connected to the anterior member and the posterior member subsequent to both of the securement of the anterior member in the transverse sinus and the securement of the posterior member to the wall of the left ventricle.

In another aspect of the present invention, an epicardial device for placement on an epicardial surface of a heart in order to reshape an annulus of a valve of the heart is provided that includes: a main body having a generally U-shape or C-shape when viewed from a top or bottom view, the main body including a lateral segment interconnecting an anterior segment and a posterior segment; a sleeve provided separately of said main body, the sleeve being configured and dimensioned to receive the anterior segment; and a pad provided separately of the main body, the pad comprising an engagement feature configured to engage with the posterior segment; wherein the main body is non-flexible relative to forces applied thereto by the heart.

In at least one embodiment, the sleeve is configured to be anchored to the epicardial surface of the heart prior to receiving the anterior segment.

In at least one embodiment, the pad is configured to be anchored to the epicardial surface of the heart prior to engagement with the posterior segment.

In at least one embodiment, the epicardial device is configured for reshaping an annulus of a mitral valve of the heart.

In at least one embodiment, the epicardial device is configured for reshaping dimensions of a left ventricle of the heart.

In at least one embodiment, the epicardial device is configured for reshaping an annulus of a tricuspid valve of the heart.

In at least one embodiment, the epicardial device is configured for reshaping dimensions of a right ventricle of the heart.

In at least one embodiment, the valve is the mitral valve, the mitral valve lying in a plane between the left atrium and the left ventricle of the heart, the anatomy of the heart includes an aorta, a pulmonary trunk, a superior vena cava, a transverse sinus, and an atrioventricular groove; wherein the anterior segment is configured and dimensioned to at least partially occupy the transverse sinus epicardially and end at a location short of overlying the right atrium of the heart; and wherein the pad is configured and dimensioned to contact the heart on or below a plane in which the mitral valve is located, and below a position of the anterior segment.

In at least one embodiment, the main body maintains the U-shape or C-shape after completion of placement of the epicardial device on the heart.

In at least one embodiment, the engagement feature comprises a hook extending from a surface of the pad.

In at least one embodiment, a reinforcing member is provided within the pad.

In at least one embodiment, a contact surface of the pad is configured to expand after anchoring the pad to target tissue, to increase force applied to the target tissue and by association remodel either or both the mitral valve or left ventricle.

In at least one embodiment, the surface is opposite a contact surface of the pad, wherein the contact surface of the pad is configured to contact the epicardial surface of the heart when the pad is anchored to the epicardial surface.

In at least one embodiment, the engagement feature comprises a receptacle formed in the pad and configured to receive at least a portion of the posterior segment.

In at least one embodiment, the device further includes a locator clip in the receptacle, the locator clip configured to capture the posterior segment so that a predefined length of the posterior segment is received in the receptacle.

In at least one embodiment, the pad is molded, the device further comprising a flap extending inferiorly of the pad, wherein the flap is not molded and is configured to be anchored to the epicardial surface by passing one or more fixators through the flap.

In at least one embodiment, the flap comprises multiple flaps extending inferiorly of the pad.

In at least one embodiment, a contact surface of the pad has a roughness exceeding a roughness of a surface of the pad opposite the contact surface.

In at least one embodiment, the sleeve is a tubular structure having a flat surface extending along a length thereof, the flat surface configured to engage the heart at a bottom of a transverse sinus.

In at least one embodiment, the sleeve comprises a tubular structure and further comprises a sleeve pad within the tubular structure, the sleeve pad being placed to reside between a bottom surface of the sleeve and the anterior segment.

In at least one embodiment, the sleeve pad is a contoured pad having a receptacle formed therein, wherein the receptacle generally conforms to a shape of the anterior segment to be received therein.

In at least one embodiment, the sleeve is tubular and comprises a first surface configured to be oriented as a bottom surface when anchoring the sleeve to the epicardial surface of the heart, and a second surface opposite the first surface, wherein the second surface comprises at least one opening configured to permit a fixator to be passed therethrough to enable the fixator to be driven through the first surface to anchor the sleeve. The fixator can deliver a fixing force in either mechanical, chemical or photoreactive form. An embodiment of the chemical of photoreactive form may be adhesive or light activated bonds, for example, UV adhesives.

In at least one embodiment, the sleeve comprises a tubular structure, the device further comprising a flap extending radially or tangentially outwardly from the sleeve and also extending along a length of the sleeve.

In at least one embodiment, the main body is provided in multi-part segments, wherein the segments are configured to be assembled in the body of a patient to form the non-flexible main body.

In at least one embodiment, the segments are connectable via mechanical connectors.

In at least one embodiment the segments are connectable via magnetic connectors.

In another aspect of the present invention, an epicardial device for reducing or preventing regurgitation of blood through a tricuspid valve of a heart is provided, wherein the device includes: a main body having a segment adapted to apply force to an epicardial surface of the heart; a member that applies counterforce to the force applied by the segment; and an adjuster that is operable to change the force applied by the segment, wherein the adjuster can be operated before or after anchoring of the device to the epicardial surface.

In at least one embodiment, the adjuster is manually operable.

In at least one embodiment, the adjuster is remotely operable.

In at least one embodiment, the segment comprises a rigid structural rib contained within a pad; wherein the pad comprises a contact surface configured to apply force to the epicardial surface; wherein the adjuster comprises a channel having stops formed therein; wherein a first set of the stops maintains the rib at a first predetermined distance from the contact surface; and wherein a second set of the stops maintains the rib at a second predetermined distance from the contact surface, the second predetermined distance being unequal to the first predetermined distance.

In at least one embodiment, the main body is configured and dimensioned to surround greater than 50% of an annulus of the tricuspid valve.

In at least one embodiment, the device is operable to change a location of at least a portion of the rib from being held by the first set of stops to a location where the at least a portion of the rib is held by the second set of stops, by manually pushing against the rib, at least a portion of a rib from being held by a first set of stops to a location where the at least a portion of the rib is held by a second set of stops, via application of pressure to the body at locations apposite the first set of stops, while applying counter-pressure to the contact surface at locations that are not apposite to the first set of stops.

In at least one embodiment, the main body comprises two segments comprising rods that extend through opposite end portions of the main body and are joined together by an actuator configured so that the segments are drivable in opposite directions to one another, to increase or decrease a distance between ends of the main body.

In at least one embodiment, the actuator is motorized. In another aspect of the present invention, a method of epicardial treatment of valve regurgitation associated with a valve of a heart of a patient includes: establishing at least one opening in the patient to provide access to the heart; anchoring a sleeve to an epicardial surface of the heart at a location adjacent a first side of the valve; anchoring a pad to an epicardial surface of the heart at a location adjacent a second side of the valve, wherein the second side is opposite the first side; inserting an anterior segment of a clip into the sleeve; rotating the clip about a longitudinal axis of the anterior segment; and engaging a posterior segment of the clip with the pad.

In at least one embodiment, the posterior segment is captured by at least one hook extending from the pad.

In at least one embodiment, the posterior segment is received in a receptacle in the pad.

In at least one embodiment, the valve is the mitral valve; wherein the sleeve is inserted into the transverse sinus of the heart and anchored thereto; and wherein the pad is anchored to a posterior surface of the left ventricle.

In at least one embodiment, the pad is located so that the posterior segment is positioned on or inferior to the atrioventricular groove or in the oblique sinus of the heart.

In at least one embodiment, the method further includes, after the establishing at least one opening and prior to the anchoring: applying an epicardial force on a location of the heart, while visualizing regurgitation through the valve via visualization apparatus; varying at least one of the location or the amount of epicardial force applied to identify a target position where valve regurgitation and left ventricle dimensions are reduced and/or MR eliminated; and marking the target position on the heart or registered markings in the visualization apparatus; wherein the anchoring the pad comprises anchoring the pad in the target position.

In at least one embodiment, the valve is the mitral valve, the sleeve is anchored in the transverse sinus of the heart and the pad is anchored to a posterior wall of the left ventricle of the heart.

In at least one embodiment, the method further includes: measuring a distance between opposing epicardial surfaces of the heart where one of the opposing epicardial surfaces is measured at the target position; and selecting the clip so that the clip is configured with opposed force applying segments separated by a distance that approximates the measured distance between the opposing epicardial surfaces, when the clip device is installed on the heart by inserting the anterior segment and engaging the posterior segment.

In at least one embodiment, the method further includes: measuring a length of a transverse sinus of the heart to be occupied by the anterior segment; and selecting the clip having the anterior segment with an anterior segment length less than or equal to the length of the transverse sinus measured.

In another aspect of the present invention, a fixator driver is provided that includes:

an elongate handle; an end effector located at a distal end of the elongate handle, wherein the end effector includes: a head; a shaft rotationally mounted relative to the head; a spool configured to drive the shaft as the spool rotates; and a slot in the shaft configured to receive a proximal end portion of a fixator; and a drive line configured to be wrapped around the spool and still have sufficient length to extend to a proximal end of the elongate handle; wherein exertion of a pulling force on the drive line while holding the elongate handle stationary drives the spool and the shaft in rotation.

In at least one embodiment, the shaft has a longitudinal axis that is transverse to a longitudinal axis of the elongate handle.

In at least one embodiment, the shaft has a longitudinal axis that is normal to a longitudinal axis of the elongate handle.

In at least one embodiment, the head and the shaft are configured and dimensioned to drive a fixator through a sleeve and into a transverse sinus of the heart.

In at least one embodiment, the fixator is a surgical tack.

In at least one embodiment, the fixator driver further includes a guide arm extending alongside the elongate handle, the guide arm configured to be received in a sleeve during anchoring of the sleeve using the fixator driver.

In at least one embodiment, a distal end portion of the guide arm is offset from a proximal end portion of the guide arm in a direction along a longitudinal axis of the guide arm.

In another aspect of the present invention, a fixator driver is provided that includes:

an elongate handle; and an end effector located at a distal end of the elongate handle configured to drive a fixator in a direction transverse to a longitudinal axis of the elongate handle; wherein the end effector and at least a distal portion of the elongate handle are configured and dimensioned to be inserted into a transverse sinus of the heart.

In at least one embodiment, the fixator driver further includes a rack and pinion drive mechanism operably connected to a shaft, wherein the shaft is rotatable to drive the fixator.

In at least one embodiment, the end effector includes a drive mechanism comprising a constant force spring and a one-way ratchet mechanism.

In at least one embodiment, the end effector includes a biased cam biased against a stop by a spring.

In at least one embodiment, the end effector includes a drive mechanism comprising a pair of bevel gears.

In at least one embodiment, the end effector comprises a reloadable fixator cartridge.

In at least one embodiment, the end effector comprises an adhesive and if appropriate the activation source for the adhesive.

In another aspect of the present invention, a kit configured for epicardial treatment of a heart valve of a heart is provided, the kit including: a first device having a first anterior segment, a first posterior segment and a first lateral segment joining the first anterior segment and the first posterior segment, wherein the first posterior segment is configured to apply force to a posterior wall of the heart, wherein the first anterior segment is configured to apply force to a wall of the heart in opposition to the force applied by the first posterior segment, and wherein a force applying surface of the first posterior segment is separated from a force applying surface of the first anterior segment by a first width; a second device having an second anterior segment, a second posterior segment and a second lateral segment joining the second anterior segment and the second posterior segment, wherein the second posterior segment is configured to apply force to the posterior wall of the heart, wherein the second anterior segment is configured to apply force to a wall of the heart in opposition to the force applied by the second posterior segment, wherein a force applying surface of the second posterior segment is separated from a force applying surface of the second anterior segment by a second width, and wherein the second width is unequal to the first width; and a width sizing instrument configured to apply force to the posterior wall of the heart, while visualizing blood through the heart valve to ascertain an optimum amount of the force and resultant deformation of the posterior wall to be applied to reduce or eliminate valve regurgitation; wherein one of the plurality of devices that most closely matches a width measurement determined by measuring a distance between the epicardial surface of the posterior wall where the width sizing instrument contacts and applies force thereto during the visualization at a time when the optimum amount of force and resultant deformation occurs, and the epicardial surface of an anterior wall opposite where the width sizing instrument contacts the posterior wall, is selected as a best fit device to be used.

In at least one embodiment, the first anterior segment has a first length, the second anterior segment has a second length and the first and second lengths are unequal.

In at least one embodiment, the first anterior segment has a first length, the second anterior segment has a second length and the first and second lengths are equal.

In at least one embodiment, the kit further includes a pad, wherein the pad has a length, width and contact surface curvature similar to or the same as an instrument length, instrument width and instrument contact surface curvature, respectively, of the width sizing instrument.

In at least one embodiment, a first pad envelopes at least a portion of the first posterior segment and a second pad envelopes at least a portion of the second posterior segment.

In at least one embodiment, the pad comprises an engagement feature; and the pad is configured to be anchored to the posterior surface of the heart prior to attaching the first posterior segment or the second posterior segment thereto.

In at least one embodiment, the kit further includes a length sizing instrument configured to measure a length of a site in which the first or second anterior segment is to be implanted.

In at least one embodiment, the site is the transverse sinus of the heart.

In at least one embodiment, the first anterior segment is provided separately from the first lateral segment and is connectable to the first lateral segment, wherein the first width is defined when the first anterior segment is connected to the first lateral segment.

In at least one embodiment, the second anterior segment is provided separately from the second lateral segment, wherein the second anterior segment is connectable to the second lateral segment or the first lateral segment, wherein the first anterior segment is connectable to the second lateral segment or the first lateral segment, wherein the first anterior segment has a first length, the second anterior segment has a second length and the first length is different from the second length.

In at least one embodiment, the kit further includes a third device having a third anterior segment, a third posterior segment and a third lateral segment joining the third anterior segment and the third posterior segment, wherein a force application surface of the third posterior segment is separated from a force application surface of the third anterior segment by the first width; and a fourth device having a fourth anterior segment, a fourth posterior segment and a fourth lateral segment joining the fourth anterior segment and the fourth posterior segment, wherein a force application surface of the fourth posterior segment is separated from a force application surface of the fourth anterior segment by the second width; and a selection is made from one of the first and third devices having an anterior segment length which most closely matches but does not exceed a measurement of the length sizing instrument when the first width best matches a width measured by the width sizing instrument; and a selection is made from one of the second and fourth devices having an anterior segment length which most closely matches but does not exceed the measurement of the length sizing instrument when the second width best matches the width measured by the width sizing instrument.

In at least one embodiment, the kit further includes a sleeve configured to be anchored to the anterior surface of the heart prior to insertion of the first anterior segment or the second anterior segment therein.

In at least one embodiment, the kit includes a set of sleeves having varying lengths for receiving the anterior segments of the devices and corresponding to varying lengths of the anterior segments of the devices.

In at least one embodiment, the width sizing instrument is configured to mark a surface of the heart.

In at least one embodiment, the kit further includes an extension handle that is connectable to said width sizing instrument.

In at least one embodiment, the extension handle comprises a t-bar extending transversely to a longitudinal axis of a main shaft of the extension handle.

In at least one embodiment, the kit further includes an implant insertion cradle having a concave implant interface surface configured to match a convex curvature of a portion of any one of the devices.

In at least one embodiment, the implant insertion cradle comprises a plurality of attachment features on or through the implant interface surface to facilitate releasable attachment of the implant insertion cradle to any one of the devices.

In another aspect of the present invention, a method of treatment of mitral valve regurgitation is provided, the mitral valve lying in a plane between a left atrium and a left ventricle of the heart, the anatomy of the heart including an aorta, a pulmonary trunk, a superior vena cava, a transverse sinus, a coronary sinus and an atrioventricular groove, wherein the method includes: applying force epicardially to a posterior wall of the left ventricle while visualizing blood flow through the mitral valve; altering at least one of a location where the force is applied and an amount of force that is applied until a location and amount of force are found that optimize the function of the mitral valve, wherein the optimization of the function results in elimination or minimization of mitral valve regurgitation; measuring a distance between epicardial posterior and anterior surfaces of the heart where the force is applied and where an anterior segment of a device is to be contacted to the anterior surface as a counterforce to the force applied posteriorly; selecting a device having an anterior segment, posterior segment and lateral segment joining the anterior and posterior segments, wherein the device selected has a device width measurement between contact surfaces of the anterior segment and posterior segment that most closely matches the measured distance, when selected from a plurality of devices having varying device width measurements; and installing the selected device epicardially so that the anterior segment is inserted into the transverse sinus and the posterior segment contacts the posterior wall of the ventricle in a location where the width measurement of the heart was taken.

In at least one embodiment, the method further includes: inserting a length sizing instrument into the transverse sinus to measure an unobstructed length of the transverse sinus that the anterior segment can safely occupy; and measuring an unobstructed length of the transverse sinus; wherein the selecting a device further comprises selecting the device having a longest anterior segment length that does not exceed the measured, unobstructed length of the transverse sinus.

In at least one embodiment, the method further includes: selecting a sleeve having a longest length that does not exceed the unobstructed length of the transverse sinus, from a set of sleeves, or cutting a single sleeve to the unobstructed length; and installing the sleeve into the transverse sinus prior to inserting the anterior segment into the transverse sinus, wherein the anterior segment is then inserted into the sleeve.

In at least one embodiment, the method further includes anchoring the sleeve in the transverse sinus prior to inserting the anterior segment.

In at least one embodiment, the method further includes: anchoring a pad to the posterior wall of the ventricle in a location where the width measurement of the heart was taken, and attaching the posterior segment to the pad.

In at least one embodiment, the posterior member further comprises a flap extending from the pad, the flap being configured to be positioned over a portion of the main body to secure the main body to the posterior member.

In at least one embodiment, the main body comprises a wire-form.

In at least one embodiment, the main body is made of titanium. Alternatively, the main body may comprise stainless steel, carbon fiber, polycarbonate, DELRIN and/or other equivalent, biocompatible materials having sufficient rigidity to perform as described herein.

In at least one embodiment, the main body is curved and comprises an anterior segment, an intermediate segment and a posterior segment; wherein the anterior segment is configured and dimensioned to at least partially occupy the transverse sinus epicardially and end at a location short of overlying the right atrium; the intermediate segment interconnecting the anterior segment and the posterior segment, the main body being curved so that the anterior segment can be positioned on or above a plane in which the mitral valve is located, while allowing the posterior segment to be positioned on or below the plane in which the mitral valve is located, and below a position of the anterior segment.

In at least one embodiment, rotation of the epicardial device about a longitudinal axis of the anterior segment moves the posterior segment towards or away from the apex of the heart while the anterior segment remains in contact with a base of the transverse sinus, on the epicardial surface of the heart at a location superior of an anterior annulus of the mitral valve.

In at least one embodiment, the main body is non-flexible, having a permanent configuration which may not be readily bent to an ad hoc configuration without the use of a bending tool.

In at least one embodiment, the main body is sufficiently rigid so that it is not deformable by forces less than or equal to maximum force capable of being applied thereto by the heart.

In at least one embodiment, the main body comprises at least two segments that can be delivered separately through a small incision to the heart from a location outside of a body in which the heart is located, and that can be assembled by connecting the segments together within the body.

In at least one embodiment, the segments are magnetically connectable.

In at least one embodiment, the main body is provided with at least one detent mechanism for connecting the segments together.

In at least one embodiment, the pad comprises a hooked member configured to capture a posterior portion of the main body.

In at least one embodiment, the sleeve comprises a flap configured to overlay an anterior portion of the main body.

In at least one embodiment, the pad is at least partially covered with fabric.

In at least one embodiment, the fabric extends out to a flap.

In at least one embodiment, the pad is curved.

In at least one embodiment, a posterior portion of the main body is curved and the pad is curved to follow a curvature of the posterior portion of the main body.

In at least one embodiment, the sleeve has an internal contour that matches an outer contour of an anterior portion of the main body.

In at least one embodiment, the pad has an internal contour that matches an outer contour of a posterior portion of the main body.

In at least one embodiment, the posterior member is made of a non-rigid material.

In at least one embodiment, the anterior member can be cut to length.

In at least one embodiment, the anterior member can be penetrated with a tack or needle and suture.

In at least one embodiment, the posterior member can be penetrated with a tack or needle and suture.

In at least one embodiment, the device further comprises at least one tack inserted through the anterior member.

In at least one embodiment, the device further comprises at least one tack inserted through the posterior member.

In at least one embodiment, the device further comprises at least one tack configured and dimensioned to be inserted through the anterior member to anchor the anterior member to the heart in the transverse sinus.

In at least one embodiment, the device further comprises at least one tack configured and dimensioned to be inserted through the posterior member to anchor the posterior member to the wall of the left ventricle.

In at least one embodiment, the device further comprises at least one tack having a length of at least 5 mm in length.

In at least one embodiment, the at least one tack has a diameter of about 2 mm.

In at least one embodiment, the sleeve is configured to provide a counterforce sufficient to push the helical tack into tissue of the heart when a force is applied to the tack.

In at least one embodiment, at least one of the anterior member and the posterior member comprises at least one guide configured to guide a tack therethrough such that the tack anchors the anterior member or posterior member to the heart.

In at least one embodiment, at least one of the anterior member and the posterior member has at least one tack incorporated therein.

In at least one embodiment, at least one of the anterior member and the posterior member comprises a roughened surface configured to increase friction with the surface of the heart.

In at least one embodiment, the roughened surface is provided on an external layer, the external layer having a greater roughness than a roughness of the anterior member or posterior member that the external layer overlies.

In another aspect of the present invention, a method of reshaping an annulus of a mitral valve of a heart is provided, the mitral valve lying in a plane between a left atrium and a left ventricle of the heart, the anatomy of the heart including an aorta, a pulmonary trunk, a superior vena cava, a transverse sinus, a coronary sinus and an atrioventricular groove, the method comprising: securing a first member in the transverse sinus; installing a main body by connecting the main body to the first member; and anchoring a posterior portion of the main body to a wall of the left ventricle.

In at least one embodiment, the anchoring a posterior portion comprises anchoring a pad fixed to the main body to the wall of the left ventricle.

In at least one embodiment, the anchoring a posterior portion comprises:

anchoring a second member to the wall of the left ventricle; and connecting a posterior portion of the main body to the second member.

In at least one embodiment, the anchoring a second member is performed prior to the connecting the main body to the first member.

In at least one embodiment, the first member is secured epicardially and the posterior portion is anchored epicardially.

In at least one embodiment, the method is performed minimally invasively, in a closed-chest procedure wherein first member and main body are delivered through a small opening, port or puncture.

In at least one embodiment, the first member comprises a sleeve.

In at least one embodiment, the second member comprises a pad.

In at least one embodiment, the second member comprises a flap, and the connecting a posterior portion of the main body to the second member includes positioning the flap over the posterior portion.

In at least one embodiment, the main body comprises a wire-form.

In at least one embodiment, the main body is curved and comprises an anterior segment, an intermediate or lateral segment and a posterior segment; wherein the anterior segment is configured and dimensioned to at least partially occupy the transverse sinus epicardially and end at a location short of overlying the right atrium; the intermediate segment interconnecting the anterior segment and the posterior segment, the posterior segment including the posterior portion, the main body being curved so that the anterior segment can be positioned on or above a plane in which the mitral valve is located, while allowing the posterior segment to be positioned on or below the plane in which the mitral valve is located, and below a position of the anterior segment.

In at least one embodiment, the main body comprises at least two segments that can be delivered separately through a small incision to the heart from a location outside of a body in which the heart is located, wherein the method includes separately delivering the at least two segments; and joining the at least two segments at a location inside the body.

In at least one embodiment, the joining comprises magnetically joining the at least two segments.

In at least one embodiment, the joining comprises mechanically joining the at least two segments.

In at least one embodiment, the mechanically joining is carried out using at least one detent mechanism provided in the at least two segments.

In at least one embodiment, the second member is provided with a hook and the connecting comprises maneuvering the posterior portion to capture the posterior portion with the hook.

In at least one embodiment, the securing a first member in the transverse sinus comprises tacking the first member to heart tissue in the transverse sinus.

In at least one embodiment, the securing a first member in the transverse sinus comprises suturing the first member to heart tissue in the transverse sinus.

In at least one embodiment, the anchoring a second member to the wall of the left ventricle comprises tacking the second member to the wall.

In at least one embodiment, the anchoring a second member to the wall of the left ventricle comprises suturing the second member to the wall.

In at least one embodiment, the method further comprises selecting the body from a plurality of variously sized main bodies, for a proper fit, prior to the connecting the main body to the first member.

In another aspect of the present invention, an instrument for implanting an epicardial device on a heart for reshaping an annulus of a mitral valve of the heart is provided, the mitral valve lying in a plane between a left atrium and a left ventricle of the heart, the anatomy of the heart including an aorta, a pulmonary trunk, a superior vena cava, a transverse sinus, a coronary sinus and an atrioventricular groove, the instrument comprising: an elongate shaft having proximal and distal end portions; an engagement head located on the distal end portion configured and dimensioned to engage a tack; and a driving mechanism operable from the proximal end portion to drive the engagement head and the tack to anchor the tack in heart tissue.

In at least one embodiment, the engagement head rotates in a plane perpendicular to a longitudinal axis of the elongate shaft.

In at least one embodiment, the engagement head rotates in a plane parallel to a longitudinal axis of the elongate shaft.

In at least one embodiment, the driving mechanism comprises a pulley engaged with the engagement head, and a driving line operable to rotate the pulley.

In at least one embodiment, the instrument is operable by a single hand to drive a tack into tissue of the heart.

In at least one embodiment, the driving mechanism comprises a pulley system.

In at least one embodiment, the driving mechanism comprises a rack and pinion gear.

In at least one embodiment, the driving mechanism comprises an Archimedes screw with a plunger.

In at least one embodiment, the driving mechanism comprises a ratchet mechanism.

In at least one embodiment, the driving mechanism comprises a constant force spring and a dampener mechanism.

In at least one embodiment, the driving mechanism comprises a ratchet mechanism for winding.

In at least one embodiment, the constant force spring rotates the engagement head to drive the tack upon reaching a predetermined force normal to the tack, thereby ensuring proper delivery of the tack into tissue of the heart.

In at least one embodiment, the driving mechanism comprises a spring loaded shaft with a biasing cam mechanism.

In at least one embodiment, the driving mechanism comprises a right angle gear.

In at least one embodiment, the driving mechanism comprises a ratchet mechanism.

In another aspect of the present invention, a system for implanting an epicardial device on a heart for reshaping an annulus of a mitral valve of the heart is provided, the mitral valve lying in a plane between a left atrium and a left ventricle of the heart, the anatomy of the heart including an aorta, a pulmonary trunk, a superior vena cava, a transverse sinus, a coronary sinus and an atrioventricular groove, the system comprising: an epicardial device for placement on the epicardial surface of a heart in order to reshape the annulus of the mitral valve of the heart; at least one anchor; and an instrument for the at least one anchor into tissue of the heart for anchoring the epicardial device epicardially to tissue of the heart;

In at least one embodiment, the epicardial device comprises an anterior member configured to be secured in the transverse sinus; a posterior member configured to be secured epicardially to a wall of the left ventricle; and a main body configured to be connected to the anterior member and the posterior member subsequent to at least one of securement of the anterior member in the transverse sinus and securement of the posterior member to the wall of the left ventricle.

In at least one embodiment, the system further comprises a guide to facilitate delivery of the anterior member to an epicardial surface of the heart.

In at least one embodiment, the guide facilitates delivery of the anterior member to the transverse sinus.

In at least one embodiment, a guide facilitates delivery of the posterior member to an epicardial surface of the heart.

In at least one embodiment, the guide facilitates delivery of the posterior member to an epicardial surface of a wall of the left ventricle.

In at least one embodiment, the system further comprises a mechanism for retaining a flap on the anterior member or the posterior member.

In another aspect of the present invention, a kit configured for epicardial treatment of a heart valve of a heart is provided that includes: a plurality of devices including a first device having a first anterior segment, a first posterior segment and a first lateral segment joining the first anterior segment and the first posterior segment, wherein the first posterior segment is configured to contact and apply force to a posterior wall of the heart, wherein the first anterior segment is configured to contact an anterior wall of the heart, and wherein a contact surface of the first posterior segment is separated from a contact surface of the first anterior segment by a first width; a second device having an second anterior segment, a second posterior segment and a second lateral segment joining the second anterior segment and the second posterior segment, wherein the second posterior segment is configured to contact and apply force to the posterior wall of the heart, wherein the second anterior segment is configured to contact the anterior wall of the heart, wherein a contact surface of the second posterior segment is separated from a contact surface of the second anterior segment by a second width, and wherein the second width is unequal to the first width; and a width sizing instrument configured to apply force to the posterior wall of the heart, while visualizing blood through the heart valve to ascertain an optimum amount of the force and resultant deformation of the posterior wall to be applied to reduce or eliminate valve regurgitation; wherein one of the plurality of devices that most closely matches a width measurement determined from the visualization is selected as best fit device to be used.

In at least one embodiment, the first anterior segment has a first length, the second anterior segment has a second length and the first and second lengths are unequal.

In at least one embodiment, the first anterior segment has a first length, the second anterior segment has a second length and the first and second lengths are equal.

In at least one embodiment, the kit further includes a length sizing instrument configured to measure a length of a site in which the anterior segment is to be implanted.

In at least one embodiment, the site is the transverse sinus of the heart.

In at least one embodiment, the kit further includes: a third device having a third anterior segment, a third posterior segment and a third lateral segment joining the third anterior segment and the third posterior segment, wherein a contact surface of the third posterior segment is separated from a contact surface of the third anterior segment by the first width; and a fourth device having a fourth anterior segment, a fourth posterior segment and a fourth lateral segment joining the fourth anterior segment and the fourth posterior segment, wherein a contact surface of the fourth posterior segment is separated from a contact surface of the fourth anterior segment by the second width; and a selection is made from one of the first and third devices having an anterior segment length which most closely matches but does not exceed a measurement of the length sizing instrument when the first width best matches a width measured by the width sizing instrument; and a selection is made from one of the second and fourth devices having an anterior segment length which most closely matches but does not exceed the measurement of the length sizing instrument when the second width best matches the width measured by the width sizing instrument.

In at least one embodiment, the kit further includes a sleeve configured to be anchored to the anterior surface of the heart prior to insertion of the first anterior segment or the second anterior segment therein.

In at least one embodiment, the kit further includes a pad configured to be anchored to the posterior surface of the heart prior to attachment of the first posterior segment or the second posterior segment thereto.

In at least one embodiment, the kit further includes a sleeve configured to be anchored to the anterior surface of the heart prior to insertion of the first anterior segment or the second anterior segment therein, wherein the sleeve is configured to be cut to a length measured by the length sizing instrument.

In at least one embodiment, the kit includes a set of sleeves having varying lengths for receiving the anterior segments of the devices and corresponding to varying lengths of the anterior segments of the devices.

In at least one embodiment, the width sizing instrument is configured to mark a surface of the heart.

In at least one embodiment, the mark is applied via a surgical marking liquid.

In at least one embodiment, the mark is formed via application of heat to the posterior surface of the heart.

In another aspect of the present invention, a kit configured for use in epicardial treatment of a heart valve of a heart includes: a plurality of devices each including an anterior segment, a posterior segment and a lateral segment joining the anterior segment and the posterior segment, wherein the posterior segment is configured to contact and apply force to a posterior wall of the heart, wherein the anterior segment is configured to contact an anterior wall of the heart, wherein the anterior segment has an anterior length, and wherein a contact surface of the posterior segment is separated from a contact surface of the anterior segment by a width; wherein the widths of at least two of the devices are equal; wherein widths of at least two of the devices are unequal; and wherein anterior lengths of at least two of the devices are unequal; a width sizing instrument configured to apply force to the posterior wall of the heart, while visualizing blood through the heart valve to ascertain an optimum amount of the force and resultant deformation of the posterior wall to be applied to reduce or eliminate valve regurgitation; and a length sizing instrument configured to measure a length of a site in which the anterior segment is to be implanted; wherein one of the plurality of devices having the width that most closely matches a width measurement determined from the visualization and an anterior length that most closely matches, but does not exceed a length measurement determined using the length sizing instrument is selected as a best fit device to be used.

In at least one embodiment, the kit further includes a sleeve configured to be anchored to the anterior surface of the heart prior to insertion of the anterior segment therein.

In at least one embodiment, the sleeve is configured to be cut to a length measured by the length sizing instrument.

In at least one embodiment, a set of the sleeves is provided having varying lengths for receiving varying lengths of the anterior segment of the devices.

In at least one embodiment, the heart valve is the mitral valve.

In at least one embodiment, the anterior segment is configured to be secured in a transverse sinus of the heart and the posterior segment configured to be secured epicardially to a wall of the left ventricle.

In another aspect of the present invention, a method of treatment of mitral valve regurgitation is provided, the mitral valve lying in a plane between a left atrium and a left ventricle of the heart, the anatomy of the heart including an aorta, a pulmonary trunk, a superior vena cava, a transverse sinus, a coronary sinus and an atrioventricular groove. The method includes: applying force epicardially to a posterior wall of the left ventricle while visualizing blood flow through the mitral valve; altering at least one of a location where the force is applied and an amount of force that is applied until a location and amount of force are found that optimize the function of the mitral valve, wherein the optimization of the function results in elimination or minimization of mitral valve regurgitation; measuring a distance between epicardial posterior and anterior surfaces of the heart where the force is applied and where an anterior segment of a device is to be contacted to the anterior surface as a counterforce to the force applied posteriorly; selecting a device having an anterior segment, posterior segment and lateral segment joining the anterior and posterior segments, wherein the device selected has a device width measurement between contact surfaces of the anterior segment and posterior segment that most closely matches the measured distance, when selected from a plurality of devices having varying device width measurements; and installing the selected device epicardially so that the anterior segment is inserted into the transverse sinus and the posterior segment contacts the posterior wall of the ventricle in a location where the width measurement of the heart was taken.

In at least one embodiment, the method further includes: inserting a length sizing instrument into the transverse sinus until a distal end of the instrument contacts an end of the transverse sinus or an obstruction within the transverse sinus; and measuring an unobstructed length of the transverse sinus; wherein the selecting a device further comprises selecting the device having a longest anterior segment length that does not exceed the unobstructed length of the transverse sinus.

In at least one embodiment, the method further includes: selecting a sleeve having a longest length that does not exceed the unobstructed length of the transverse sinus, from a set of sleeves, or cutting a single sleeve to the unobstructed length; and installing the sleeve into the transverse sinus prior to inserting the anterior segment into the transverse sinus, wherein the anterior segment is then inserted into the sleeve.

In at least one embodiment, the method further includes anchoring the sleeve in the transverse sinus prior to inserting the anterior segment.

In at least one embodiment, the method further includes anchoring a pad to the posterior wall of the ventricle in a location where the width measurement of the heart was taken, and attaching the posterior segment to the pad.

In at least one embodiment, the force is applied epicardially to the posterior wall of the left ventricle with a width sizing instrument.

In at least one embodiment, the method further includes marking the posterior wall of the left ventricle with the width sizing instrument.

In another aspect of the present invention, a minimally invasive method for epicardial implantation of a device for treatment of valve regurgitation is provided, the method including: installing a device port, a camera port and at least one instrument port in the chest of a patient to permit access to a chest cavity of the patient by the device, a camera and instruments; insufflating the chest cavity; positioning the camera though the camera port and into the chest cavity; introducing the device through one of the ports and into the chest cavity using an instrument controlled from outside the chest cavity and port; manipulating the device to partially surround an annulus of a valve by placement of the device on epicardial walls of the heart at locations that partially surround the annulus; anchoring the device to the epicardial walls of the heart; and removing all instruments and camera, removing the ports, and closing the patient.

In at least one embodiment, the method further includes: prior to introducing the device, assessing a width measurement for selecting a device having opposing contact surfaces defining a width that most closely matches the width measurement wherein the assessing comprises: passing a width measuring instrument through the device port; positioning and manipulating the width measuring instrument to apply forces to an epicardial surface of the heart in a plane of the valve to be treated, while visualizing functioning of the valve to assess any regurgitation that may be occurring; repositioning the width measurement instrument and/or varying an amount of force applied by the width measurement instrument while continuing said visualizing; identifying a location where the width measurement instrument is applied to the epicardial surface where regurgitation is minimized or eliminated. measuring the width between the location, as presently deformed by the width measurement instrument in the identified location, with a force used at the identified location to establish the minimization or elimination of regurgitation and a location opposite the identified location, on an opposite epicardial surface; removing the width measuring instrument from the chest cavity, out of the device port; and selecting the device having opposing contact surfaces defining a width that most closely matches the width measurement.

In at least one embodiment, the valve being treated is the mitral valve, the method further including: prior to introducing the device, assessing an anterior-posterior dimension of a transverse sinus of the heart, the assessing comprising: inserting a length sizing instrument through the tool port with a manipulating instrument operated from outside of the tool port; manipulating the length sizing instrument with the manipulating instrument to insert the length sizing instrument into the transverse sinus; inserting the length sizing instrument to extend over a usable length of the transverse sinus that does not include an obstruction; reading a length measured by the length sizing instrument when fully inserted in the usable length; removing the length sizing instrument from the chest cavity; and selecting the device that has an anterior arm have a best match to the length measured.

In at least one embodiment, the reading comprises grasping the length sizing instrument with an instrument and reading a measurement along a gradient scale on the length sizing instrument, using the camera, wherein the reading is taken at a location where the length sizing instrument is at an open end of the transverse sinus.

In at least one embodiment, the valve being treated is the tricuspid valve.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1B show unassembled views of an epicardial device according to an embodiment of the present invention.

FIG. 1C is a side view of a pad illustrating an optional expandable feature according to an embodiment of the present invention.

FIG. 4A-4D include cross-sectional illustrations of variants showing the relationship and fit between an anterior segment and sleeve according to an embodiment of the present invention.

FIG. 4E is a perspective illustration of the sleeve of any of FIGS. 4A-4D.

FIGS. 43A-43B show two different perspective views of an implant insertion cradle according to an embodiment of the present invention.

FIG. 43C illustrates sutures that can be used to attach a device to the implant insertion cradle of FIGS. 43A-43B, according to an embodiment of the present invention.

FIG. 43D shows the implant insertion cradle of FIGS. 43A-43B attached to a device, according to an embodiment of the present invention.

FIG. 43E is an enlarged view of the portion of FIG. 43D within box 43D.

FIGS. 45A-44B schematically illustrate events that may be carried out during an implantation of a device according to another embodiment of the present invention.

FIG. 45E is a cross-sectional illustration of the device of FIG. 45D taken along line 45E-45E.

FIG. 45F is a cross-sectional illustration of the device of FIG. 45D taken along line 45F-45F.

FIG. 46 illustrates a device having been installed epicardially on a heart of a patient for treatment of tricuspid valve regurgitation, according to an embodiment of the present invention.

DETAILED DESCRIPTION OF THE INVENTION

Figure 2B:
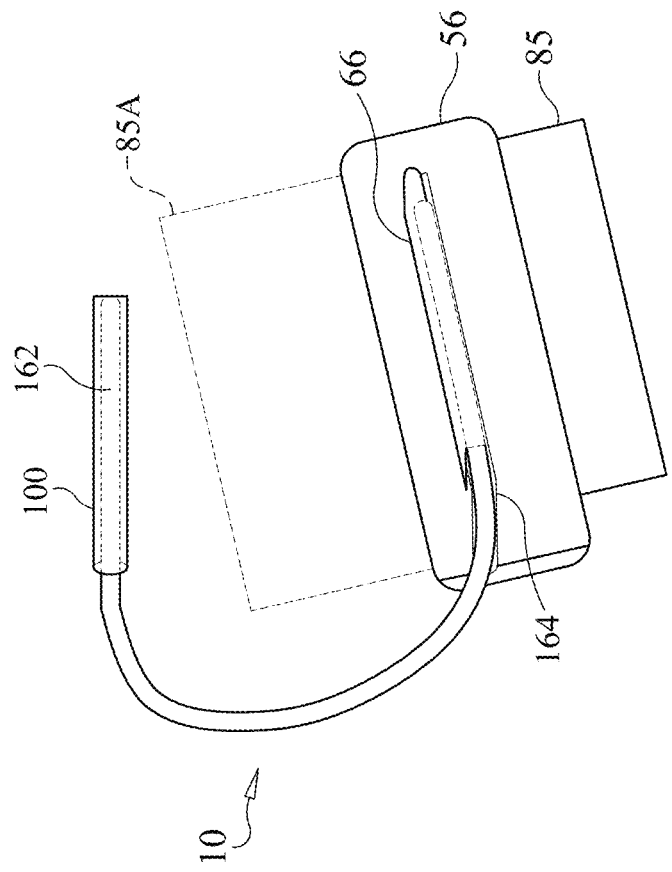
FIGS. 2A-2B illustrate the devices of FIGS. 1A-1B in connected configurations.

Before the present implants, systems and methods are described, it is to be understood that this invention is not limited to particular implants, systems and methods described, as such may, of course, vary. It is also to be understood that the terminology used herein is for the purpose of describing particular embodiments only, and is not intended to be limiting, since the scope of the present invention will be limited only by the claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a segment" includes a plurality of such segments and reference to "the arm" includes reference to one or more arms and equivalents thereof known to those skilled in the art, and so forth.

The publications discussed herein are provided solely for their disclosure prior to the filing date of the present application. Further, the dates of publication provided may be different from the actual publication dates which may need to be independently confirmed.

Definitions

As used in the specification and the appended claims, the term "anterior" is used in its anatomical sense to mean "toward the front, in front of, or the front surface of."

As used in the specification and the appended claims, the term "posterior" is used in its anatomical sense to mean "toward the back, in back of, or the back surface of."

As used in the specification and the appended claims, the term "superior" is used in its anatomical sense to mean "above, over top of, directed upward or toward the head."

As used in the specification and the appended claims, the term "inferior" is used in its anatomical sense to mean "below, underneath, directed downward or toward the feet."

As used in the specification and the appended claims, the term "lateral" is used in its anatomical sense to mean "a position or direction farther from the sagittal or median plane or midline of the body, to the side of, or the side surface of."

As used in the specification and the appended claims, the terms "tube" and "tubular" refer to a long, hollow body which may be round or non-round in cross-section. Thus a "tube" or "tubular" structure, as used herein, includes a hollow cylinder, as well as long, hollow structures that are not round in cross-section, such as the sleeve 100 illustrated in FIGS. 4A-4G.

FIGS. 1A-1B show unassembled views of a device 10 according to an embodiment of the present invention. In the embodiment shown, the epicardial device 10 includes an anterior sheath or sleeve 100, a pad 56 with a flap 85 and a main body 160 comprising a curved member. The main body 160 can be described as having an anterior segment 162, a posterior segment 164 and a lateral segment 166 interconnecting the anterior segment 162 and posterior segment 164.

In this embodiment, device 10 may have a generally U-shape or C-shape when viewed from a top or bottom view, and which can also be seen in this perspective orientation. The device 10 may be shaped such that the distance 160D across the device 10 between the contact surface of the anterior segment 162 and the contact surface of the posterior segment 164 defines the space between which the valve and valve annulus (e.g., the mitral valve and mitral valve annulus), as well as the heart walls apposite these features, will be located after implantation of the device 10 and may determine the final diameter of the valve annulus (e.g., the anterior-posterior diameter in the case of the mitral valve annulus). The anterior segment 162 may be substantially straight, and thus capable of residing in the transverse sinus of the heart. The posterior segment 164 may be arcuate, corresponding to the convex curvature of the posterior ventricular wall of the heart in a location where it is designed to be positioned for implantation. The lateral segment 166 interconnects the anterior 162 and posterior 164 segments with a sufficient length to establish the appropriate distance 160D between the segments 162 and 164 for effectively applying force to the mitral valve annulus to cause a reduction or elimination of mitral valve regurgitation. The main body or frame 160 of device 10 extends through all segments 162, 164 and 166 and is non-flexible and rigid to an extent wherein the conformation shown is not readily deformed and is not deformed by the forces applied to it by the beating heart when it is implanted. In this embodiment, main body 160 is formed by a metal wire, preferably out of titanium or titanium alloy, but could alternatively be formed from other biocompatible metals such as stainless steel, such as 304V, 304L, and 316LV stainless steel; mild steel; nickel-titanium alloy such as linear-elastic and/or super-elastic nitinol; other nickel alloys such as nickel-chromium-molybdenum alloys, and the like.

The posterior segment 164 in this embodiment includes a pad 56 which is preferably compliant and is atraumatic when contacted to target tissue such as the heart. Pad 56 may be formed as molded silicone or other compliant, biocompatible material. Optionally a reinforcing member 56R such as tubing, one or more rods of sheets of reinforcement material may be included within pad 56 to increase the structural strength thereof. The material for reinforcing member 56R could be any of the metals described herein, PTFE or other reinforcing polymer sheets or rigid polymer. Pad 56 may include one or more engagement features 66 that are configured to connect the posterior segment 164 to the pad 56. In the embodiment of FIG. 1A, the engagement features 66 are a pair of hooks 66 spaced apart from one another and partially embedded in the pad 56. The pad 56 may be over-molded on portions of the hooks 66, such that the engagement portions of the hooks extend from the surface of the pad 56. FIG. 1B shows a variant in which a single hook 66 extends from pad 56. The single hook 66 functions in the same manner as the pair of hooks 66 for the engagement function. The single hook 66 further provides more structural rigidity to the pad 56 relative to bending along the length of the pad 56, due to the extent over which the single hook 66 extends over the length of the pad 56. The hook(s) 66 may be made of a rigid material, such as any of the materials described above with regard to main body 160, and/or a rigid, biocompatible polymer. FIG. 1B illustrates in phantom a partial view of posterior segment 164 engaged with hook 66. Note that this embodiment is not limited to one or two hooks 66, as three or more hooks 66 could be employed when aligned in the manner shown by the two hooks 66 in FIG. 1A. Further, engagement members 66 are not limited to hooks, as other types of engaging members could be employed, including, but not limited to: a rigid receptacle formed in pad 56, hook and loop type fasteners provided in mating relationship on pad 56 and posterior segment 164, adhesives, tacks, screws, or other engagement members.

Pad 56 is preferably made from silicone, but could alternatively be made from other moldable, biocompatible polymers. Alternatively, the pad 56 may be encapsulated by a sheath 57, and/or the main frame 160 or one or more portions 162, 164, 166 may be encapsulated by a sheath 57. Still further alternatively, all segments 162, 164 and 166 may be encapsulated by a sheath 57, but typically this is not preferred as the anterior segment will already be received in the sleeve 100. In some embodiments, for example, sheath 57 may be an ePTFE material, non-molded fluorinated ethylene propylene (FEP), a polyester knitted fabric, a polyester velour, a polypropylene felt, a woven or braided fabric, a non-woven fabric, porous material, or other textile material, as desired. Sheath 57 may promote tissue in-growth on the epicardial surface of the heart, may provide tissue in-growth into interstices of the fabric sheath 133, and/or provide adequate frictional forces (traction) to hold the clip 110 in contact with the heart and prevent migration of the device once positioned on the heart. Tissue in-growth therein and/or thereon may provide long-term retention of the clip 110 in a desired position on the heart and prevent erosion. Further optionally the pad 56 may be expandable and contractible to enable the amount of force applied by a contact surface thereof to the tissue that it is applied to, such as the epicardial surface of the heart. FIG. 1C is a side view of a pad 56 that includes an inflatable member 56B that can be inflated or deflated to vary the amount of expansion of the contact surface 56C. By inflating the member 56B the contact surface 56C expands outwardly. When this inflation is performed after anchoring the pad 56 to a target tissue, the subsequent expansion of the contact surface 56C increases the amount of force applied to the target tissue and/or increases displacement of the target tissue that the pad 56 is anchored to. The expandability of the contact surface could alternatively be provided by mechanical means, such as providing channels in the pad with restrictions that can maintain the posterior segment 164 in one position selected from a plurality of positions that define different depths within the pad, so as to select a thickness or distance that exists between the posterior segment 164 and the contact surface 56C. Further optionally, one or more shims may be applied over the contact surface to increase the force applied to the target tissue. Any of the features provided for varying force applied by the contact surface 56C that are disclosed in co-pending U.S. application Ser. No. 16/258,519, titled "Manually Adjustable Device", filed on Jan. 25, 2019, may be applied to any of the embodiments described herein. U.S. application Ser. No. 16/258,519 is hereby incorporated herein in its entirety, by reference thereto. Likewise, any of the features provided for automatically varying force applied by the devices disclosed PCT/US2019/015302, titled "Self-Adjusting Device", filed Jan. 25, 2019, may be applied to any of the embodiments described herein. PCT/US2019/015302 is hereby incorporated herein in its entirety, by reference thereto.

Sleeve 100 is preferably tubular and preferably has a closed end 102 and an open end 104. In the tubular configuration shown in FIGS. 1A-2B, the inside diameter of the tube is only slightly larger (or equal or slightly smaller if the fabric is somewhat expandable) to than the outside diameter of the anterior segment 162 to readily slidably receive the anterior segment therein, while still snugly surrounding and supporting the anterior segment 162. The outside diameter of the anterior segment may be a value in the range from 15 mm to 65 mm. In at least one embodiment, the outside diameter was about 32 mm. Sleeve 100 is preferably fabric and may be made from any of the same materials described above for use in making sheath 57. Sleeve 100 is preferably configured to promote tissue overgrowth, but not tissue ingrowth, so as to enhance fixation of the sleeve 100 to the epicardial tissue, but to also allow the anterior segment 162 to be slid out of the sleeve if necessary. The separate component configuration of the device 10 allows for more variations in implantation procedures that can be performed to install the device.

Figure 2A:
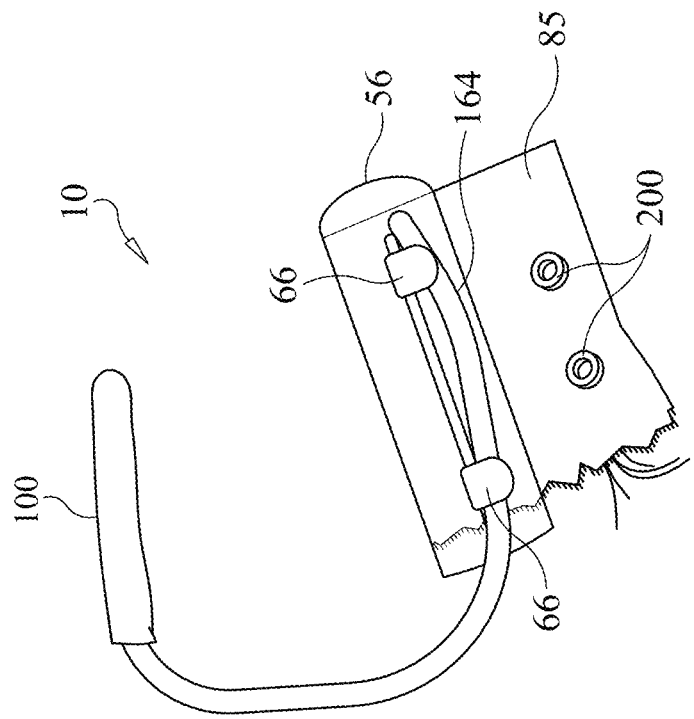

FIGS. 2A-2B illustrate the devices 10 of FIGS. 1A-1B, respectively, in connected configurations. Methods for assembly and implantation of device 10 are described in greater detail below. FIGS. 2A-2B illustrate the anterior segment 162 having been inserted into sleeve 100 and posterior segment 164 having been passed over hook(s) 66 and received within the engagement portion of the hook(s) 66, thereby securing the posterior segment 164 to the pad 56. FIG. 2A further illustrates fixators 200 (tacks, in the example shown) having been installed into flap 85 to secure the flap 85 to the underlying structure (such as the epicardial surface of the heart, for example).

Figure 3A:
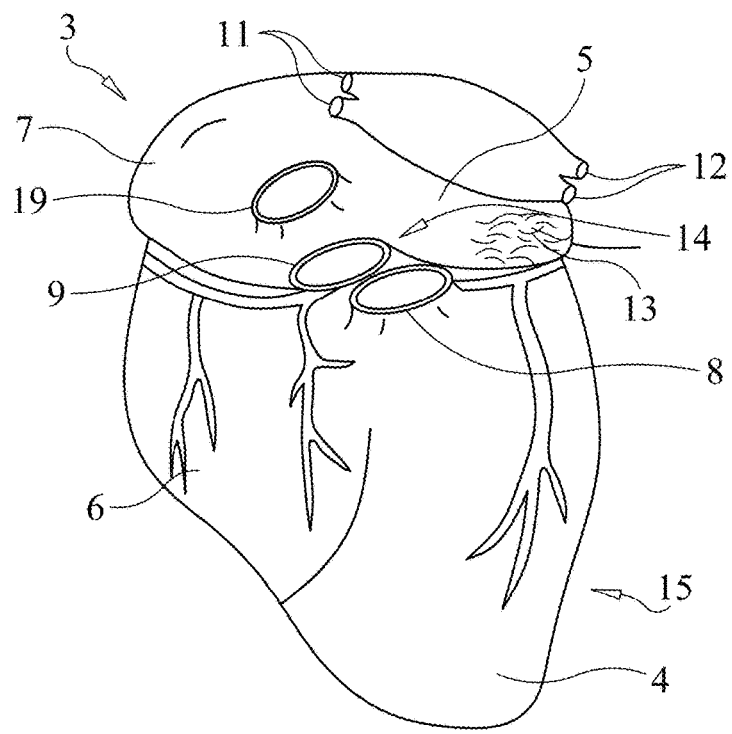
FIGS. 3A-3B are illustrations of a human heart, with the illustration in FIG. 3B viewed with the pericardium removed.
Figure 3B:
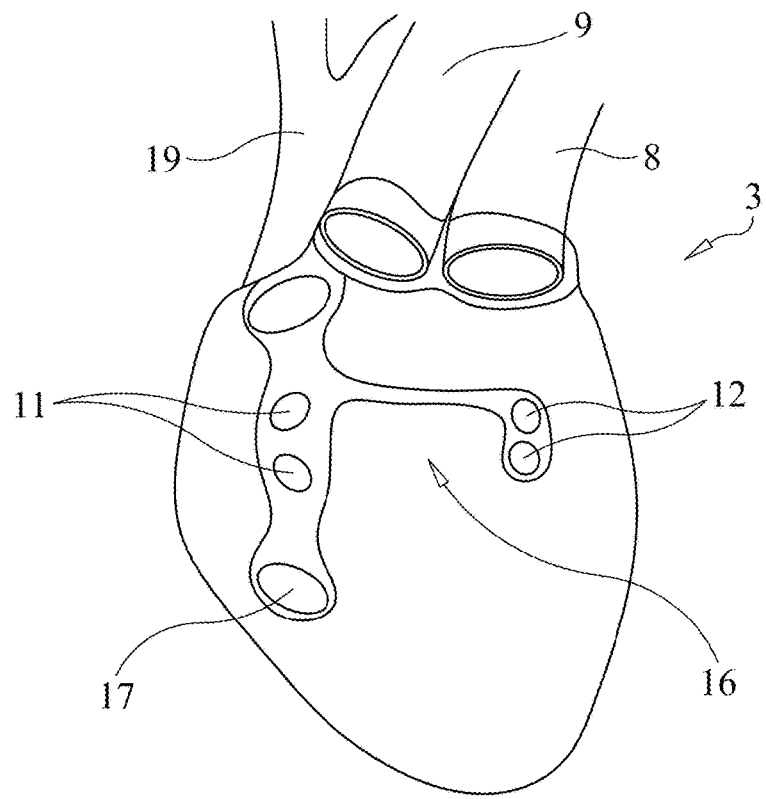

FIGS. 3A-3B are illustrations of a human heart 3, with the illustration in FIG. 3B viewed with the pericardium 15 removed. The chambers of the heart 3 include the left ventricle 4, the left atrium 5, the right ventricle 6, and the right atrium 7. Also shown are the pulmonary trunk 8, the aorta 9, the superior vena cava 19, the right pulmonary veins 11, the left pulmonary veins 12, and the left atrial appendage 13. The transverse sinus 14 is also referenced in FIG. 3A. The transverse sinus 14 is a pericardial cavity between the pericardium 15 and the epicardial surface of the heart 3 located posterior to the aorta 9 and the pulmonary trunk 8 and anterior to the left atrium 5 and the superior vena cava 19. The pericardial sac or pericardium 15, which is a tissue membrane covering the epicardial surface of the heart 3, is also shown removed from the heart 3 in FIG. 3B to further illustrate noteworthy anatomy of the heart 3. The oblique sinus 16 is a blind (e.g., cul-de-sac) recess on the posterior of the heart 3 formed between the pericardium 15 and the epicardial surface of the heart 3. The oblique sinus 16 lies generally between the right pulmonary veins 11 and the left pulmonary veins 12, with the thoracic part of the inferior vena cava 17 located on the side of the pulmonary veins 11. Only two layers of serous pericardium separate the transverse sinus 14 and the oblique sinus 16.

For example, the device 10 may be implanted during a beating heart surgery, without the need of a heart/lung bypass machine. For instance, the device 10 may be implanted on the heart through an open chest procedure (sternotomy) or a lateral thoracotomy. Alternatively, the device 10 may be implanted by minimally-invasive procedures, such as through use of one or more cannulae inserted through the chest without the need to perform an open-chest procedure, and which may be carried out endoscopically, for example. The performance of a minimally-invasive procedure may include access through an incision on the order of 2.5 cm or smaller. In one cadavers study the full device was delivered via a left mini-thoracotomy and using a Da Vinci Surgical Robot. Port access with camera and robots used common Intuitive Surgical Access Ports and entry locations. Size, location and tools for access ports were as follows: Port 1: size 8, 4th intercostal space, midclavicular line, camera, Port 2: size 6, 2nd intercostal space, superior tool port, Port 3: size 6, 6th intercostal space, midaxillary line, inferolateral tool port, Port 4: size 6, subxyphoid, inferomedial tool port. Port 5: Alexis O Wound Protector/Retractor, 4th intercostal, midaxillary line, device placement port, seal with wetted gauze.

The mitral device was delivered through the Alexis O wound retractor port. The device was delivered anterior arm first and by holding the posterior pad with forceps. The device was rotated for entry and handed off to the internal robot arms. The Alexis was sealed with wet gauze allowing insufflation of the chest to 10-15 mmHg for improved access and visualization for placement. All manipulation, placement was performed via the robotic arms. Port access site was used for mechanical anchor delivery supported with robot camera visualization and stabilization of the anchor delivery was assisted by robot tools internal to the cavity. With this system, technical success of implantation and removal of this one embodiment has been demonstrated in a human cadaver. An open chest procedure may include performing a sternotomy to allow access to the thoracic cavity for direct visual placement of the device 10 on the heart 3, either during a beating heart procedure or a procedure in which the heart 3 is not beating, having been bypassed. The pericardium 15 may be incised to access the pericardial cavity between the pericardium 15 and the epicardial surface of the heart 3. Regardless of whether the procedure is minimally-invasive or open-chest, performed with a sternotomy or thoracotomy, the sleeve 100 is installed in the transverse sinus 14. The pad 56 is anchored to the posterior wall of the epicardial surface of the left ventricle 4, such as by fixing the flap 85 to the ventricle, using one or more fixators 200. The anterior segment 162 is typically straight as shown in FIGS. 1A-2B and is readily slid into the sleeve 100 having been installed in the transverse sinus 14. After insertion of the anterior segment 162 as described, the main body 160 can then be rotated about the axis of the anterior segment 162 so that the posterior segment 164 passes over and below (inferior to) the hook(s) 66. The posterior segment is then moved upwardly and into the hooked portion(s) of the hook(s) 66 where it is captured and prevented from becoming disengaged with the hook(s) 66/pad 56. The device 10 is thereby captured by the sleeve 100 and engagement members 66/pad 56. The posterior segment 164 is typically curved as shown, to conform to the curvature of the posterior epicardial wall of the left ventricle 4. The pad 56 functions to distribute forces from the posterior segment 164 over a larger surface area of the ventricle relative to the surface area that the posterior segment 164 would directly apply force to if the pad 56 were not present. The reaction forces of the heart wall 3 against the pad 56 help to ensure that the posterior segment 164 is not released out of the engagement members/hooks 66. The anterior segment 164 may be positioned in sleeve 100 in the transverse sinus 14 posterior to the aorta 9 and the pulmonary trunk 8 and anterior to the left atrium 5 and the superior vena cava 19. Thus, the anterior segment 162 may be located in the transverse sinus 14. The posterior segment 164 may be positioned on the posterior side of the heart 3, such as on or inferior to the atrioventricular groove or in the oblique sinus 16. Thus, the posterior segment 164 may be located on or inferior to the atrioventricular groove or in the oblique sinus 16. In some embodiments, the posterior segment 164 may be positioned inferior to the atrioventricular groove on the posterior side of the heart 3. The lateral segment 166 may extend around the left lateral side of the heart 3 such that the anterior segment 162 is properly positioned in the transverse sinus 14 while the posterior segment 164 is properly positioned on the posterior side of the heart 3, such as on or inferior to the atrioventricular groove or in the oblique sinus 16. In some embodiments, the lateral segment 166 may extend around the heart 3 at a location inferior to the left atrial appendage 13. However, in other embodiments the lateral segment 166 may extend around the heart 3 at a location superior to the left atrial appendage 13 or over the left atrium 5 to join the anterior segment 20 and the posterior segment 24.

In some embodiments, device 10 may include a drug eluting coating in addition to or as an alternative to sheath 57. The drug eluting coating may a controlled release of a therapeutic agent over a specified period of time. The therapeutic agent may be any medicinal agent which may provide a desired effect. Suitable therapeutic agents include drugs, genetic materials, and biological materials. Some suitable therapeutic agents which may be loaded in the drug eluting coating include, but are not necessarily limited to, antibiotics, antimicrobials, antioxidants, anti-arrhythmics, cell growth factors, immunosuppressants such as tacrolimus, everolimus, and rapamycin (sirolimus), therapeutic antibodies, wound healing agents, therapeutic gene transfer constructs, peptides, proteins, extracellular matrix components, steroidal and non-steroidal anti-inflammatory agents, antiproliferative agents such as steroids, vitamins and restenosis inhibiting drugs, such as Taxol®, paclitaxel (i.e., paclitaxel, paclitaxel analogues, or paclitaxel derivatives, and mixtures thereof).

Flap 85 extends inferiorly from the pad 56 in the embodiments of FIGS. 1A-2B. Flap 85 functions to anchor the pad 56 to the posterior wall of the heart when the flap is anchored to the posterior wall of the heart 200. Flap 85 may be formed integrally with pad 56 and may be of the same or different material. Typically the flap 85 is made of a material described above for use in making sheath 57. Flap 85 may be attached directly to the main frame 160 in embodiments where a pad 56 is not employed. Flap 85 may be manufactured separately and then mechanically and/or chemically fixed to pad 56 or main frame 160. Optionally, a second flap 85A (see FIG. 2B) may extend superiorly from the pad 56, wherein second flap 85A is configured to be folded down over the posterior segment 164 and attachment member 66 to thereby further secure the engagement of the posterior segment 164 to the pad 56. Additionally, as the second flap 85A may be made of the same material used to make flap 85 and/or sleeve 100, the second flap 85 may function to allow tissue overgrowth, but prevent tissue ingrowth into the engagement between the posterior segment 164 and the engagement member 66.

The securement of the pad 56 by anchoring the flap 85 to the posterior epicardial surface of the left ventricle is one of the more physically challenging steps in a procedure for implanting the device 10. By providing the device 10 as separate, assembleable components as described herein, this allows the pad 56/flap 85 to be anchored in place prior to installation of the main body 100/posterior segment 164 thereto. This is advantageous in that it allows placement of the pad 56 and fixation thereof via anchoring flap 85 while no force is applied to the pad through the posterior segment 164.

FIGS. 4A-4D include cross-sectional illustrations of variants showing the relationship and fit between an anterior segment 162 and sleeve 100 according to an embodiment of the present invention. FIG. 4E is a perspective illustration of the sleeve 100 of any of FIGS. 4A-4D.

Figure 4F:
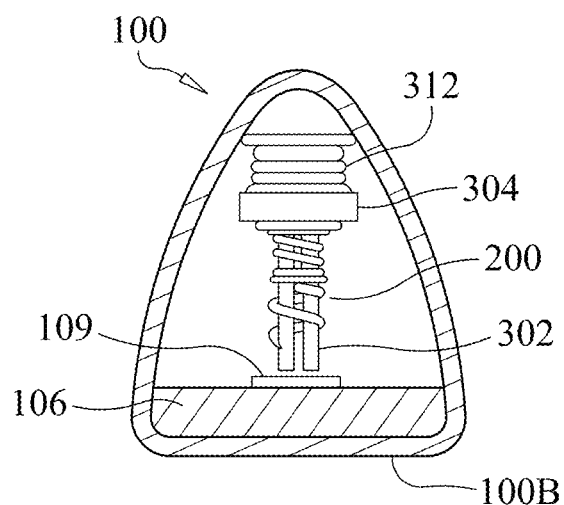
FIGS. 4F-4G are cross-sectional views of a sleeve with a fixator being initially applied to be driven to anchor the sleeve, according to an embodiment of the present invention.

FIGS. 4A-4G all include sleeves 100 having a relatively flat bottom surface 100B configured to abut against the heart tissue at the bottom of the transverse sinus 14. The side walls 100S taper from the largest cross-sectional dimension of the sleeve wherein the side walls 100S join the bottom wall 100B, or less than one third of the distance up from the bottom wall 100B to the top 100T of the sleeve, to a smallest cross-sectional dimension at the top 100T of the sleeve. The resulting external contour of the sleeve is designed to better fit the anatomy of the transverse sinus 14 into which it is to be placed. FIG. 4A illustrates the inside dimensions of the sleeve 100 being greater than the outside diameter of the anterior segment 162 thereby providing a loose fit between the anterior segment 162 and the sleeve 100 when the anterior segment is slid therein. The bottom interior of the sleeve may include an additional layer 106 that may provide some cushioning between the anterior segment 162 and the heart tissue that it applies forces to, and/or help to distribute the forces applied by the anterior segment 162. In at least one embodiment, the additional layer 106 is made of molded silicone. Alternatively the layer may be made of any of the fabrics described herein.

In FIG. 4B a contoured pad 108A is provided at the bottom of the interior space of the sleeve 100 and extends upwardly along the side walls 100S. Pad 108A is preferably silicone but may, alternatively, be formed of other resilient, biocompatible polymer, including, but not limited to foams. A receptacle 110A is formed in pad 108A so that the upper surface generally conforms to the shape of the anterior segment 162 to be received therein. Thus, for example, the receptacle 110A in FIG. 4B is formed generally as a trough have a circular radius of curvature in cross-section. The cross-sectional curve is a semi-circle, as illustrated in FIG. 4B, therefor the anterior segment 162 can pass into the receptacle 110A without the need to deform the walls of the receptacle 110A. Not only does receptacle 110A help to provide some cushioning between the anterior segment 162 and the heart tissue that it applies forces to, and/or help to distribute the forces applied by the anterior segment 162, but it also increases the frictional forces between the anterior segment 162 and the sleeve 100/receptacle 110A, helping prevent relative sliding between the anterior segment 162 and sleeve 100/receptacle 110A.

FIGS. 4C-4D illustrate another variant in which the receptacle 110B of the contoured pad 108B has a cross-sectional curvature that is greater than a semi-circle, but less than a full circle. The portions 110R of the contoured pad 108B that extend beyond the lower portion of the receptacle 110B that forms a semi-circle in cross section, converge toward one another such that a gap formed at the opening between the ends of these portions is less than the outside diameter of the anterior segment 162. The minority portion need only be from about 10% to 25% of the overall curve formed by the receptacle 110B and is preferably equally distributed at both sides of the top, as shown in FIG. 4C. Alternatively the minority portion could be formed in only one side, although this is less preferable. Upon insertion of the anterior segment 162 into the contoured pad 108B, the segment 162 contacts the minority portions of the receptacle 110B and forces them apart (in the direction of the arrows shown in FIG. 4C) to allow the segment 162 to pass by and be positioned within the receptacle 110B. As the segment 162 passes the minority portions and enters into the main cavity defined by the receptacle, the minority portions resiliently return to their original configuration (by moving in the directions of the arrows shown in FIG. 4D), thereby further cradling the segment 162 in comparison to the amount of cradling performed by the receptacle 108A. This provides even greater frictional forces and resistance to movement of the anterior segment 162 relative to the sleeve 100/receptacle 110B once the segment has been received and placed in its intended position.

FIG. 4E is a perspective view of the sleeve 100 shown in any of FIGS. 4A-4D, illustrating the external contours of the sleeve that are configured to match the target site anatomy (e.g., transverse sinus).

Figure 4G:
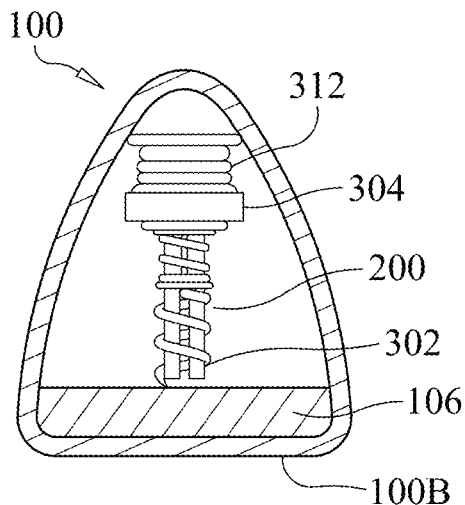

FIGS. 4F-4G are cross-sectional views of a sleeve 100 with a fixator 200 being initially applied to be driven to anchor the sleeve 100. As shown, the additional layer 106 is employed in the sleeve 100. Alternatively, one of the contoured 108A or 108B could be substituted for the layer 106. In FIGS. 4F and 4G, the distal end portion of fixator driver 300 (see FIG. 17B) has been inserted in sleeve 100 to perform anchoring of the sleeve 100 to target surgical tissue. As already noted, in the case of anchoring in the transverse sinus, the flat surface provided by the bottom 100B and layer 106 help to maintain the orientation of the driver head 304, shaft 302 and fixator 200 normal to the surface of the tissue (bottom of the transverse sinus 14, trigones 14T) to be anchored to. Additionally, the side walls 100S and top 100T of the sleeve 100 are configured to confine the distal working end of the driver 300 and apply some downward force to the head 304 that aids in the initial driving of the fixator 200.

Figure 4H:
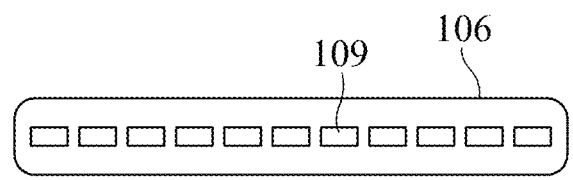
FIGS. 4H, 4I and 4J show various arrangements for retaining doors according to embodiments of the present invention.
Figure 4I:
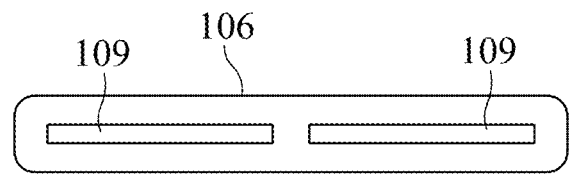
Figure 4J:
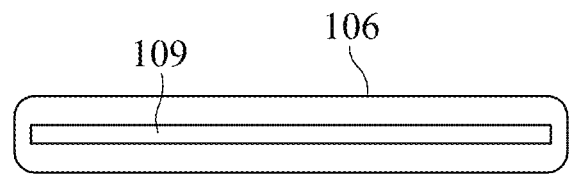

Optionally, a retaining door 109 may be provided on top of the layer 106 (or on top of 108A or 108B) as shown in FIG. 4F. The retaining door extends slightly above the surface of layer 106 so that as the fixator 200 is rotated, the raised layer of the door 109 catches the sharp distal tip 204 of the fixator 200. Continued rotation of the fixator 200 by the driver 300 draws the fixator into the door 109, through the layers 106, 100B and into the target tissue, thereby anchoring the sleeve 100 to the target tissue. Retaining door 109 may be provided at any position along the length of the pad 106, 108A or 108B, may be provided as a plurality of individual doors or as a semi-continuous or continuous strip as illustrated in FIGS. 4H, 4I and 4J, respectively. Each retaining door 109 may be made from the same material as the pad 106, 108A or 108B.

FIGS. 5A-5D illustrate various views during the fixation of a sleeve 100 during an implantation procedure, and installation of the anterior member 162 into the sleeve 100, according to an embodiment of the present invention. The embodiments of sleeve 100 shown in FIGS. 1A-2B and 4A-4E can be installed into a target site such as the transverse sinus, without further anchoring, after which anterior segment 162 can be inserted into the sleeve 100. Preferably the sleeves 100 of FIGS. 1A-2B and 4A-4E can be anchored at the target site, in addition to the placement described, to enhance the fixation of the sleeve at desired location and orientation, prior to insertion of the anterior segment 162.

Figure 5A:
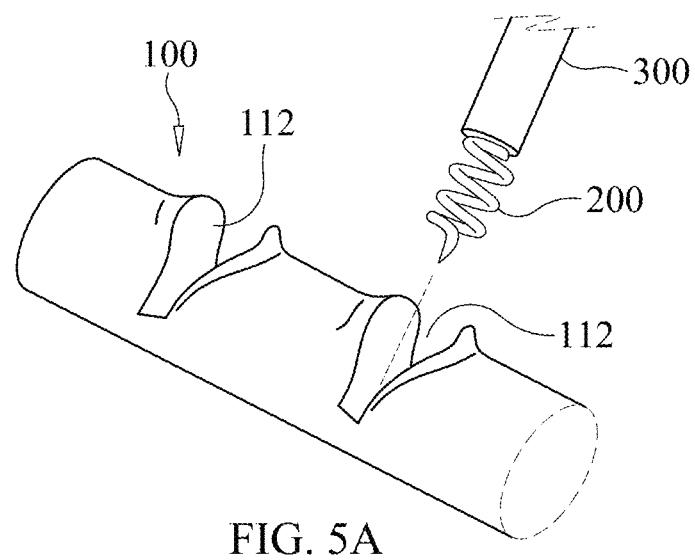
FIGS. 5A-5D illustrate various views during the fixation of a sleeve during an implantation procedure, and installation of an anterior member into the sleeve, according to an embodiment of the present invention.

FIG. 5A schematically illustrates openings or slits 112 provided in the top of the sleeve 100 which are configured and dimensioned to permit fixators 200 to be inserted therethrough. The opening or slit 112 may be an opening such as a circular opening having a diameter slightly greater than the diameter of the fixator 200 to be inserted therethrough, or may be a much narrower slit that allows the leading end of the fixator 200 to pass therethrough. Upon rotation of the fixator 200 it can then thread its way through the slit 112 and the distal end of the fixator driver 300 can dilate the slit 112 open to allow entrance of the fixator driver 300. FIG. 5A illustrates a fixator 200 (in this instance, fixator 200 is a tack) installed on a fixator driver 300 (in this instance, a tack driver) and aligned with one of the openings 112 to be inserted therethrough. In instances where the target site is the transverse sinus 14, the bottom surface 100B and opening 112 can be configured so as to align the fixator perpendicular (or as near perpendicular as possible) to the trigones 14T (cartilaginous structure underlying the base of the transverse sinus, sometimes referred to as the "backbone" of the heart 3). This cartilaginous structure is the target for securement, as it provides the best anchorage of the sleeve 100 via the fixators 200.

Figure 5B:
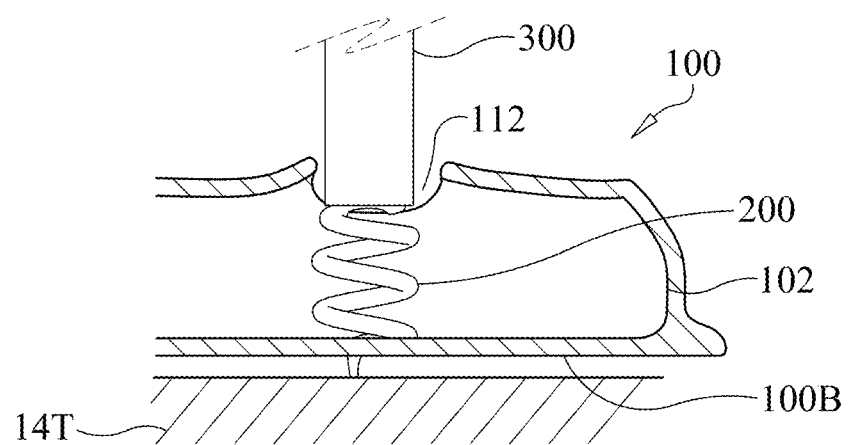

FIG. 5B illustrates fixator 200 having been inserted through opening 112, with the distal end of the fixator driver 300 also having entered through the opening. The fixator 200 can then be driven through the bottom surface 100B of the sleeve 100, into the base of the transverse sinus and into the trigones 14T. Optionally the bottom surface 100B may have an opening provided therein which is aligned with opening 112, but this is not necessary and typically not preferred, as the fixator has a sharp end that can be readily driven through the material of the bottom surface 100B. Also by not providing an opening in the bottom surface 100B, this results in a closer fit between the fixator 200 and the bottom surface, thereby practically eliminating risk of the fixator 200 pulling through the bottom surface 100B.

Figure 5C:
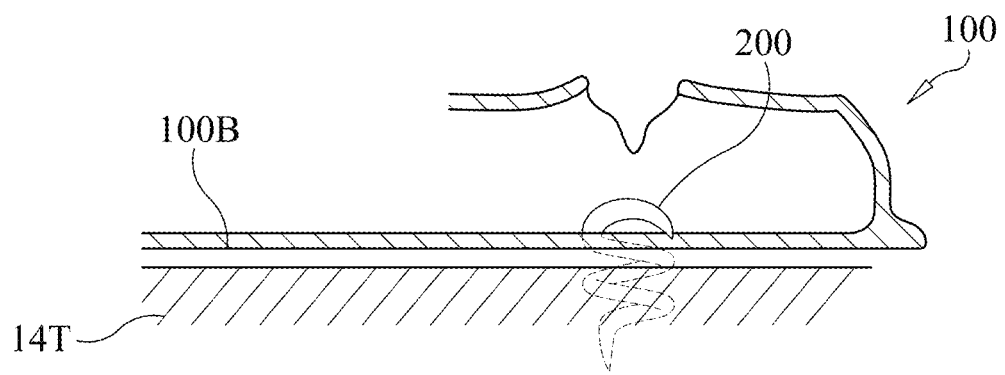

FIG. 5C illustrates the first fixator 200 having been fully installed to fix a portion of the sleeve 100 to the target site. The fixator driver 300 has been removed. The head of the fixator may be flush or nearly flush with the inside wall of the bottom of the sleeve so that the internal opening in the sleeve is largely unadulterated and provides a free and clear pathway for insertion of the anterior segment 162.

Figure 5D:
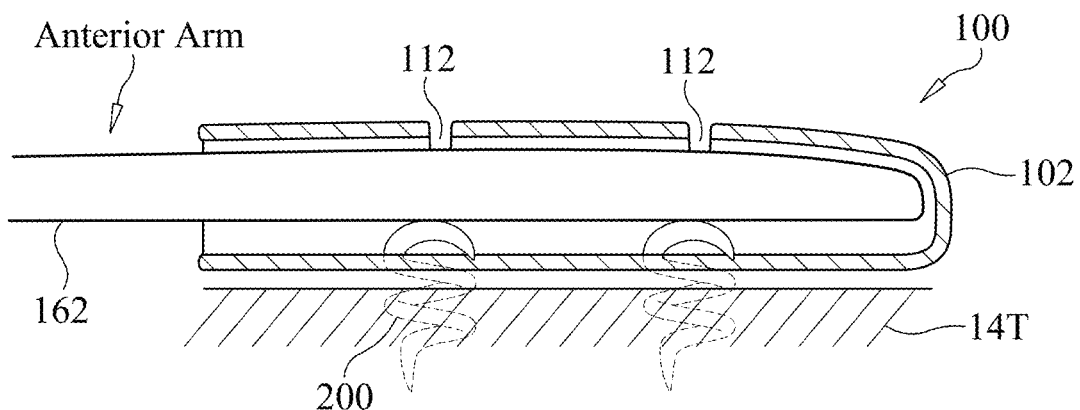

FIG. 5D illustrates a second fixator 200 having been fully installed to fix a portion of the sleeve 100 to the target site. Although this example shows only two fixators 200 being employed, it is noted that the present invention is not limited to use of two fixators, as three or more could be used. Even only one fixator could be used, although it is generally preferred to use at least two fixators 200. FIG. 5D also illustrates that the anterior segment 162 has been inserted into the anchored sleeve 100. Optionally the anterior segment 162 may be inserted until it abuts or nearly approximates the closed end 102 of the sleeve. Alternatively, other positioning markers could be employed to guide the location of the free end of the anterior segment 162. However by placing and anchoring the sleeve 100 correctly, the closed end 102 can serve as the most user friendly guide as it can act as a stop when the free end of the anterior segment 162 abuts it. Although tacks are the preferred form of fixator 200, as noted, alternative fixators may be used, including, but not limited to: screws, staples, sutures, adhesives, hooks, t-bars, combinations of these, or other types of mechanical fixators. By anchoring the sleeve 100 as described, this prevents unwanted sliding action of the anterior segment 162 off of the desired location (trigones 14T of transverse sinus 14). For example, with an anterior segment 162 placed in the transverse sinus 14 without a sleeve, sliding movements away from the trigones and toward the left atrium have been noted at times. When the anterior segment slides off of its intended location site, it no longer exerts the intended, appropriate force to the septal-lateral diameter of the mitral valve. By anchoring the sleeve 100 as described and then inserting the anterior segment 162, this prevents sliding of the anterior segment toward (or away from) the left atrium, thereby maintaining the appropriate force to the septal-lateral diameter of the mitral valve.

Figure 6:
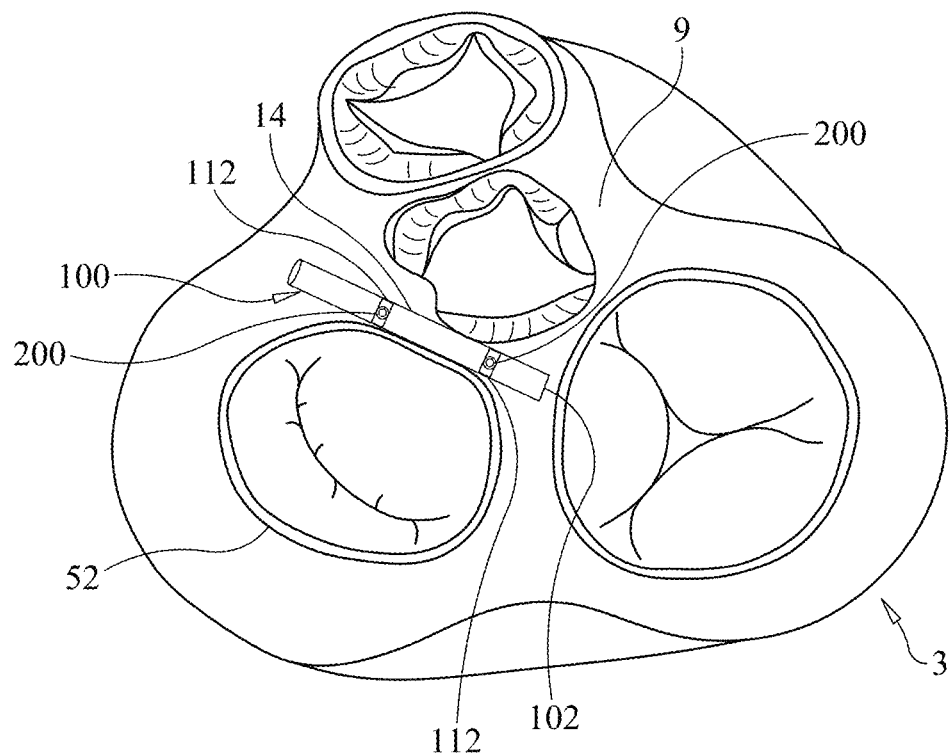
FIG. 6 schematically illustrates a sleeve having been anchored in the transverse sinus of a heart, according to an embodiment of the present invention.

FIG. 6 schematically illustrates a sectional view of a heart, showing the sleeve 100 having been anchored in the transverse sinus 14 of the heart 3, according to an embodiment of the present invention. The transverse sinus 14 is shown located between the aorta 9 and the mitral valve 22. Fixators 200 have been installed through openings 112 and driven through the bottom wall of the sleeve 100 and into the heart tissue at the base of the transverse sinus 14, thereby securely anchoring the sleeve 100 in the transverse sinus 14.

Figure 7:
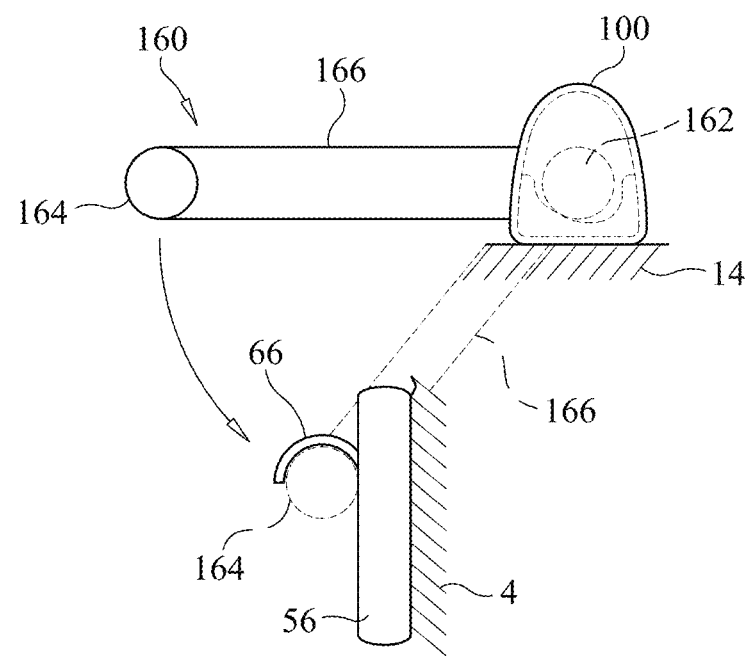
FIG. 7 illustrates approximation of a posterior segment to fix it to a pad, according to an embodiment of the present invention.

Once the anterior segment 162 has been properly installed in the sleeve 100 in a manner as descried above, and after anchoring the pad 56 on the desired target location on the posterior wall of the left atrium (described in greater detail below) the main body 160 can then be rotated about the axis of the anterior segment 162 as indicated by the arrow in FIG. 7, to approximate the posterior segment 164 to the pad 56 and engagement feature 66. The posterior segment 164 is moved toward and past the engagement feature by the rotation motion about the anterior segment 162. As the posterior segment passes the engagement feature 66 it is positioned adjacent the receiving opening of the engagement feature (hook or hooks in FIG. 7, such as those described with regard to FIGS. 1A-2B) and then inserted into the receptacle of the engagement feature 66 where it is captured and prevented from disengaging from the engagement feature 66, thereby securing the posterior segment 164 to the pad 56 and left atrium 5.

Figure 8A:
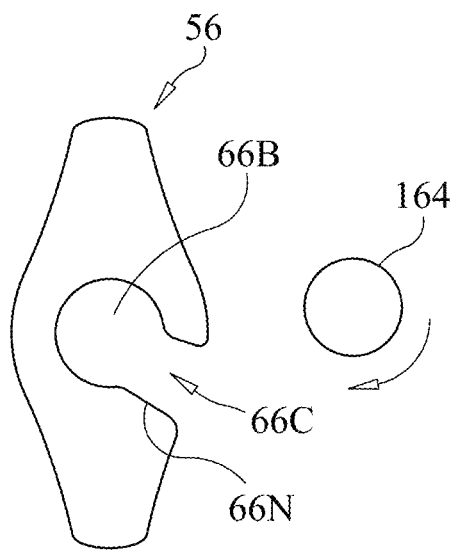
FIGS. 8A-8D schematically illustrate a pad with engagement feature and engagement of a posterior segment therewith, in accordance with an embodiment of the present invention.
Figure 8B:
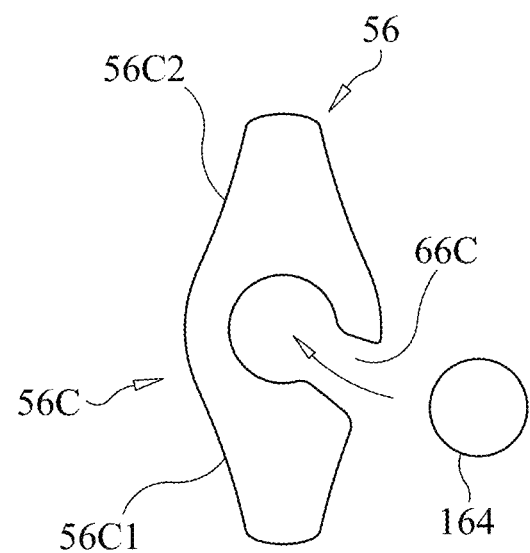
Figure 8C:
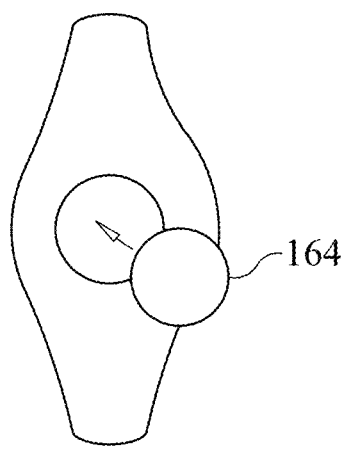
Figure 8D:
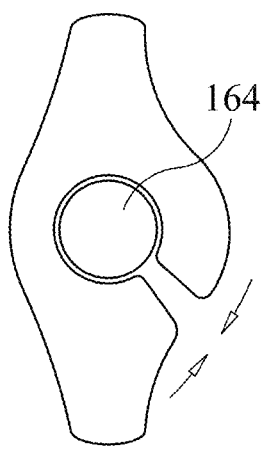

FIGS. 8A-8D schematically illustrate a pad 56 with engagement feature 66 and engagement of a posterior segment 164 therewith, in accordance with another embodiment of the present invention. In this embodiment, engagement feature 66 is one or more receptacles 66 formed into the body of the pad 56 itself. The receptacle(s) 66 may be molded into the pad, for example, or otherwise constructed to have the features shown and described. The main body 66B has an inside diameter or cross-sectional area that approximates (preferably equal to or slightly larger, but could be slightly smaller) than the outside diameter or cross-sectional area of the posterior segment 164. This arrangement allows the posterior segment 164 to be stably maintained in the main body 66B once it has been placed there. The opening 66C may be beveled so that the outside surface of the opening is larger than further inwardly, as the opening tapers down. The opening at the outside surface may be large enough to engage the posterior segment 164 and guide it along the tapered surfaces toward the main body 66. A necked-down region of the engagement feature 66 is a narrowed region that has a diameter or largest cross-sectional dimension that is less than the outside diameter or largest cross-sectional dimension of the posterior segment 164. As the posterior segment 164 is rotated to approximate the engagement feature 66, by rotating the main body 160 about the anterior segment 162 in the same way as described with regard to FIG. 7, the posterior segment can then be inserted into the opening 66C as illustrated in FIG. 8B. As the posterior segment 164 passes through the opening toward the necked down region 66N, it expands the necked down region, since the engagement feature is formed in a flexible, resilient material. This allows driving the posterior segment past the dilated, necked-down region 66N and into the main body, see FIGS. 8C-8D. Once the posterior segment 164 fully resides in the main body, as shown in FIG. 8D, it no longer forces the necked-down region apart. This allows the necked-down region to resiliently return to its unbiased configuration (see arrows in FIG. 8D) where it resumes the geometry as in FIG. 8A. Thus, engagement feature and necked-down region 66N function like a living hinge to accept the posterior segment 164 in the main body receptacle 66B. The resilient return of the necked-down region as in FIG. 8D provides forces helping to prevent escape of the posterior segment 164 from the engagement feature 66, as the dimensions of the necked-down region 66N are again smaller than those of the posterior segment 164. Also, the forces applied by the posterior segment 164 to the heart are in the direction upward and to the left in FIG. 8D and thereby directly oppose the direction in which the posterior segment 164 would need to travel to escape from the engagement feature 66. This is because the posterior segment 164 is integrally joined with the anterior segment 162 that is positioned in the transverse sinus, as described, on the opposite side of the mitral valve and superior to the placement of the posterior segment 164. Therefore the forces applied to and through the posterior segment 164 are in a direction upward and to the left in FIG. 8D, and oppose a force that would be needed to force the posterior segment 164 out of the engagement feature 66.

Figure 9:
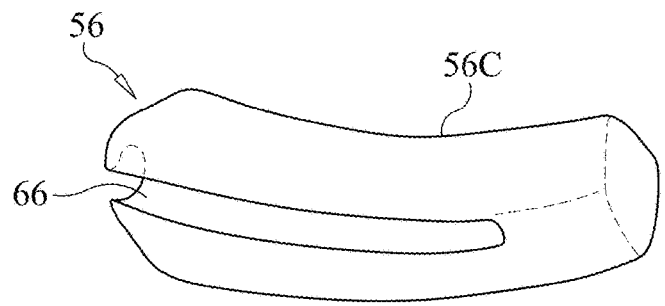
FIG. 9 is an isolated illustration of the posterior pad according to an embodiment of the present invention.
Figure 10:
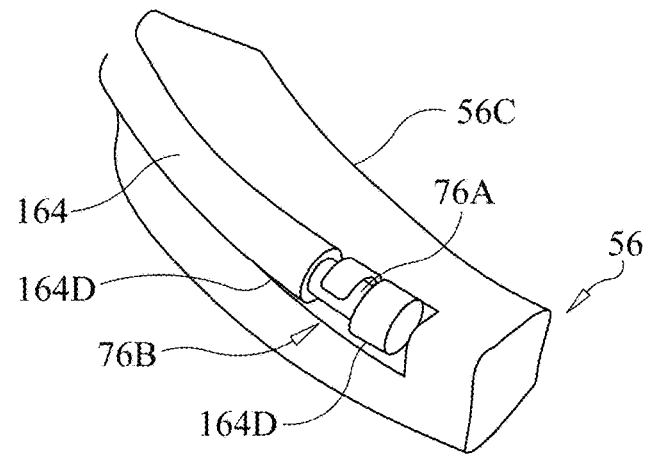
FIG. 10 shows a locating feature that ensures that a posterior segment is inserted into the pad at a correct depth, according to an embodiment of the present invention.
Figure 11:
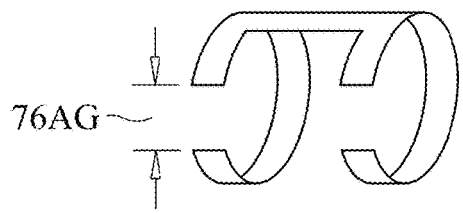
FIG. 11 illustrates a depth gauging clip component from FIG. 10, according to an embodiment of the present invention.
Figure 12:
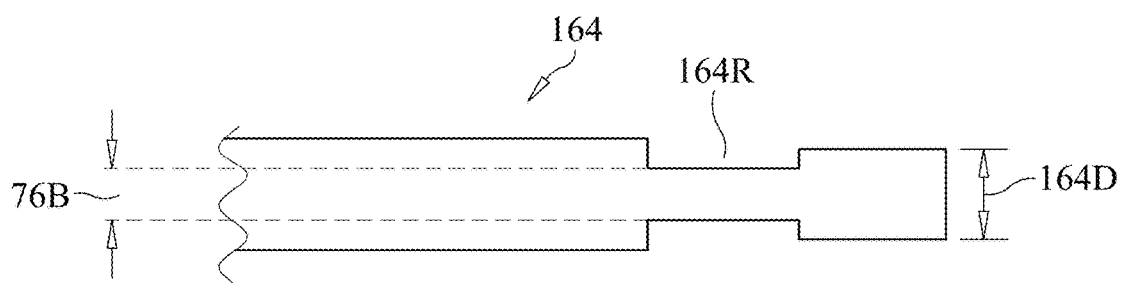
FIG. 12 illustrates a smaller diameter section of a posterior segment according to an embodiment of the present invention.

FIG. 9 is an isolated illustration of the posterior pad 56 according to an embodiment of the present invention, which illustrates that the contact surface 56*c* of the pad 56 can be curved so as to better approximate the shape of the wall of the left ventricle 4 to which it is to be anchored. For example, FIG. 9 shows that the contact surface 56*c* is concave in a direction along the length of the pad 56. The contact surface 56*c* can be generally straight in a direction normal to the longitudinal axis of the pad 56, or could alternatively be curved as well. For example, the contact surface 56*c* could be convex in the normal direction. Further alternatively, the contact surface 56*c* in the direction normal to the longitudinal axis can be forms as a pair of beveled surfaces that angle away from a central portion in directions toward the face of the pad 56 that is opposite of the contact surface, as illustrated in FIG. 8B. Thus, the beveled surfaces approximate a convex shape in the direction normal to the longitudinal axis of the contact surface 56C The engagement feature 66 (which can be a receptacle, as shown in FIG. 9, or could alternatively, be one or more hooks or other engagement features described herein) is located in a surface opposite the contact surface 56*c*. FIG. 10 shows a locating feature 76 that ensures that the posterior segment 164 is inserted into the pad 56 at the correct depth, wherein the correct depth is defined by the length of the portion of the posterior segment 164 that is received in the engagement feature 66. In the embodiment of FIG. 10, the locating feature 76 includes a clip 76A that is dimensioned to receive a member having less than or equal to a predefined diameter or thickness. The posterior segment 164 in FIG. 10 has a consistent outside diameter or thickness 164D all along the length thereof, except for a location 164R having a diameter or thickness 76B (see FIG. 12) that is configured to be received by the clip 76A when the posterior segment 164 has been inserted into the engagement feature at the desired depth, such that the one location aligns with the clip 76A. The one location has a diameter or thickness 76B that is less than 164D and is equal to or, preferably, slightly less than the gap distance 76AG (see FIG. 11) of the clip 76. The portion 164R is located at a predefined length along the length of the posterior segment 164 configured to align it with the clip 76A so that the posterior segment 164 is fixed in the pad 56 at the correct depth or length. In the embodiment shown, the portion 164R is located at the free end portion of the posterior segment 164, near the free end, but spaced somewhat inwardly of the free end. However, this location may vary, as long as the location of the mating clip 76A is varied as well so as to ensure the accurate location of the posterior segment along the length of the feature 66.

Figure 13A:
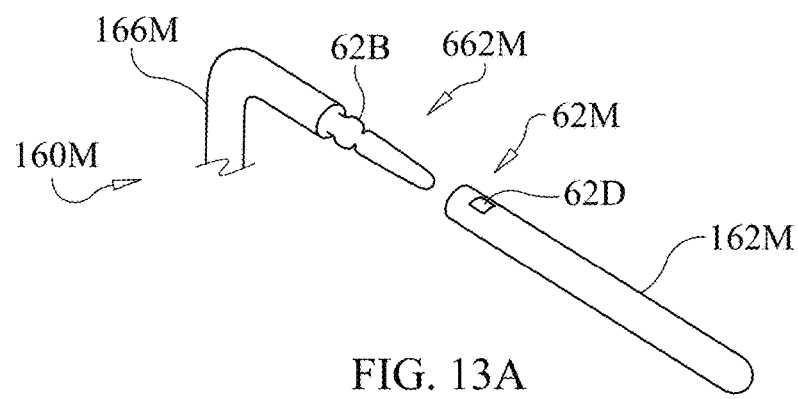
FIGS. 13A-15B show various embodiments of segmented main bodies, according to embodiments of the present invention.
Figure 13B:
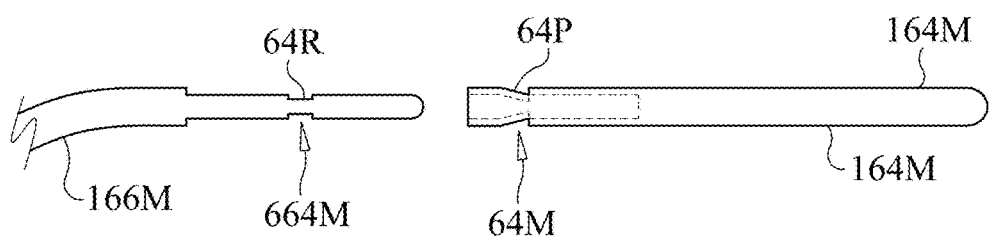

FIGS. 13A-13B illustrate features of a segmented, multi-part main body 160M according to an embodiment of the present invention. Rather than providing the main body as a unitary, integrated main body 160, such as in FIG. 1A, the main body 160 may be provided in multi-part segments. In the embodiment of FIGS. 13A-14B, the main body 160M includes three segments 162M, 164M and 166M. Although this is presently a preferred embodiment, the body 160M could alternatively be provided with only two segments, or greater than three segments. Only portions of the lateral segment 166M are shown in FIGS. 13A-14B so as to illustrate the connecting features on each end thereof. However, the lateral segment 166M will typically appear the same as segment 166 in FIG. 1B upon completion of the assembly of the segments 162M, 164M, 166M.

Figure 14A:
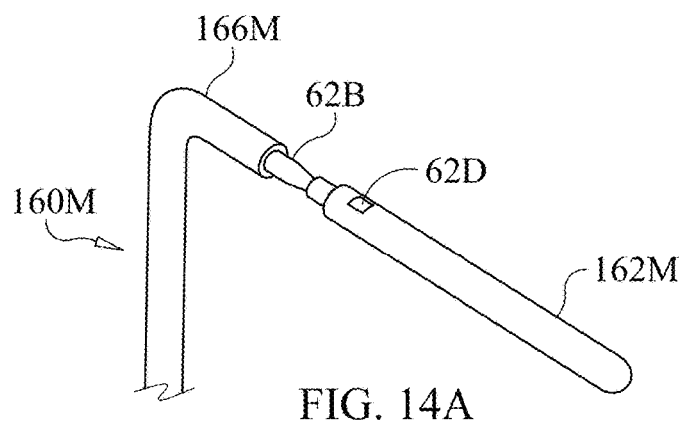

In FIG. 13A, the anterior segment 162M and lateral segment 166M are provided with mating features 62M and 662M that are configured to mate with each other to secure the anterior 162M and lateral 166M segments together. The mating features 62M and 662M may be provided so that they are not releasable once mated, but preferably, and in the embodiment of FIG. 13A, the mating features 62M, 662M releasably fix the components together. FIG. 13A shows a particular type of detent mating arrangement, where one component (166M as shown, but could alternatively be 162M) has a ball or other raised feature 62B that is received in a detent 62D located in the other of the segments 164M, 166M, when the components 62M and 662M are properly aligned and slid together fully so that the components can mate. FIG. 14A shows anterior segment 162M having been partially slid over the lateral segment 166M, but not fully to the extent where the ball 62B is received within the detent 62D.

Figure 14B:
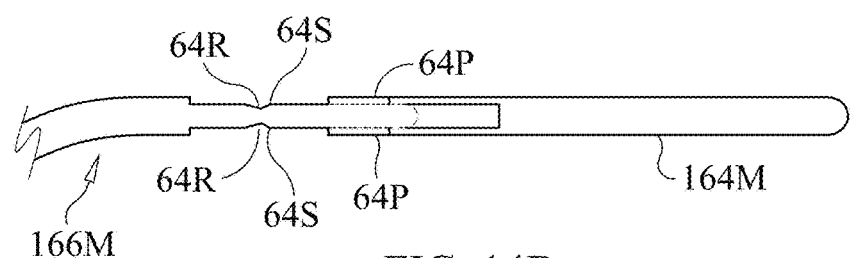

FIG. 13B show the posterior segment 164M and lateral segment 166M are provided with mating features 64M and 664M that are configured to mate with each other to secure the posterior 1642M and lateral 166M segments together. The mating features in this embodiment are another type of detent mating arrangement, but could, alternatively be the same type as shown in FIG. 13A. Further, the mating arrangements of either or both of FIGS. 13A and 13B could be other types of mating arrangements, including, but not limited to still other detent fitting designs, bayonet fittings, threads, snap fit, magnets, adhesives, etc. and/or combinations of the same. The mating features 64M and 664M may be provided so that they are not releasable once mated, or alternatively, the mating features 64M, 664M releasably fix the components together. FIG. 13B shows a particular type of detent mating arrangement, where one component (664M as shown, but could alternatively be 64M) has one or more recesses 64R and the other component (64M as shown, but could alternatively be 664M) has one or more prongs 64P. As portion 664M of segment 166m is slid into portion 64M of segment 164M, the portion 664m resiliently deforms the prongs 64P to allow the portion 664M to slide therepast, as illustrated in FIG. 14B. One the portion 664M is full inserted into portion 64M, the recesses 64R align with the prongs 64P and the prongs 64P resiliently return toward their unbiased configurations, where they are captured by the end shoulders 64S that border the recesses 64R, thereby preventing segment 164M from separating from segment 166M.

The provision of a segmented multi-part main body 160M permits the anterior segment 162M to be implanted, such as by locating it in a sleeve 100 having been anchored in the transverse sinus, as described herein, or by locating it in the transverse sinus, or by implanting it at another surgical target location prior to connecting it to the lateral segment 166M. Likewise the posterior segment 164M can be implanted at a target location prior to connecting it to the lateral segment 166M. For example, the posterior segment can be inserted into or hooked to a posterior pad 56 that has been anchored to the heart, in any of the manners discussed herein. In at least one embodiment, the anterior segment 162M is inserted first and the lateral segment and posterior segment are provided as an integral unit. The lateral segment is attached to the anterior segment 162M after the anterior segment has been placed at the target location. Then the lateral segment (which is integral with the posterior segment) is rotated about the longitudinal axis of the anterior segment to place the posterior segment at its target location where it can be fixed to the pad 56. In another embodiment, the anterior segment and lateral segment are integral and the anterior segment is placed in the same way as described in the previous embodiment. However, in this embodiment, the posterior segment is next connected to the posterior pad 56 prior to connecting it to the lateral segment. The lateral segment can then be rotated about the longitudinal axis of the anterior segment that it is integral with, to connect the lateral segment to the posterior segment. In embodiments were all three segments 162M, 164M and 166M are separately provided, the anterior and posterior segments can be placed and optionally fixed at their target locations prior to the connecting the lateral segment to both. Alternatively, the lateral segment could be first connected to one or both of the anterior and posterior segments prior to placing them. In any of the embodiments that include segmented multi-parts, two or more of the separate parts can be connected prior to placing them in the target location, if desired.

Another advantage provided by segmented, multi-part bodies 160M is that these designs allow for more variation in fitting the body 160M to a particular patient. For example, integral main bodies 160 may be produced in several sizes, with either a short anterior segment 162 or a long anterior segment 162 and with varying lengths of the lateral segment 166, such as four different lengths for four different diameter measurements between the anterior segment 162 and the posterior segment 164. This effectively provides eight different sizes to choose from. However, the usable length of the transverse sinus that can be effectively occupied by the anterior segment may vary substantially among patients. By providing a separate anterior segment 162M, this makes it possible to provide many more than just a short and a long length of anterior segment, at less cost than would be required to make integral bodies 160 each having varying anterior segment lengths. Thus a more customized and optimized fit of the body 160M is possible. Also, this requires less hardware to be kept on hand at the operation site, as all of the various lengths of anterior segment 162M and/or posterior segment 164 can each be readily connected to any of the lateral segments 166M.

Figure 15A:
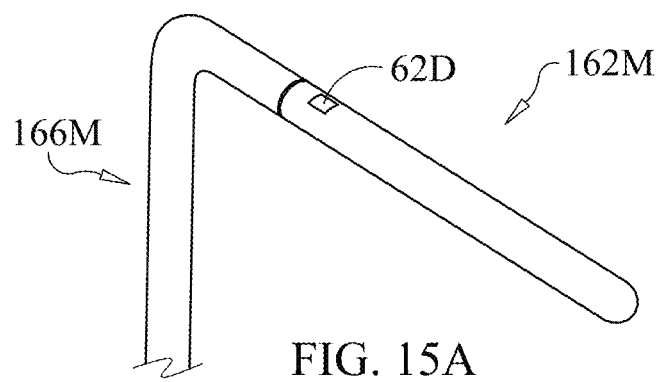
Figure 15B:
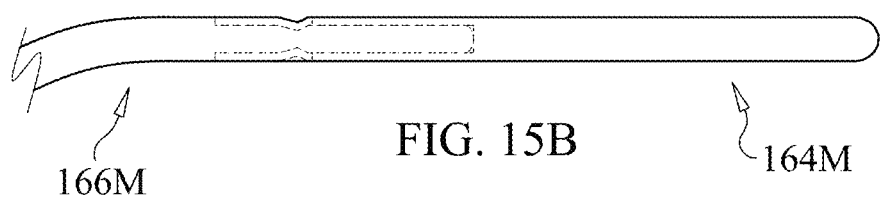

FIGS. 15A-15B illustrate the segments 162M, 166M and 166M, 164M having been connected by the mating of the mating features described above.

Figure 16:
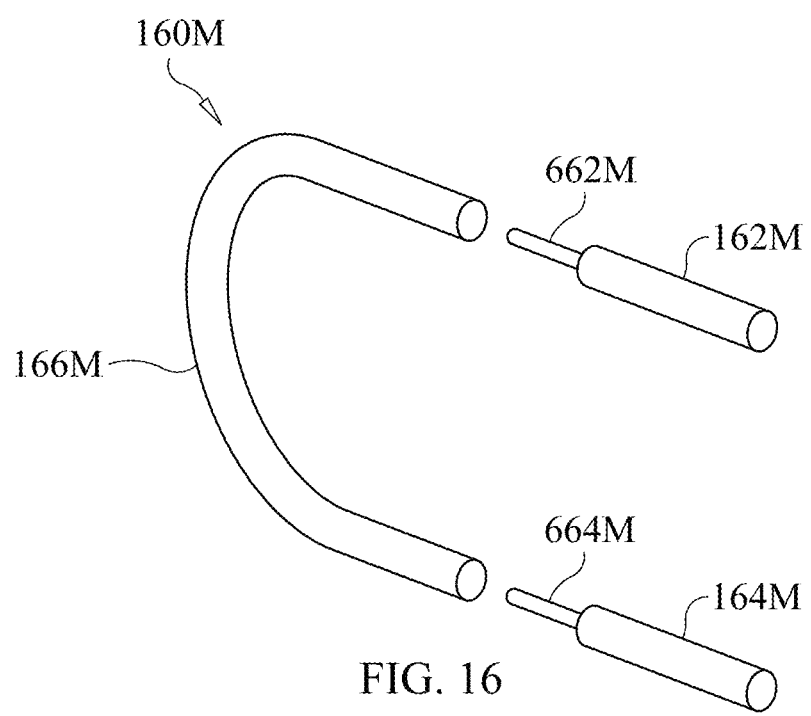
FIG. 16 shows segmented components of a main body that can be joined by magnets, according to an embodiment of the present invention.

FIG. 16 illustrates a segmented, multi-part main body 160M according to another embodiment of the present invention. In this embodiment the lateral segment 166M is a hollow tube, or is a solid tube with hollow end portions having sufficient length to receive the mating features 662M and 664M therein, respectively. The lateral segment 166M may be made of titanium or other more magnetic material such as stainless steel, or at least the hollow end portions may be made of a magnetic material with the remainder being made of a rigid material that need not have as great magnetic properties as the portions that mater with the magnetic mating features 662M, 664M. The mating features in this embodiment are circular magnets 662M, 664M that may be elongated and rod-shaped so as to be slidably received in the opposite end of the lateral segment 166M, as illustrated. The opposite ends of the mating features 662M, 664M may be slidingly received in hollow end portions of the anterior segment 162M and posterior segment 164M, respectively. The magnetic forces between the mating features 662M, 664M and the magnetic metals of the anterior, lateral and posterior segments 162M, 166M, 164M maintain the segments as an integral unit once they are joined. Alternatively, the mating features 662M, 664M may be permanently fixed in the open ends of the anterior segment 162M and posterior segment 164M, respectively, such as by gluing welding, or the like.

Figure 17A:
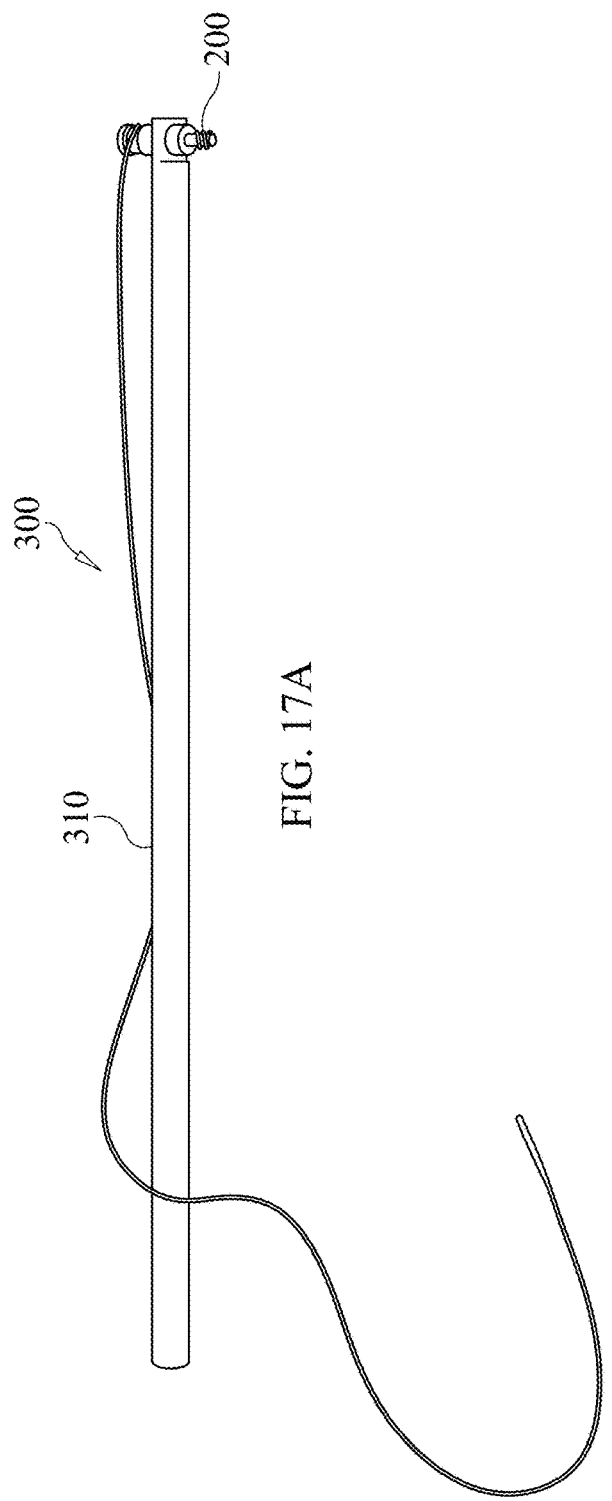
FIG. 17A is a perspective view of a fixator driver that can be used to anchor fixators in tissue to anchor components of the present invention, according to an embodiment of the present invention.
Figure 17B:
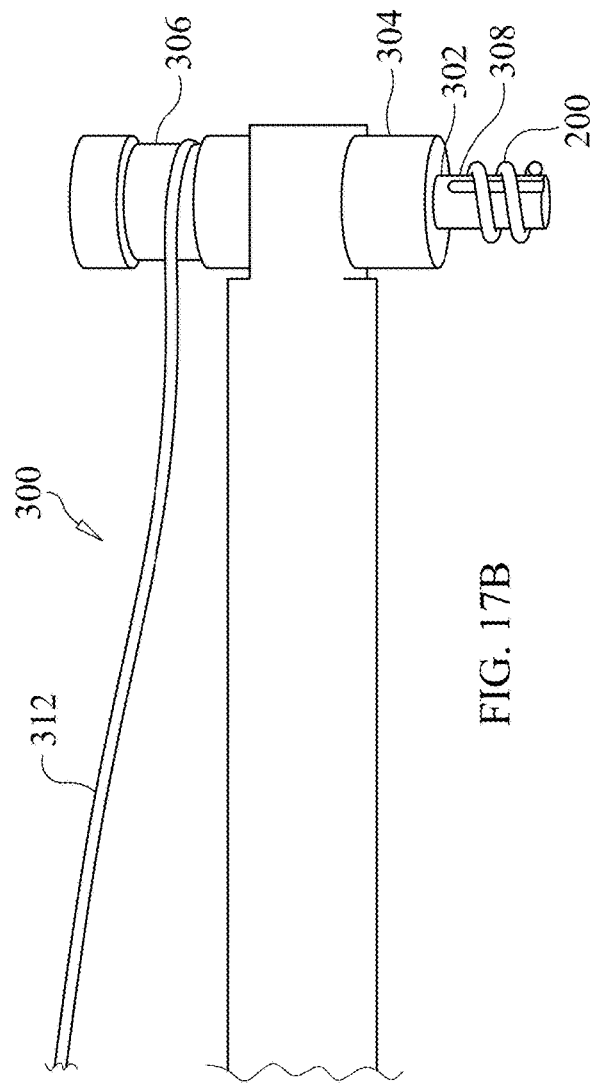
FIG. 17B is an enlarged view of a distal end portion of the driver of FIG. 17A.

FIG. 17A is a perspective view of a fixator driver 300 that can be used to anchor fixators in tissue to anchor components of the present invention, according to an embodiment of the present invention. Fixator driver 300 in the embodiment of FIG. 17A is particularly configured to drive surgical tacks 200. However, the driver 300 of FIG. 17A could be readily modified to drive screws or some other form of fixator 200. FIG. 17B is an enlarged view of an end effector formed as a distal end portion of the driver 300 of FIG. 17A. The end effector includes a shaft 302 that is rotationally mounted with respect to a head 304 and extends inferiorly therefrom. A spool 306 is integral with, or connected to shaft 302 for driving the shaft 302 as the spool 306 is rotated relative to the head 304. As shown the spool 306 extends superiorly of the head 304. A slot 308 is provided axially through a distal portion of the shaft 302. Slot 308 is configured and dimensioned to receive a proximal end portion 202 of the helical screw/surgical tack 200 (see FIG. 17E). The proximal end portion 202 functions as a cross bar that extends radially inwardly from the main body of the screw 200 so that when the shaft 302 is rotated with the screw 200 mounted of the shaft, it rotates the screw so as to drive it into the surgical target. Slot 308 has a length that is slightly less than the length of the fixator 200, so that when the proximal end portion 202 abuts the closed end of the slot, the sharp, distal end 204 of the fixator 200 extends beyond (inferior of) the free end of the shaft 302. This allows the operator of the driver 300 to use the driver 300 to stick the sharpened 204 into the surgical target (which may be tissue, sleeve, pad, etc.) to start the anchoring process, prior to rotating the fixator 200. The helical shape of the fixator 200 facilitates the fixator 200 to be drawn into the tissue/surgical target once the sharp end has pierced the target and then the fixator is subsequently rotated (clockwise, in the embodiment shown, although fixators may be alternatively designed to be installed with counter-clockwise rotation).

Figure 17C:
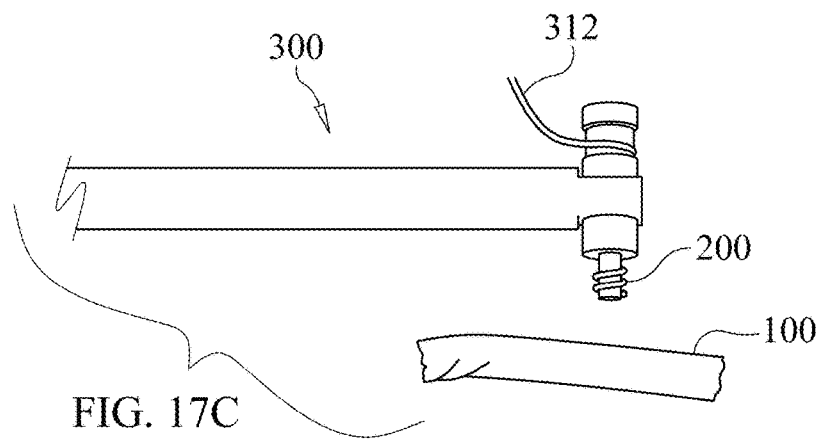
FIG. 17C illustrates the use of the fixator driver of FIGS. 17A-17B to anchor a sleeve with one or more fixators, according to an embodiment of the present invention.
Figure 17D:
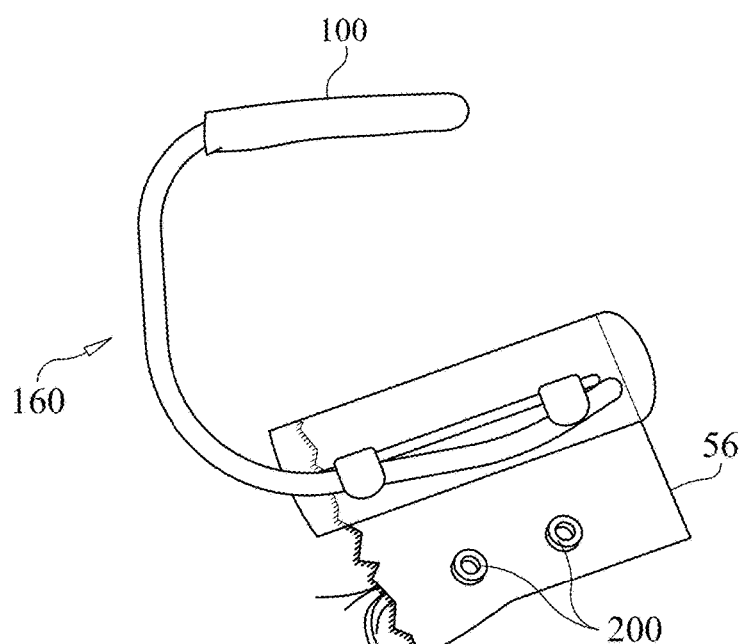
FIG. 17D illustrates a pair of helical screws having been installed through a pad to fix it to underlying material, such as cardiac tissue, according to an embodiment of the present invention.
Figure 17E:
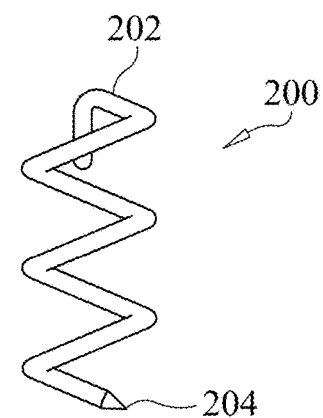
FIG. 17E illustrates a helical screw that can be used as a fixator according to an embodiment of the present invention.

The fixator driver 300 has a length sufficient to extend away from the heart when the shaft 302 of the end effector is contacting the heart at the transverse sinus or posterior wall of the left ventricle, by an amount that allows a user to readily grasp a proximal end portion of the elongate body 310 of the driver 300. Preferably the fixator driver 300 has a length sufficient to extend away from the heart when the shaft 302 of the end effector is contacting the heart at the transverse sinus or posterior wall of the left ventricle, by an amount that allows the proximal end portion of the elongate body 310 to extend out of the chest of the patient. A drive line 312, such as a cable, suture, thread or the like is configured to be wrapped around the spool 306 multiple times (up to 5, 10, 20, 30, 40 or more) and still have sufficient length to extend to the proximal end of the elongate body 310, and preferably beyond. The distal end of the drive line 312 may be attached to the spool but this is not necessary. By holding the elongate body 310 stationary and pulling on the drive line 312, this causes a driving rotation of the spool 306 and also the shaft 302 and fixator 200. The rotational driving drives the fixator 200 into the surgical target material and tissue and can be continued until the proximal end portion of the fixator is flush or nearly flush with whatever it is fixing. FIG. 17D illustrates a pair of helical screws 200 having been installed through a pad 56 to fix it to the underlying material, such as cardiac tissue. FIG. 17C illustrates the use of fixator driver 300 to anchor a sleeve 100 with one or more fixators 200. Though not specifically illustrated in FIG. 17C, the driver 300 can be used to anchor sleeve 100 in the transverse sinus, as described above with regard to FIGS. 5A-6.

When tacking/anchoring into the trigones 14T of the transverse sinus, it is desirable to insert the fixator as close to normal to the surface of the trigones 14T being anchored to as possible. It is not possible or at least very difficult to drive a fixator in a direction along a longitudinal axis of the driver and achieve the normal orientation desired, as the neck of head of the patient will typically obstruct the orientation that the driver needs to be placed at to achieve the normal orientation of the fixator 200 relative to the surface of the trigones/bottom of the transverse sinus. By configuring the end effector of the drive 300 to extend transverse (preferably perpendicular, but could be an angle ranging between 70 degrees and 110 degrees) to the longitudinal axis of the elongate body 300, this allows the operator to orient the fixator 200 normal to the trigones 14T at the bottom of the transverse sinus while the proximal end of the elongate body 300 is free to be manipulated and not obstructed by any patient body parts. Additionally, the end effector and distal end portion of the elongate shaft 310 can be slid into the transverse sinus to perform the anchoring functions.

Figure 18:
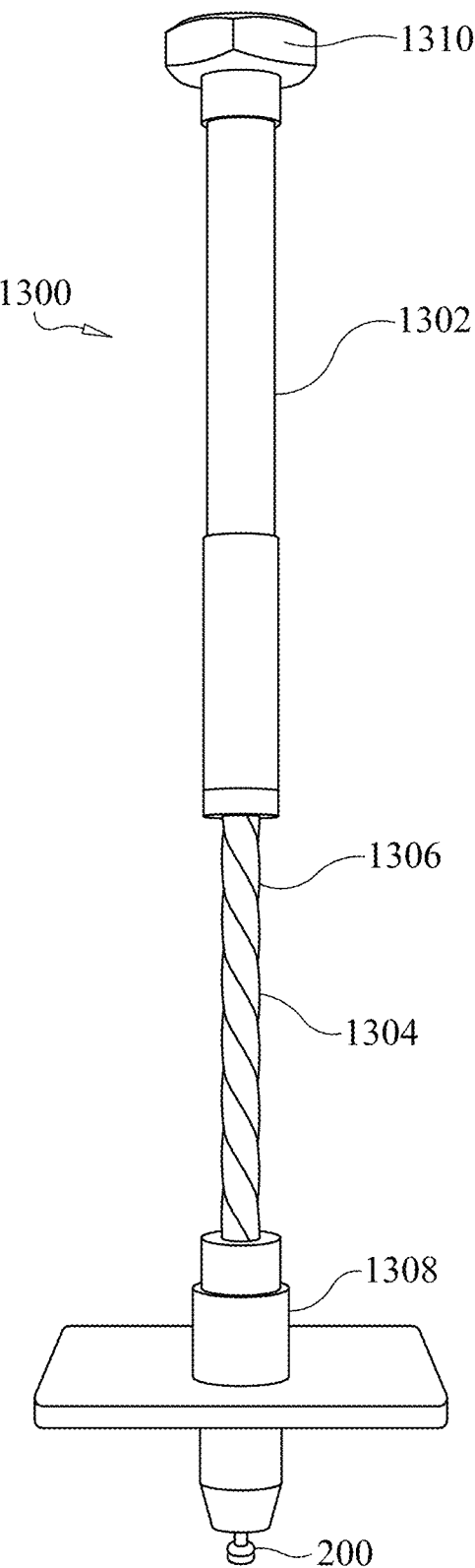
FIG. 18 is a plan view of a fixator driver according to another embodiment of the present invention.

FIG. 18 is a plan view of a fixator driver 1300 according to another embodiment of the present invention. Driver 1300 includes a handle and a shaft 1304 that includes helical threads 1306 that interface with a cam follower or mating threads (not shown). Shaft 1304 is fixed to, linked with or integral with head 1308. Fixator 200 is mounted to a distal end of the head 1308 as shown. By pressing down on the handle 1302 while grasping it and preventing it from rotating, this causes the shaft 1304 and head 1308 to rotate, thereby driving the fixator in rotation. The end of the handle 1302 may have an enlarged feature 1310 that facilitates pressing down on the driver 1300 to further enhance the driving function. The fixator 200 is releasably held by the head 1308 and is readily detached therefrom when it is anchored in a surgical site and the operator withdraws the drive 1300.

Figure 19:
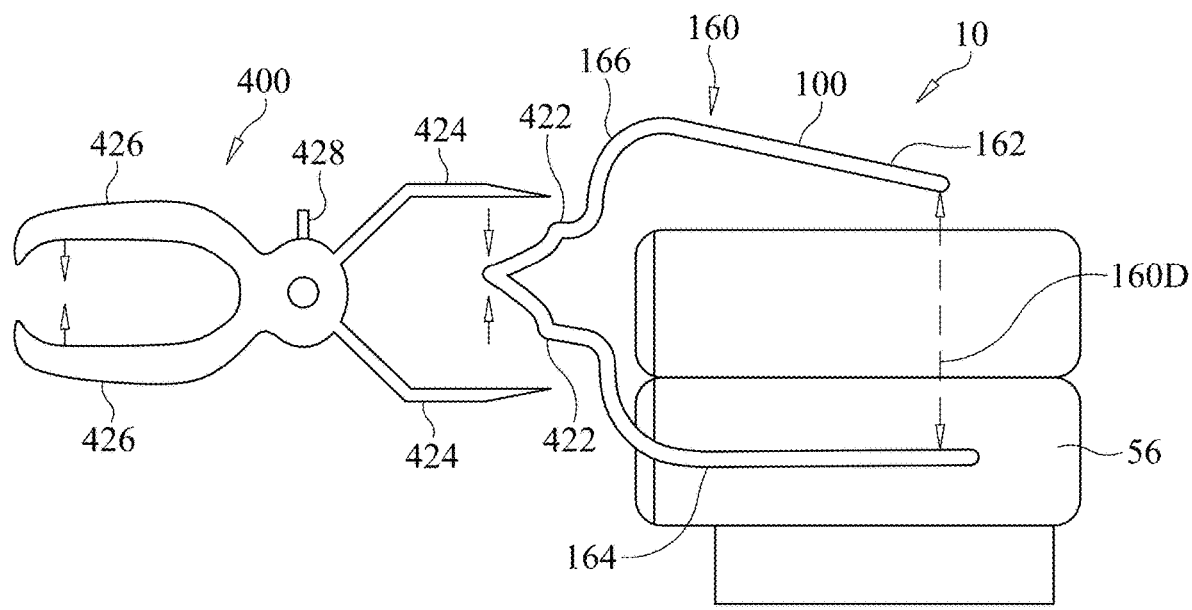
FIG. 19 illustrates use of a resizing tool on a main body of a device to change the distance between the contact surfaces of the anterior segment and posterior segment so as to change the amount of force applied to the surfaces of the heart, according to an embodiment of the present invention.

FIG. 19 illustrates use of a resizing tool 400 on a main body 160 of device 10 to change the distance between the contact surfaces of the anterior segment 162 and posterior segment 164 so as to change the amount of force applied to the surfaces of the heart. For example, in treatment of mitral regurgitation, in some cases it may be observed that installation of the device 10 as described herein results in reduction of mitral regurgitation, but it is determined that mitral regurgitation could be further reduced or eliminated if the forces applied to the mitral valve by the epicardial force application of the contact surfaces of the anterior and posterior segments 162, 164 could be increased. In such a case, resizing tool 400 is configured to engage the lateral segment 166 at locations where engagement features 422 are provided. The engagement features 422 may be bends in the lateral segment, as shown in FIG. 19 and/or loops, hooks or other features that can be engaged by the working ends of the arms 424 of the resizing tool 400. In the embodiment shown in FIG. 19, the operator squeezes the handles 426 toward one another to drive the arms 424 toward one another in the directions of the arrows shown. By contacting the working ends of the arms 424 against the contact features 422 of the anterior segment 166 and further squeezing the handles 426, the tool 400 can be operated to plastically deform the anterior segment so as to reduce the distance 160D between the contact surfaces of the anterior 162 and posterior 164 segments. This results in increased forces applied to whatever tissue is contacted between the anterior 162 and posterior 164 segments. The adjustments can be made more than once, if needed. Therefor an iterative process of force adjustment can be carried out until results achieved by the force application are optimized.

Figure 20:
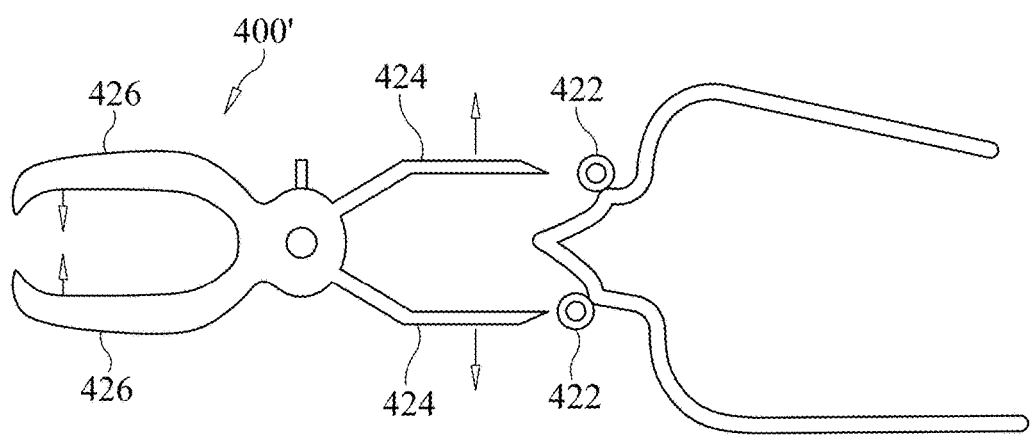
FIG. 20 illustrates a resizing tool applied to a main body of a device according to another embodiment of the present invention.

Tool 400 may be provided with a selector 428 that can be used to select whether the tool 400 is to be used to squeeze the lateral segment 166 or pull it further apart. The description already provided with regard to squeezing would be carried out to increase forces applied, as noted. By changing the selector to select a pulling apart action by the tool 400, the arms 424 are then driven apart when the operator squeezes the handles 426 together. Alternatively a pair of dedicated tools 400, 400' may be provided for performing squeezing and pulling apart operations, respectively. In either case, the engagement features 422 may include loops as shown in FIG. 20, or hooks, or other features that can the working ends of the arms 424 can gain purchase with to pull apart a portion of the lateral segment 166 so as to increase the distance 160D between the contact surfaces of the anterior 162 and posterior 164 segments. Although the tools 400, 400' can be used prior to implantation, they are designed for used post-implantation of the device 10, so that adjustments can be made to the implanted device 10 to optimize the forces applied thereby.

Figure 21:
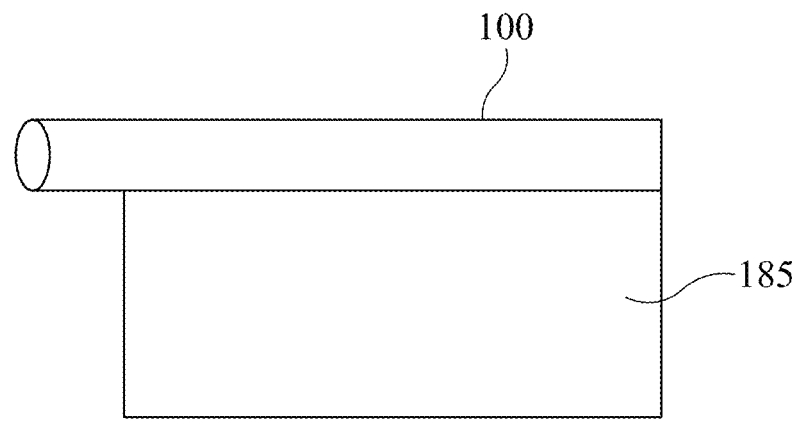
FIG. 21 illustrates a sleeve having a flap according to an embodiment of the present invention.

FIG. 21 is a plan view of a sleeve 100 according to another embodiment of the present invention. In this embodiment, sleeve 100 is provided with a flap 185 which may be made of the same material used to make flap 85 and/or sleeve 100. The flap 185 may function to allow tissue overgrowth. The flap 185 may be integral with or attached to sleeve 100. Flap 185 is provided for use in attaching or anchoring the sleeve 100 to a surgical target location. For example, when the anterior segment 162 of the device 10 is to be located in the transverse sinus, flap 185 may be anchored at the bottom of the transverse sinus (preferably into the trigones), to fix the sleeve 100 in place in the transverse sinus. Tacking, screwing or other types of anchoring described herein is performed through the flap 185 and into the target tissue, where the locations of the flap 185 through which the anchoring is performed are made as close to the sleeve 100 as possible, without passing through the sleeve 100.

Figure 22:
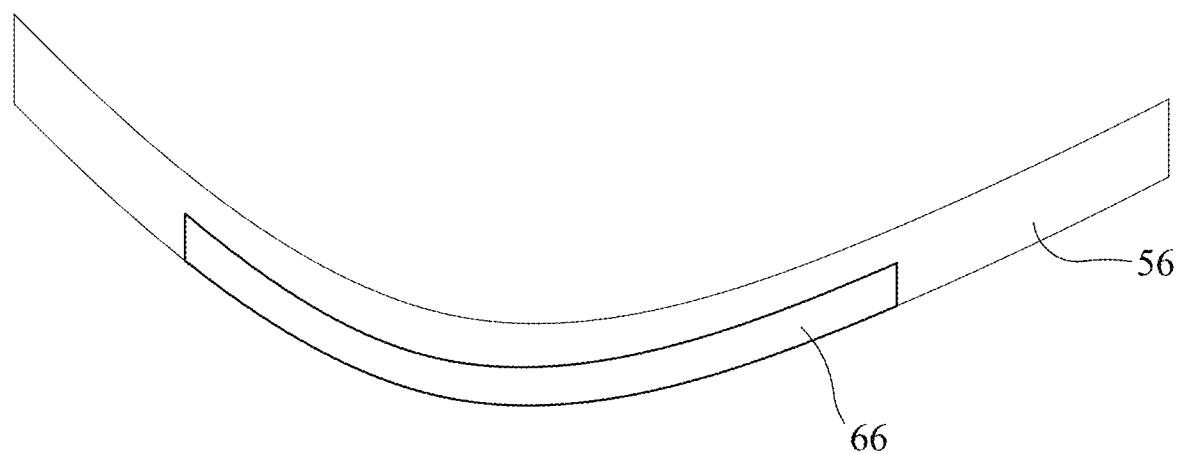
FIG. 22 is an illustration of a non-rigid hooked pad have a curved conformation according to an embodiment of the present invention.

FIG. 22 illustrates a pad 56 and engagement feature 66 that include a concave curvature such that the contact surface of the pad 56 curves in a direction along the longitudinal axis of the pad 56 (i.e., in a direction along which the posterior segment 164 will extend when it is attached to the engagement feature 66). As the pad 56 is typically made of flexible material, it can be molded or otherwise made as a flat pad, without the curvature described. The engagement feature 66 in FIG. 22 is an elongated hooked member. Engagement feature 66 is formed of a rigid material such as stainless steel, titanium, rigid polymer or the like. Accordingly the engagement feature is formed with the curve shown so as to match the curvature of the posterior segment 164 that it is designed to be connected to. The engagement feature 66 can then be slid into a pocked in the pad 56 so that the hooked portion extends out of the pocket, or glued or welded or otherwise fixed to the pad 56, at which time the pad 56 also takes on the curvature of the engagement feature 66. Alternatively, the pad 56 can be over-molded on the engagement feature 66 and will exhibit the same curvature as the engagement feature 66.

Figure 23A:
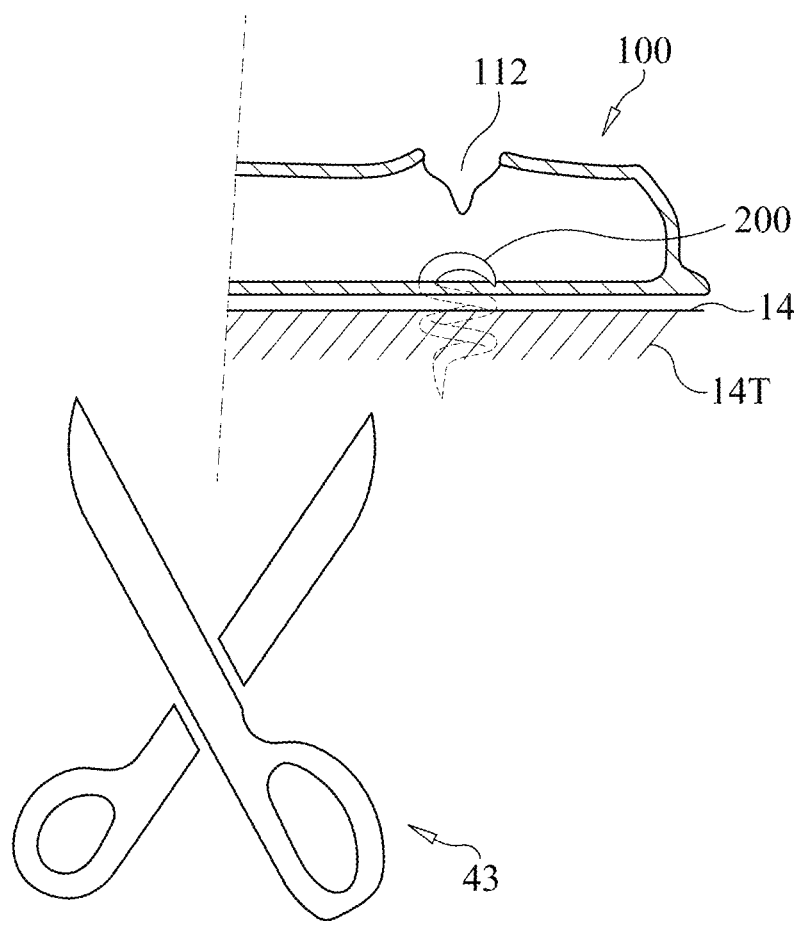
FIG. 23A is an illustration of a sheath being cut to length, according to an embodiment of the present invention.

As noted above, the usable length of the transverse sinus 112 to be occupied by the anterior segment 162 varies among patients. Even with the provision of several lengths of sleeve 100, the ideal length of a sleeve 100 for a best fit in a particular transverse sinus 112 may be different from any of the precut lengths that are available. FIG. 23A illustrates that sleeve 100 may be cut to an optimized length using a cutting instrument 413, such as scissors, knife, scalpel or other cutting instrument. As indicated in FIG. 23A the cutting of the sleeve 100 to a desired length can be performed after anchoring the sleeve at the surgical target location (e.g., in the transverse sinus). Alternatively the sleeve 100 can be cut to the desired length prior to implanting it, if the optimum length is already known or able to be determined prior to implanting the sleeve 100. Further alternatively, the sleeve may be slid over the anterior segment 162 of the device 10 prior to implantation to measure the desired length of the sleeve 100 that covers the anterior segment 162, but does not extend beyond it. The sleeve 100 can then be removed from the anterior segment and cut to the measured, desired length. The usable length of the transverse sinus 14 for receiving the anterior segment is generally defined over a length from the left atrial appendage to the end of the left atrium between the aorta and the mitral valve. Where the left atrium ends and transitions to the right side of the heart, the transverse sinus jogs to the left. This typically marks the end of the usable length of the transverse sinus, as it is not acceptable for the anterior segment to abut or intersect with the tricuspid valve or the right atrium.

Figures 23B, 23C, 23D:
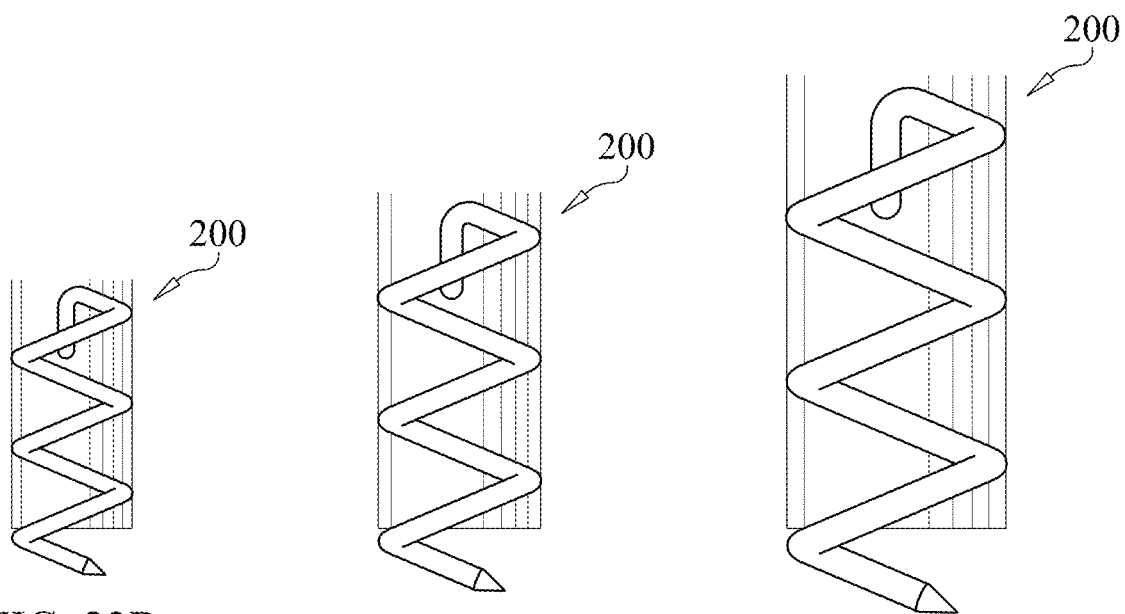
FIGS. 23B-23D illustrate different sized fixators that may be used according to embodiments of the present invention.

A variety of fixator 200 sizes may be provided for use in anchoring components of the present invention to surgical target locations. For example, when using helical screws as fixators 200, helical screws may be provided in sizes of 5 mm diameter, 4 mm diameter and 3 mm diameter, see FIGS. 23D-23B, respectively. Helical screws having 5 mm diameter are a standard size used by typical helical screw drivers. For certain applications however, such as in the transverse sinus, it may be desirable to use smaller helical screws 200 for anchoring, such as 4 mm diameter or 3 mm diameter, or helical screws having a diameter in the range from 2.5 mm to 5 mm, such as, but not limited to: 2.5 mm, 2.75 mm, 3.25 mm, 3.5 mm, 3.75 mm, 4.25 mm, 4.5 mm or 4.75 mm.

Figure 24:
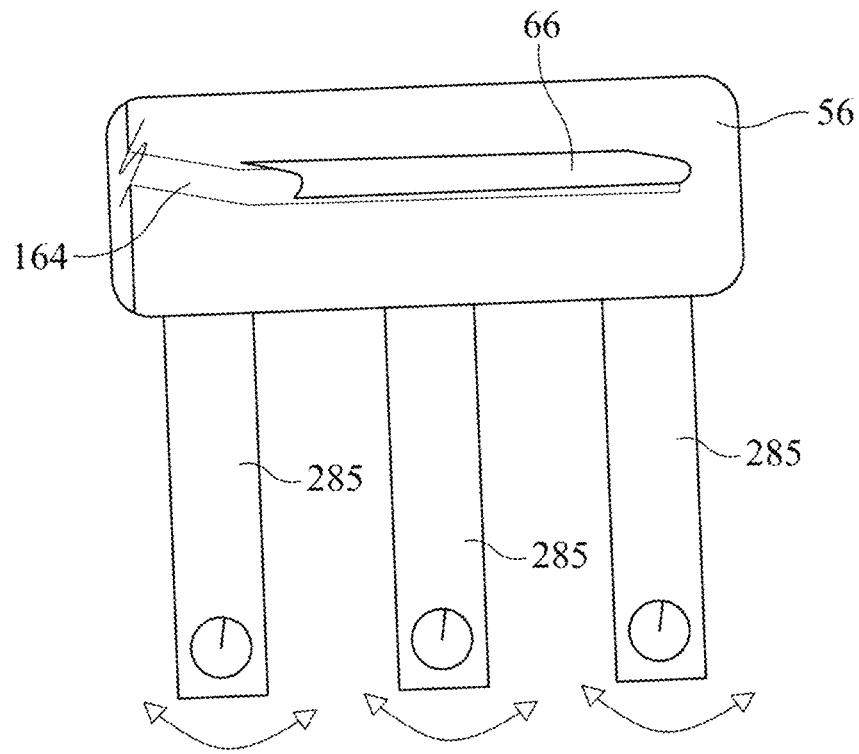
FIG. 24 illustrates a pad having adjustable flaps, according to an embodiment of the present invention.

FIG. 24 illustrates a pad 56 having a plurality of individually positionable flaps 285. In contrast to the large single flap 85 described with regard to FIG. 1B, for example, the provision of multiple, smaller width flaps 185 allows these flaps to be rotated or otherwise changed in position relative to the positions that they occupy in FIG. 24. This illustrated by the arrows in FIG. 24. Thus one or more flaps can be rotated or shifted somewhat to avoid attachment to an underlying blood vessel, for example, or other feature that is undesirable to anchor to. Although FIG. 24 shows three individually positionable flaps 285, the present invention is not limited to this number, as two, or more than three positionable flaps 285 could be used. Although not preferred, even one positionable flap 285 could be used that is sufficiently narrow to allow it to be rotated or otherwise repositioned. It is preferred to use a plurality of flaps 285 for better securement.

Figure 25:
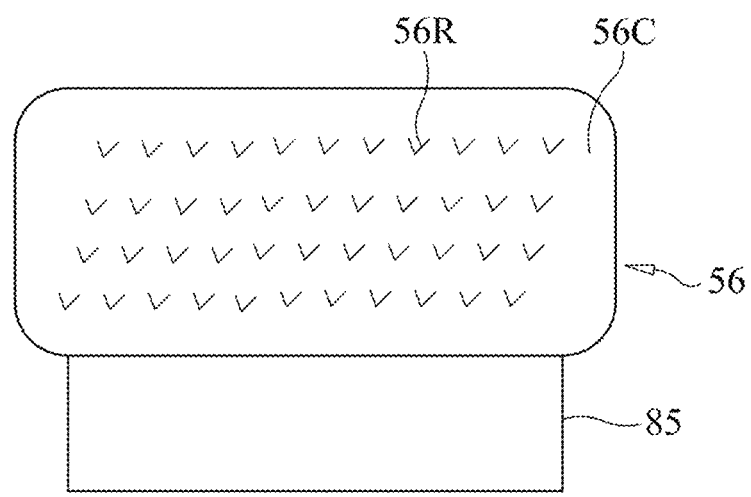
FIG. 25 illustrates a pad having a roughened surface according to an embodiment of the present invention.

FIG. 25 illustrates an embodiment of a pad 56 having a roughened contact surface 56c according to an embodiment of the present invention. By providing a roughened contact surface 56c, this increases the friction of the pad relative to the tissue that it is being anchored to (e.g., posterior, epicardial surface of the left ventricle). By increasing the friction, this increases the stability of the positioning of the pad 56 relative to the underlying tissue, so that it is less likely to move during the anchoring process. Thus, helical screws or other fixators can be used to attach the flap 85 to the underlying tissue with less risk of the pad 56 (and the flap 85) moving during the attachment. Optionally the flap 85 may also be provided with a roughened contact surface. The surface roughness may include roughness features, such as hooks, corrugations, suction cups, embedded threads, or other raised features. Further alternatively or additionally, roughness features could be molded into the contact surface, sprayed on, or formed by abrasion.

Figure 26:
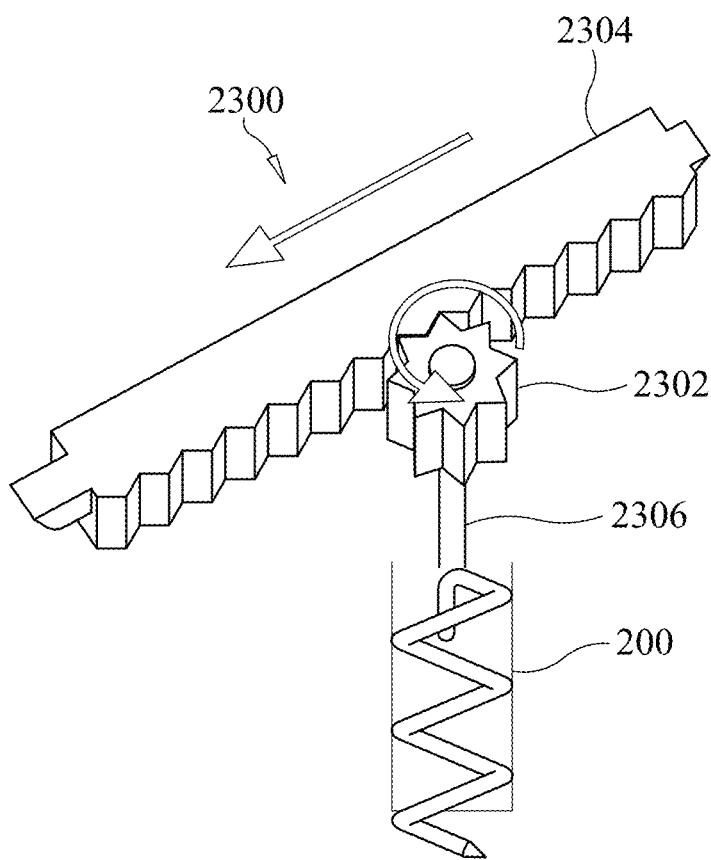
FIG. 26 illustrates a rack and pinion mechanism used as a driving mechanism of a fixator driver, according to an embodiment of the present invention.

FIG. 26 illustrates an alternative driving mechanism 2300 to those shown in FIGS. 17 and 18, which can be used to drive fixators 200 to anchor components of a device 10 according to an embodiment of the present invention. A rack 2304 and pinion 2302 mechanism is provided to convert a translational motion of the rack 2340 to rotational motion of the pinion 2302. The pinion gear 2302 has a shaft extending therefrom that is configured to releasably hold a fixator 200, similar to or the same as that described with regard to FIG. 17B. Accordingly, this arrangement can advantageously be used to drive a fixator in a direction normal to the direction of the applied force and therefor can be used to drive fixators 200 to anchor a sleeve 100 in a transverse sinus 14, for example.

Figure 27A:
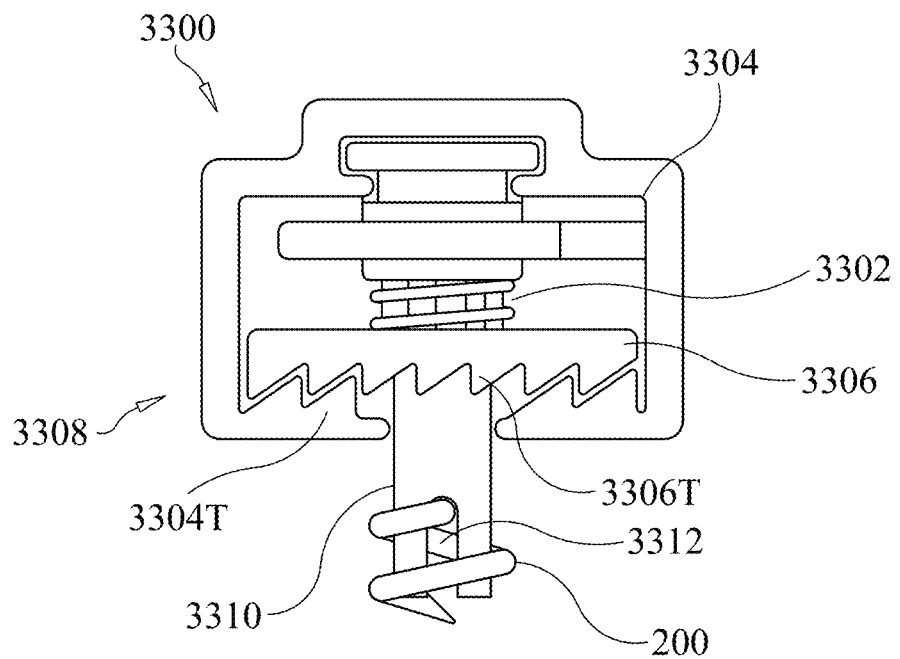
FIGS. 27A-27I illustrate a driving mechanism of a fixator driver that includes a constant force spring with a dampener and ratchet that can be activated with a force against the tacker instrument, according to an embodiment of the present invention.

FIG. 27A schematically illustrates a fixator driver 3300 according to another embodiment of the present invention.

In this embodiment, the driver includes constant force spring 3302 that is fixed relative to the main body 3304 of the driver 3300 at one end, and that is connected to a flywheel 3306 at the other end. The flywheel 3306 mechanically engages the main body 3304 via a one-way ratchet mechanism 3308 when in non-firing configuration as illustrated in FIG. 27A, where mating ratchet teeth 3306T, 3304T on the flywheel 3306 and main body 3304 respectively matingly engage to prevent rotation of the flywheel 3306 relative to the main body 3304 in one rotational direction. A shaft 3310 extending distally from the flywheel 3306 is integral with the flywheel 3306 or otherwise mechanically linked so as to be driven in rotation when the flywheel 306 rotates. Shaft 3310 includes a slot 3312 configured in the same manner as described above with regard to slot 308 (see FIG. 17B), for releasably holding a fixator 200.

Figure 27C:
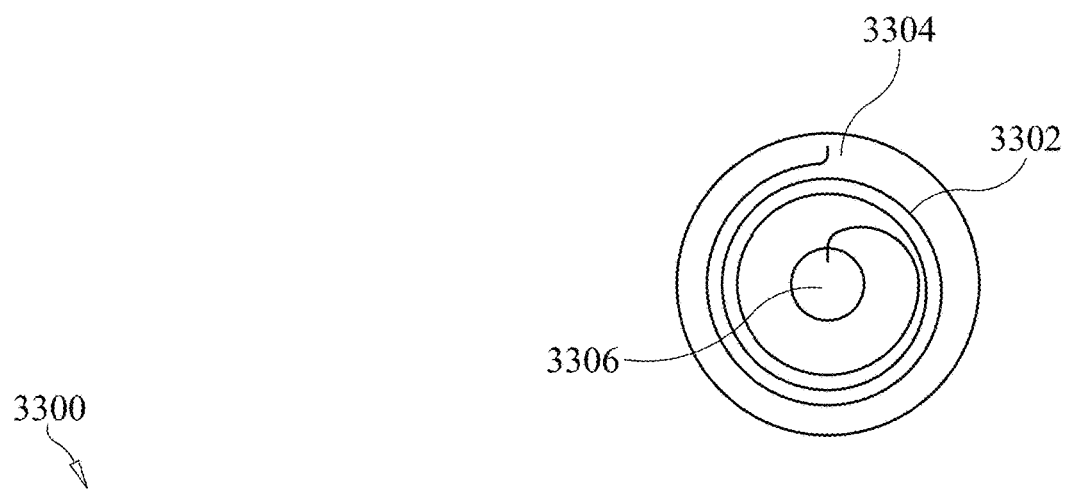
Figure 27B:
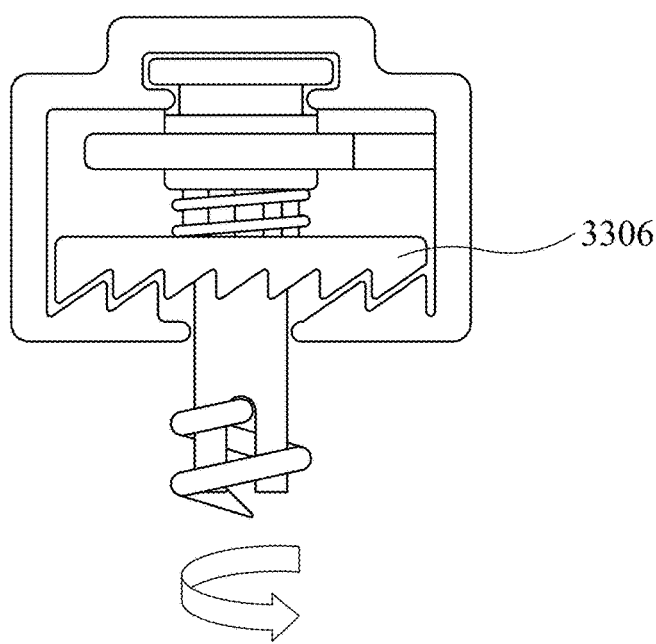
Figure 27D:
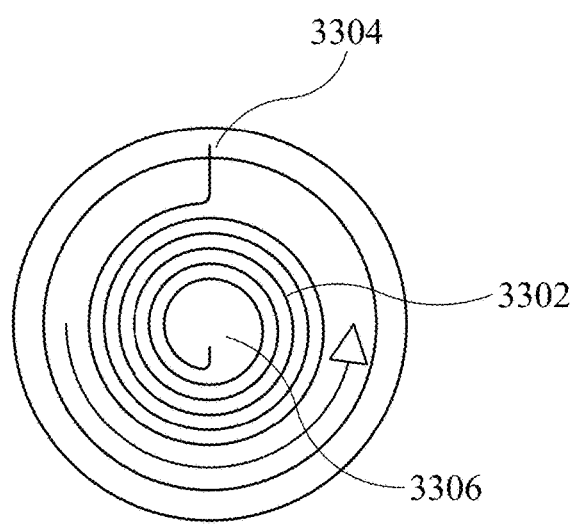

Spring 3302 can be wound by rotation of flywheel 3306 in the rotational direction that is not prevented by the one way ratchet mechanism 3308, which is the direction of rotation indicated by the arrows in FIGS. 27B and 27D. With each wind, the tension built up in the spring 3302 is maintained as the one-way ratchet mechanism 3308 prevents counter-rotation of the flywheel 3306 relative to the main body 3304 each time the winding force is released. FIG. 27C schematically illustrates the spring 3302 in an unwound state during which the spring 3302 stores the least amount of tension. FIG. 27D illustrates the spring 3302 in a wound state, wherein the spring 3302 is fully wound and stores potential energy ready to be released and converted to kinetic energy as it drives the flywheel 3306.

Figure 27E:
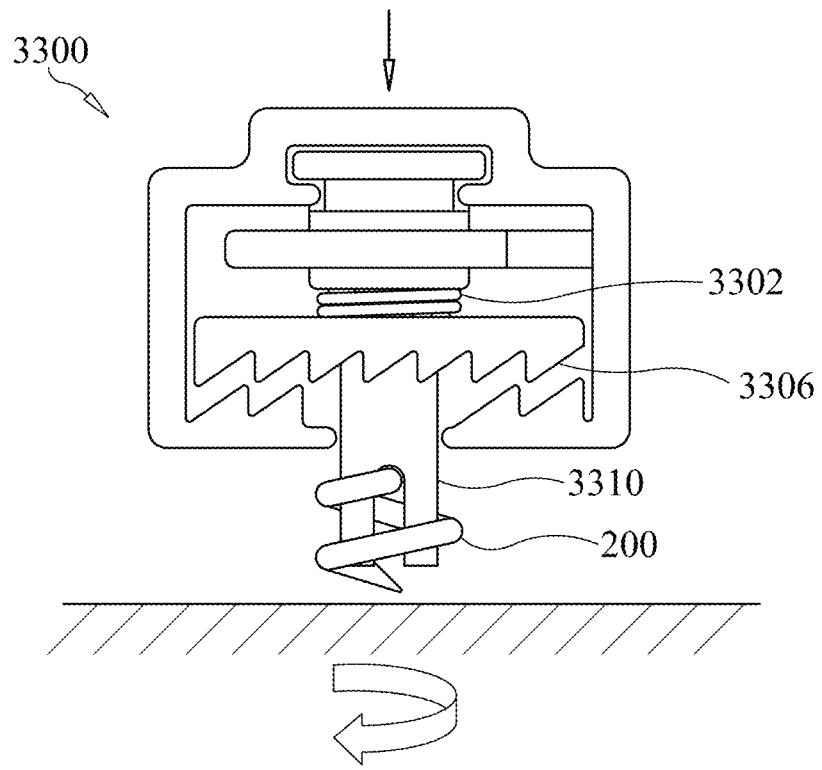
Figure 27F:
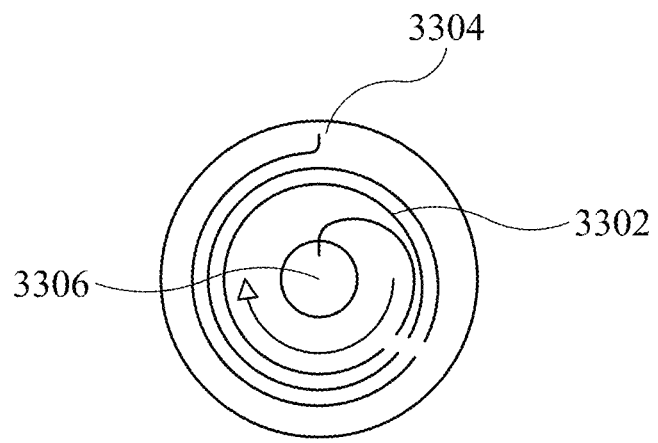

FIG. 27E illustrates a firing or deployment of the fixator driver 3300. Upon contacting the distal tip of the fixator 200 and distal end of the shaft 3310 against the target into which the fixator 200 is to be deployed, the compressive force established by the contact force and the opposing force from the target being contacted (see arrows) forces the mating teeth 3306T, 3304T apart, freeing the flywheel 3306 at which time the tension in the spring 3302 is released thereby driving the flywheel 3306, shaft 3310 and fixator 200 in rotation in the direction of the rotational arrow shown in FIG. 27E, resulting in driving the fixator 200 into the target and release of the fixator 200 from the shaft 3310, slot 3312. FIG. 27F schematically illustrates the spring 3302 unwinding from the wound state shown in FIG. 27D back toward the fully unwound state shown in FIG. 27C as the spring unwinds in the direction of the rotational arrow shown during firing/deployment. By using a constant force spring, a constant rotational force is provided to the fixator 200 through the flywheel 3306 and shaft 3310 throughout the deployment and anchoring of the fixator 200.

Figure 27G:
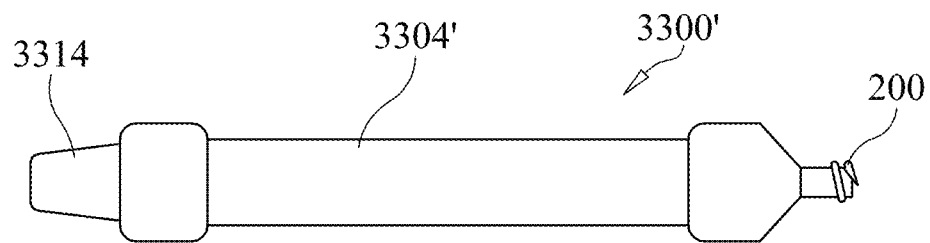
Figure 27H:
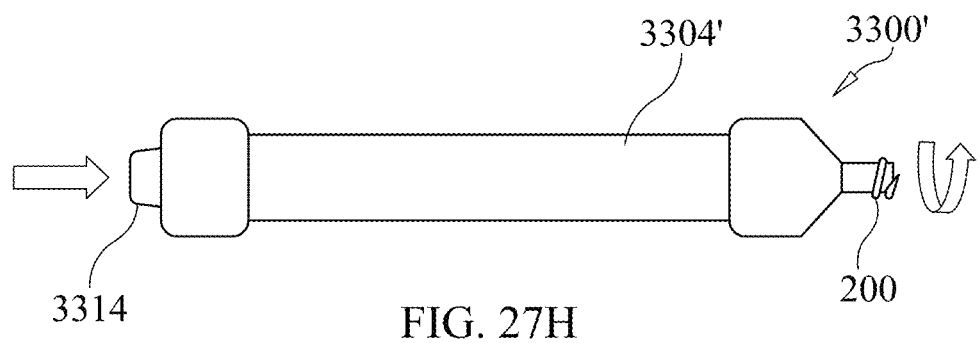

FIGS. 27G-27H show a variant 3300' of the fixator driver 3300 of FIG. 27A. Fixator driver 3300' includes the same driving mechanism as described above with regard to FIGS. 27A-27F, and therefor operates in the same manner, except that driver 3300' is provided with an actuator 3314 such as a push button or other actuating mechanism that is mechanically linked to separate the mating teeth 3306T, 3304T apart when the actuator is actuated. FIG. 27G illustrates the actuator in a non-deployed state and FIG. 27H illustrates a deployment or firing of the actuator 3314. In the case of the push button, the operator presses the push-button toward the main body 3304' to fire the driver 3300 and install the fixator 200.

Figure 27I:
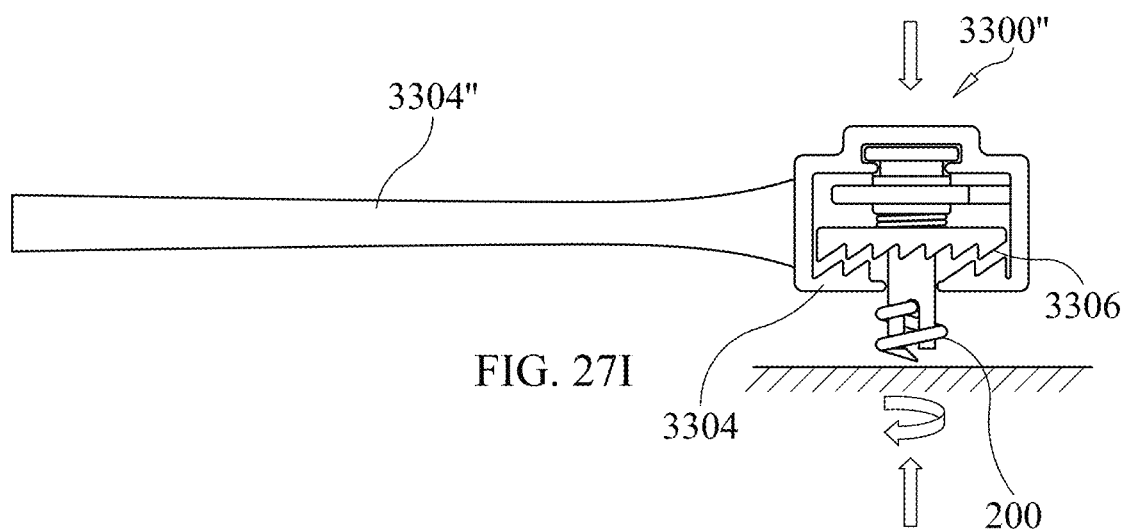

Although the driver 3300 is shown and described as being configured to drive the fixator 200 in a direction along the longitudinal axis of the main body 3304, it is noted that this embodiment can be modified so as to drive the fixator in a direction normal to the longitudinal axis of the device. Such arrangements would be advantageous for driving fixators 200 in the transverse sinus for example. FIG. 27I illustrates a variant 3300'' of the driver 3300 in which an elongate handle 3304'' extends normally from the housing 3304 such that the longitudinal axis of the instrument 3300'' is normal to the direction of deployment of the fixator 200. It is noted that the variant 3300' of FIGS. 27G-27H could also be modified so as to deploy the fixator 200 in a direction normal to the longitudinal axis of the instrument 3300'.

Figure 28A:
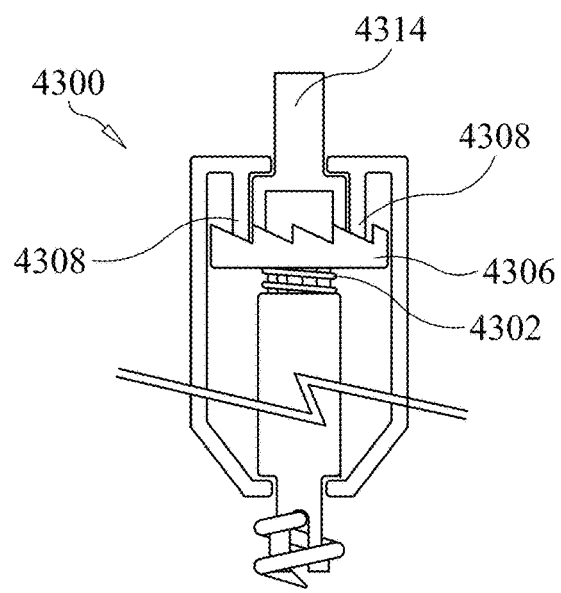
FIGS. 28A-28D illustrate a driving mechanism of a fixator driver that includes a biased cam with a spring that forces rotation in one direction, according to an embodiment of the present invention.
Figure 28B:
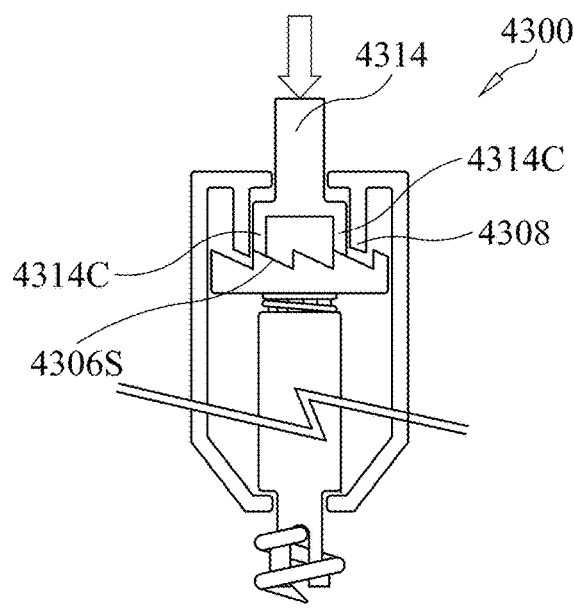
Figure 28C:
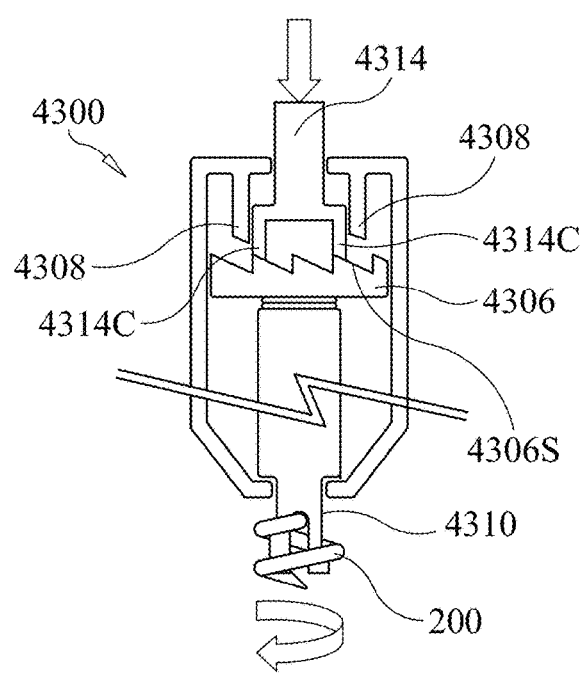
Figure 28D:
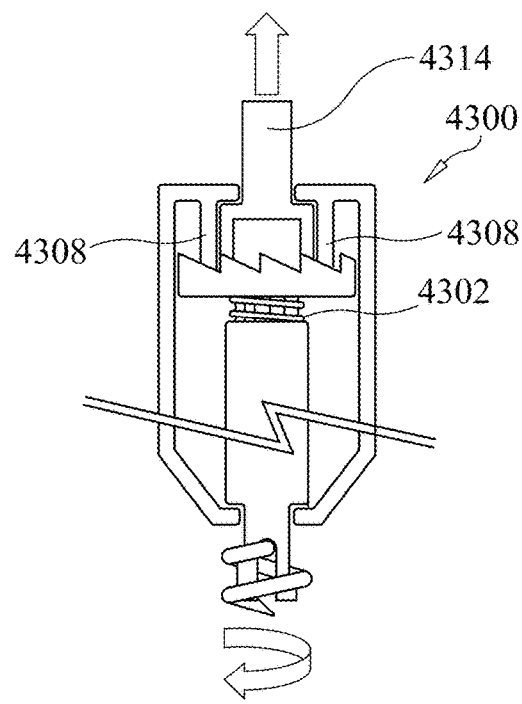

FIGS. 28A-28D schematically illustrate fixator driver 4300 according to an embodiment of the present invention. In this embodiment, a biased cam 3406 is biased by a spring 4306 that biases it into engagement with one or more stop members 4308 that are fixed relative to the main body 4304 of the driver 4300. An actuator 4314 is provided that, upon actuation (e.g., depressing in the direction of the arrow in FIG. 28B, although actuators having other types of actuation motions could be substituted) moves the cam surfaces 4306S of the cam 4306 away from (FIG. 28B) and out of engagement with (FIG. 28C) the stops 4308. Additionally, during this deployment or firing action, cam followers at the distal end of the actuator 4314 engage the cam surfaces 4306S and force rotation of the cam 4306 in the direction of the arrow in FIG. 28C. This consequently drives the fixator 200 in the same rotational direction with the rotational force provided through the shaft 4310 to the fixator 200. Release of the actuator as illustrated in FIG. 28D results in the spring 4302 driving the cam 4306 back into engagement with the stops 4308. Repeated actuation and release of actuator 4314 therefore incrementally rotates the fixator 200 with each cycle of actuation and release.

Figure 29:
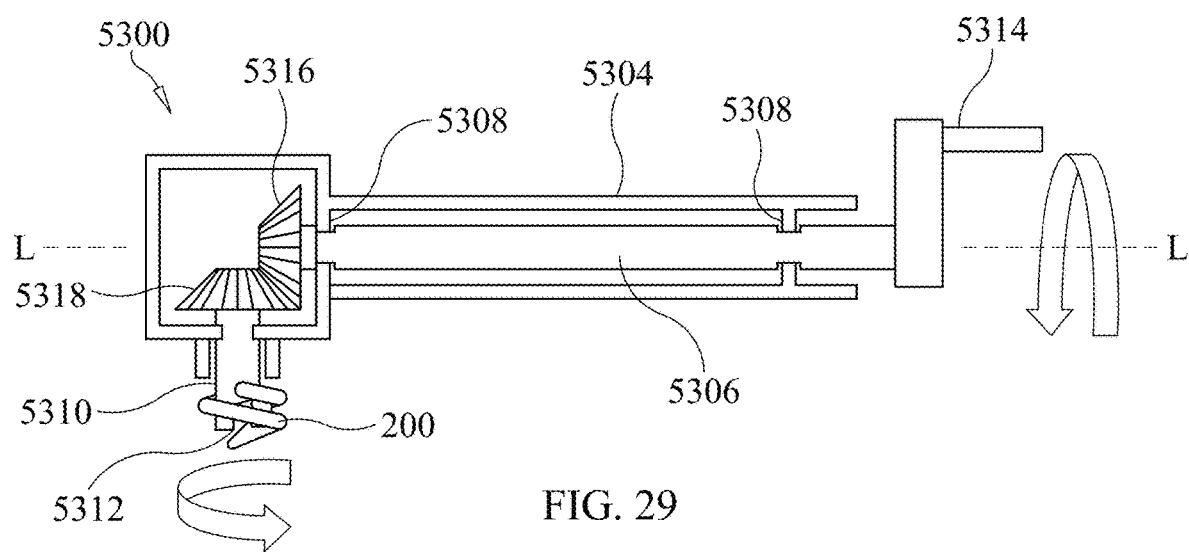
FIG. 29 illustrates a fixator driver having a right angle gear, according to an embodiment of the present invention.

FIG. 29 schematically illustrates a fixator driver 5300 according to an embodiment of the present invention. In this embodiment the drive mechanism is configured to drive the fixator 200 in a direction normal to the longitudinal axis L-L of the driver 5300. An actuator 5314 such as crank or other handle configured to deliver a rotational action is connected to a first shaft 5306 extending along the longitudinal axis within the main body 5304. First shaft 5306 is mounted for rotation relative to the main body 5304, such as by bearings 5308 or the like. A second shaft 5310 extends normally to the longitudinal axis L-L and is provided with a slot 5312 for releasably holding a fixator 200, such as in a manner already previously described with regard to earlier described slots. A first bevel gear 5316 mounted at a distal end of the first shaft 5306 meshes with a second bevel gear 5318 mounted at a proximal end of the second shaft 5310, thereby forming a drive train for driving the fixator 200 with device 5300. The driving of the fixator 200 is carried out by holding the main body 5304 stationary and cranking (rotating) the actuator 5314 which rotates the shaft 5306. Rotation of the shaft 5306 is translated to rotation of the shaft 5310 and fixator 200 by the interaction between the bevel gears 5316, 5318.

Figure 30:
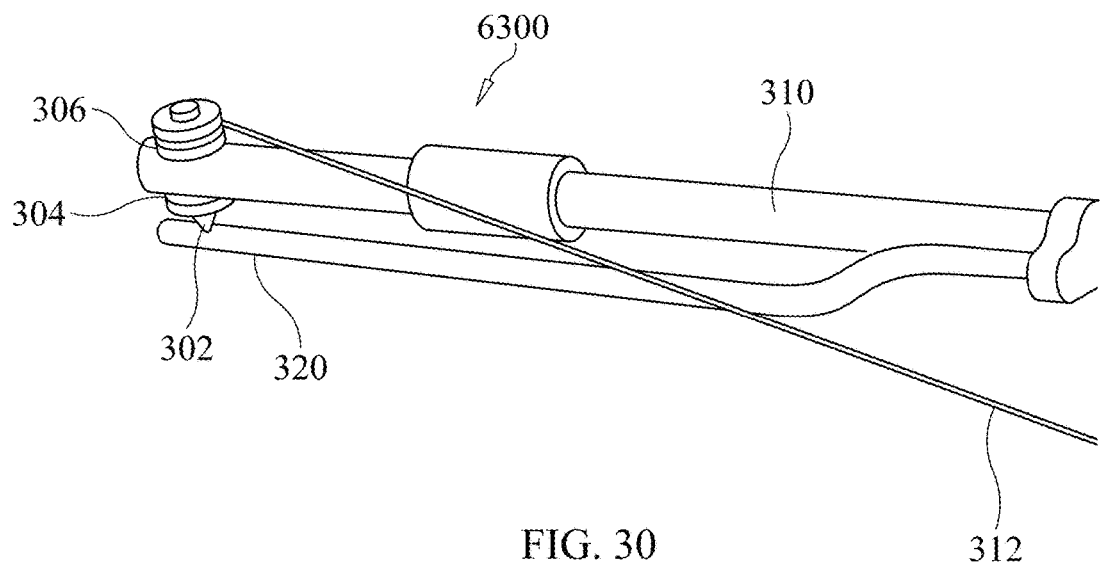
FIG. 30 illustrates a fixator driver having a guide for a sleeve, according to an embodiment of the present invention.
Figure 31:
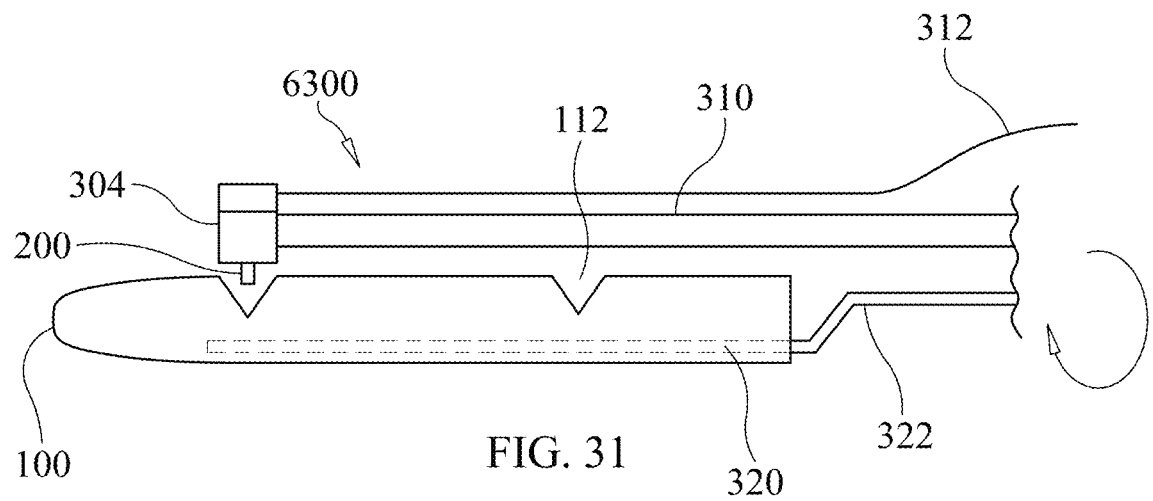
FIG. 31 illustrates insertion of the guide arm of FIG. 30 into a sleeve 100, according to an embodiment of the present invention.
Figure 32:
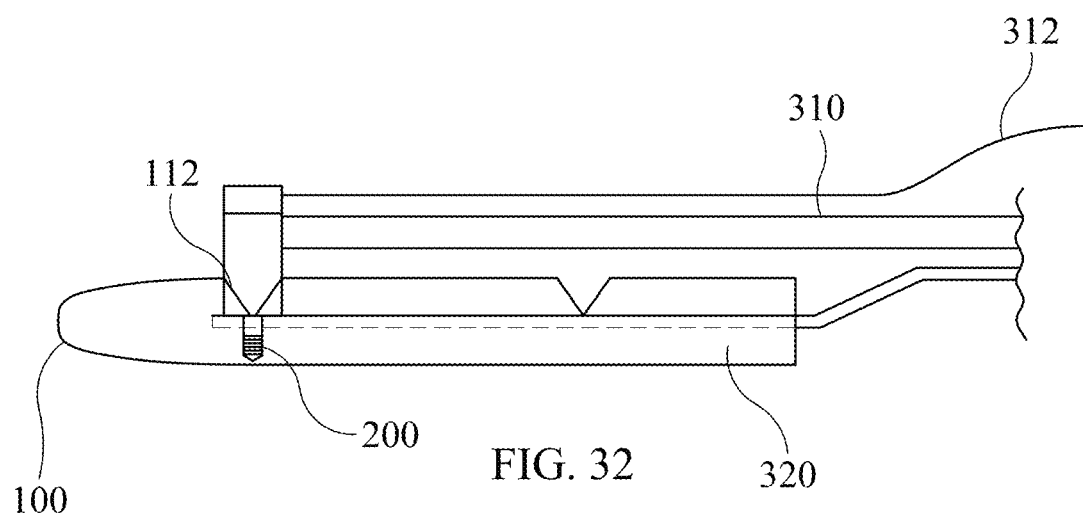
FIG. 32 illustrates drawing a distal end portion of a guide arm nearer to the driver main body by rotating the proximal end portion of the guide arm, according to an embodiment of the present invention.
Figure 33:
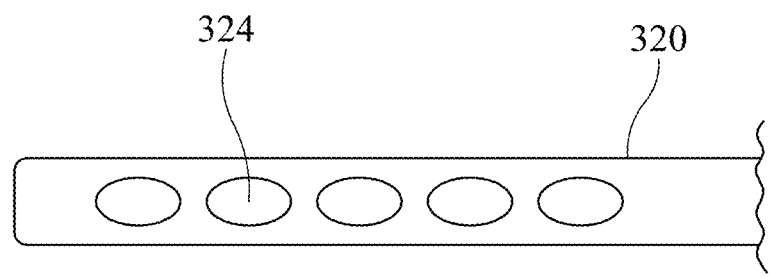
FIG. 33 illustrates providing through holes through a guide arm, according to an embodiment of the present invention.

FIG. 30 illustrates a variant 6300 of the fixator driver 300 of FIGS. 17A-17C. All of the component of the driver 300 described above are the same in driver 6300 and are therefore not described here. In addition to what is provided in fixator driver 300, fixator driver 6300 further includes a guide arm 320 configured to be received in a sleeve 100. Guide arm 320 can be positioned in sleeve 100 to hold it stationary while the flap 185 of FIG. 21 is being anchored to the surgical target site, such as the transverse sinus, for example. Alternatively, the guide arm 320 can be inserted into the sleeve 100 for a procedure in which the sleeve 100 is anchored to the surgical target. FIG. 31 illustrates the insertion of the guide arm 320 into the sleeve 100. Once the head 304 has been positioned in the desired location for delivery of the fixator through the bottom wall of the sleeve 100, the guide arm 320 can be rotated by the operator, as illustrated by the rotational arrow in FIG. 31. The guide arm 320 includes a pair of bends 322 that offsets the distal end portion of the guide arm 320 from the head 304 and fixator 200 when the distal end portion of the guide arm 320 is aligned with the axis of the head 304 and shaft 320. Upon rotating the proximal end portion of the guide arm 200, this draws the distal end portion of the guide arm 200 nearer to the driver main body 310 and also out of alignment with the fixator 200 and shaft 302, drawing the fixator 200 and shaft 302 into the sleeve 100 through slit 112, as illustrated in FIG. 32. The fixator can next be driven through the bottom wall of the sleeve 100 while the sleeve 100 is held from moving by the guide arm 200. Alternatively, the guide arm could be modified to hold the sleeve while in alignment with the shaft 302 and fixator 200 by providing one or more through holes 324 through the guide arm 200, as illustrated in FIG. 33. Additionally, in all variants the guide arm 320 is slidably mounted relative to the main body 310, in slide mount 326 (see FIG. 30), which may be a journal, sleeve, or other mount that allows the guide arm 320 to slide relative to the main body 310 in a direction of the longitudinal axis of the main body 310. This allows the guide arm 320 to be inserted into the full length of the sleeve 100 and maintain its position there as the head 304 is being drawn back from a first location to a second location to permit multiple fixators 200 to be anchored at multiple locations along the sleeve 100. In another variant, two guide arms 320 can be provided side by side and configured so that the fixators 200 can be driven through a space between the guide arms 320.

Figure 34A:
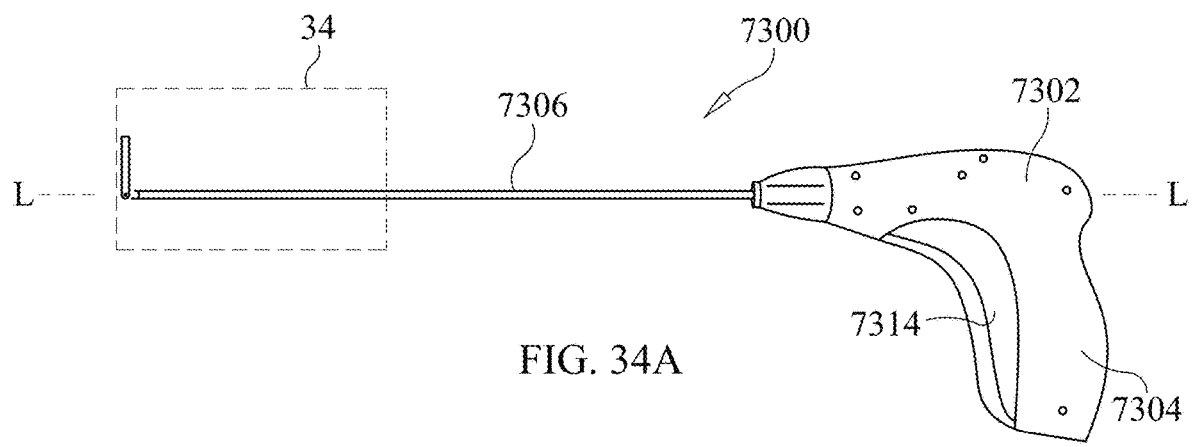
FIG. 34A shows a fixator driver according to an embodiment of the present invention.
Figure 34B:
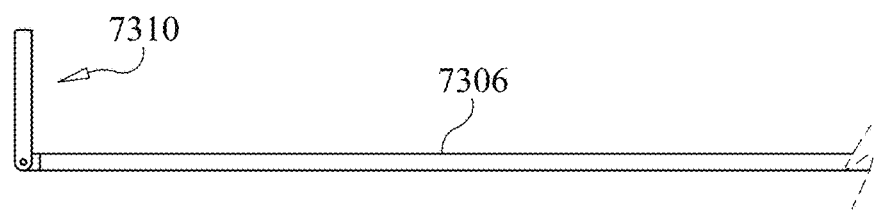
FIG. 34B illustrates a right angle configuration of a cartridge of the fixator driver of FIG. 34A.

FIG. 34A shows fixator driver 7300 according to an embodiment of the present invention. In this embodiment the drive mechanism is configured to drive the fixator 200 in a direction normal to the longitudinal axis L-L of the driver 7300. The driver 7300 includes a housing 7302 that includes a hand grip 7304 and an actuator 7314 and which houses a drive mechanism for the driver. The drive mechanism may include an electric motor, either battery powered or powered by an external power source, or may be a manually driven mechanism that can be driven by repeatedly squeezing the actuator, similar to the actuation of driver 4300 for example. The motorized version is preferred. A drive shaft 7308 extends through the main shaft 7306 of the drive 7300 and interfaces with a receiver 7312 formed at a proximal end of a removable, reloadable fixator cartridge 7310. FIG. 34B illustrates the right angle configuration of the cartridge 7310, which is designed to translation the rotary driving motion of the drive shaft 7308 along the longitudinal axis L-L to a rotary driving motion normal to the longitudinal axis.

Figure 34C:
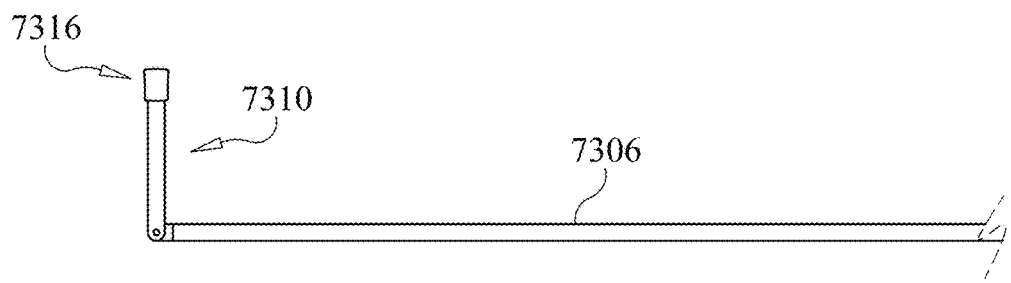
FIG. 34C illustrates an optional deflectable or atraumatic tip that may be provided at the distal end of the cartridge of FIG. 34B.
Figure 34D:
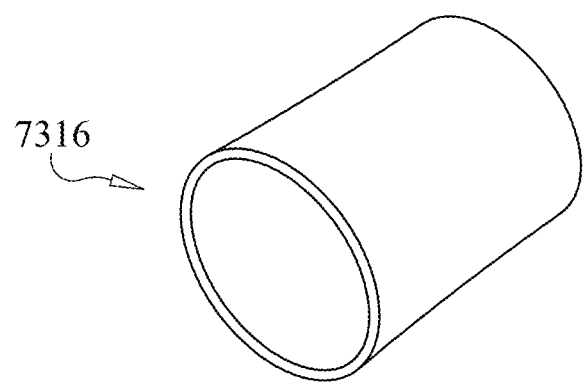
FIG. 34D shows an enlarged, isolated view of the deflectable tip of FIG. 34C.
Figure 34E:
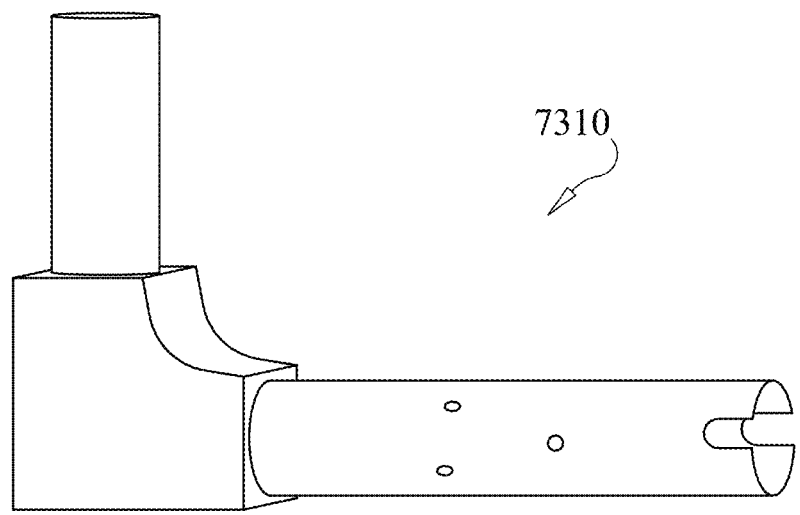
FIG. 34E is an isolated view of a cartridge according to an embodiment of the present invention.

FIG. 34C illustrates an optional deflectable or atraumatic tip 7316 that may be provided at the distal end of the cartridge 7310. The deflectable tip 7316 helps reduce the risk of trauma to tissues contacted by the distal end of the cartridge 7310. Additionally, the deflectability of the tip 7316 increases the surface area connection between the tip and the target as it deflects, thereby providing more protection from contamination of or interference with the fixator 200 as it is being driven. FIG. 34D shows an enlarged, isolated view of the deflectable tip 7316. The deflectable tip 7316 may be made of silicone or other elastic and or flexible biopolymer. FIG. 34E shows an isolated view of the cartridge 7310 according to an embodiment of the present invention.

Figure 34F:
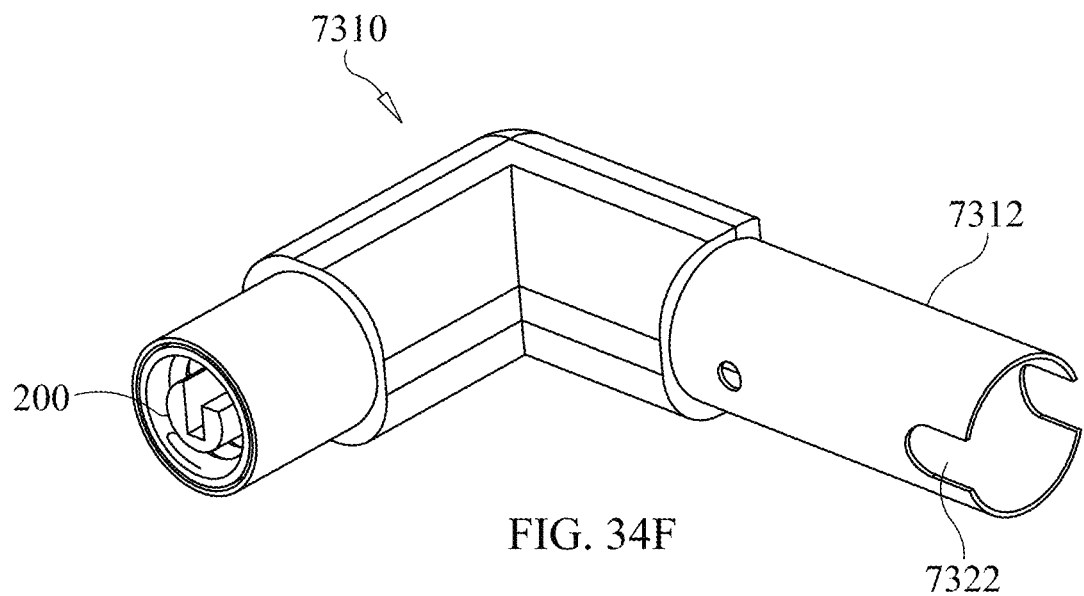
FIG. 34F shows notches that receive protrusions of a drive shaft of the fixator driver of FIG. 34A.
Figure 34G:
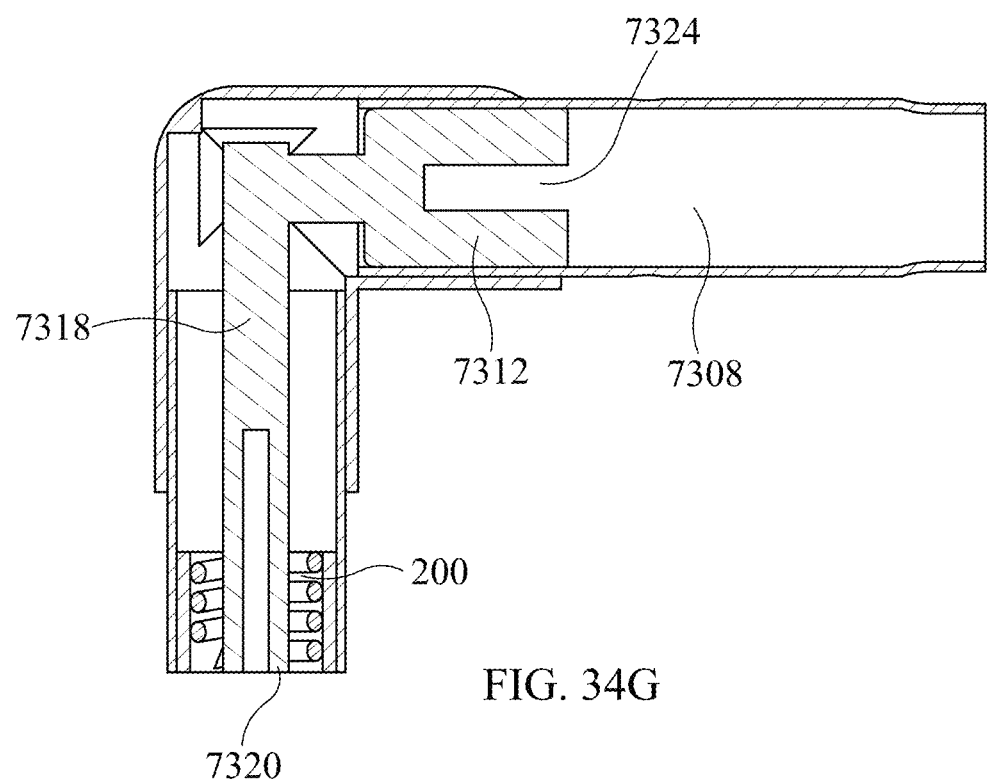
FIG. 34G illustrates a fixator loaded in a distal end portion of the cartridge, according to an embodiment of the present invention.

FIG. 34G illustrates a fixator loaded in a distal end portion of the cartridge. After installing a fixator 200, the cartridge 7310 can be reloaded with another fixator. FIG. 34 illustrates the internal components of the cartridge 7310. A flexible drive shaft or cable 7318 interconnects the receiver 7312 with a shaft 7320 on which the fixator 200 is removably mounted. FIG. 34F shows notches 7322 that receive protrusions 7324 (see FIG. 34G) of the drive shaft 7308, acting as a key feature to link the drive shaft 7308 with the receiver 7312 for rotational driving of the receiver 7312, flexible drive shaft 7318 and fixator 200. The fixator can be received in the slot of the shaft 7320 to facilitate the rotational driving in the same way as described with regard to previous driver embodiments.

Figure 35A:
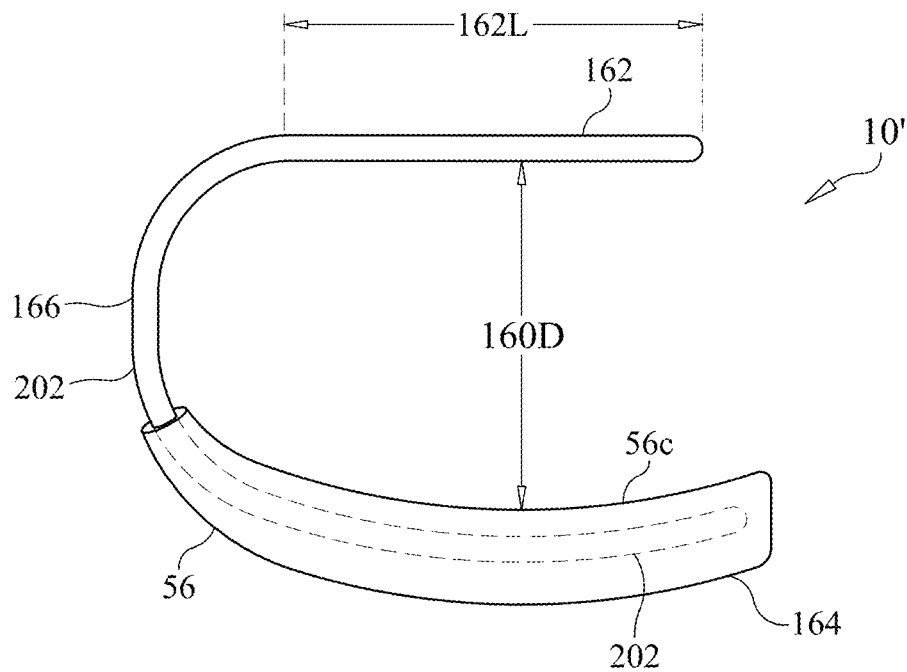
FIG. 35A is a top view of an epicardial clip according to an embodiment of the present invention.

FIG. 35A is a top view of an epicardial clip 10' according to another embodiment of the present invention. In this embodiment, device 10' may have a generally U-shape or C-shape when viewed with this orientation, like the embodiment of FIG. 1A. The device 10' may be shaped such that the distance 160D across the device 10' between the contact surface of the anterior segment 162 and the contact surface 56c of pad 56 of the posterior segment 164 defines the space between which the mitral valve and mitral valve annulus (as well as the heart walls apposite these features) will be located after implantation of the device 10' and may determine the final anterior-posterior diameter/dimension of the mitral valve annulus and/or septal-lateral diameter/dimension of the mitral valve annulus. Device 10' may be provided in a kit of devices having different distance 160D measurements that can be used to treat various mitral valves/annuli of different sizes and/or different states of degenerative progression of mitral valve regurgitation. For example a first device 10' may have a distance 160D in a range from about 25 mm to 40 mm, 28 mm to 37 mm, 30 mm to 35 mm or about 34 mm to 35 mm; another device may have a distance 160 in a range from about 30 mm to 45 mm, 33 mm to 42 mm, 35 mm to 40 mm or about 39 mm to 40 mm; another device may have a distance 160D in a range from about 35 mm to 50 mm, 38 mm to 47 mm, 40 mm to 45 mm or about 44 mm to 45 mm; another device 10' may have a distance 160D in a range from about 45 mm to 60 mm, 48 mm to 57 mm, 50 mm to 55 mm or about 49 mm to 50 mm.

The posterior segment 164 includes a pad 56 that surrounds the wire frame 202 portion included in the posterior segment. Preferably pad 56 is an over-mold of silicone or other compliant, biocompatible material. The anterior segment 162 may be substantially straight as shown, and is capable of residing in the transverse sinus of the heart. The posterior segment 164 may be arcuate, corresponding to the convex curvature of the posterior ventricular wall of the heart in a location where it is designed to be positioned for implantation. The distance 160D is measured along a line normal to the anterior segment 162 and the contact surface 56c at a location where the curvature of the pad 56 makes this the greatest normal-measured distance between anterior segment 162 and posterior segment 164.

The lateral segment 166 interconnects the anterior 162 and posterior 164 segments with a sufficient length to establish the appropriate distance 160D between the segments 162 and 164 for effectively applying force to the mitral valve annulus to cause a reduction or elimination of mitral valve regurgitation. The main body or frame 202 of device 10' is non-flexible and is rigid to an extent wherein the conformation shown is not readily deformed and is not deformed by the forces applied to it by the beating heart when it is implanted. In this embodiment, frame 202 is formed by a metal wire, preferably out of titanium or titanium alloy, but could alternatively be formed from other biocompatible metals such as stainless steel, such as 304V, 304L, and 316LV stainless steel; mild steel; nickel-titanium alloy such as linear-elastic and/or super-elastic nitinol; other nickel alloys such as nickel-chromium-molybdenum alloys, and the like. The measurements and materials described here also pertain to the devices 10 described previously.

In some variants of this and all other embodiments described herein, the device may include a drug eluting coating in addition to pad 56. The drug eluting coating may be provided in addition to a sheath or as an alternative to the sheath. The drug eluting coating may a controlled release of a therapeutic agent over a specified period of time. The therapeutic agent may be any medicinal agent which may provide a desired effect. Suitable therapeutic agents include drugs, genetic materials, and biological materials. Some suitable therapeutic agents which may be loaded in the drug eluting coating include, but are not necessarily limited to, antibiotics, antimicrobials, antioxidants, anti-arrhythmics, cell growth factors, immunosuppressants such as tacrolimus, everolimus, and rapamycin (sirolimus), therapeutic antibodies, wound healing agents, therapeutic gene transfer constructs, peptides, proteins, extracellular matrix components, steroidal and non-steroidal anti-inflammatory agents, antiproliferative agents such as steroids, vitamins and restenosis inhibiting drugs, such as TAXOL®, paclitaxel (i.e., paclitaxel, paclitaxel analogues, or paclitaxel derivatives, and mixtures thereof).

As noted above, the posterior segment 164 in this embodiment includes a pad 56 which is preferably compliant and is atraumatic when contacted to target tissue such as the heart. Pad 56 encases at least a portion of, preferably substantially all of the posterior segment portion of the frame (rod) 220. As shown in FIG. 35A, pad 56 encases all of the posterior segment 164. Pad 56 is preferably made from silicone, but could alternatively be made from other compliant, biocompatible polymers.

Figure 35B:
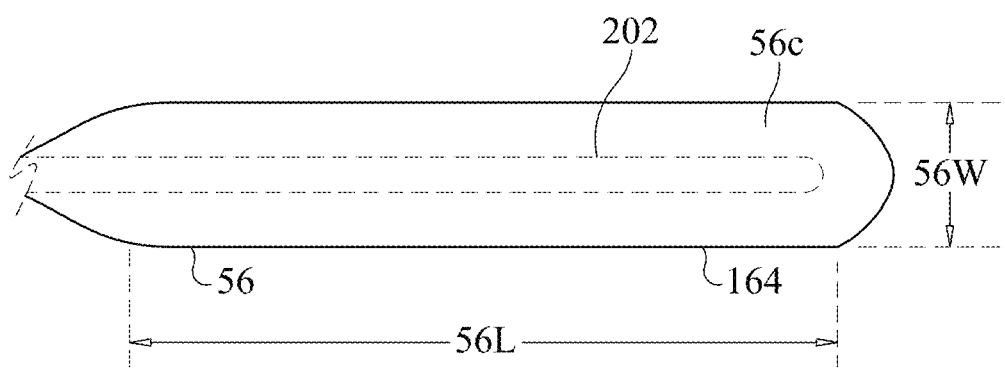
FIG. 35B is a view of the posterior segment of FIG. 35A when viewed facing the contact surface.

FIG. 35B is a view of the posterior segment 164 of FIG. 35A when viewed facing the contact surface 56c. The contact surface 56c has a width dimension 56W, a length dimension 56L and may have a shape including a tapered width at an end where the pad 56 approaches the lateral segment 166 and a rounded free end designed to be atraumatic. Length 56L may be in the range of 25 mm to 80 mm, in the range of 31 to 70 mm, in the range of 38 mm to 64 mm, or in the range of about 39 mm to about 64 mm, in some instances in the range from 30 mm to 40 mm, from 40 mm to 50 mm, from 45 mm to 55 mm, from 33 mm to 37 mm, from 43 mm to 47 mm, from 48 mm to 53 mm, in some instances 30 mm, 35 mm, 40 mm, 45 mm or 50 mm. Width 56W may be in the range of 5 mm to 30 mm, in the range of 8 mm to 25 mm, in the range of 10 mm to 20 mm, or 12 mm to 18 mm or 13 mm to 17 mm or 14.5 to 15.5 mm in some instances. The posterior segment 164 may have a radius of curvature extending along the length thereof that is variable and designed to conform to the contour of the heart wall against which it is intended to apply force. The largest radius of curvature along the length direction of the contact surface 56c may be in the range of 50 mm to 130 mm, 140 mm to 115 mm, 75 mm to 105 mm, or about 73 mm to 104 mm in some instances. It is noted that the foregoing measurements also apply to the pad 56 of device 10.

The anterior segment 162 has a length 162L designed so that the anterior segment 162 can be received in the transverse sinus, and so that with the lateral segment 166 contacting the surface of the heart, the free end of anterior segment 162 extends as far into the transverse sinus as possible without obstructing a pulmonary vein or other structure that could be extending into the transverse sinus 14. Anterior segment 162, may be a straight segment, such as illustrated in FIG. 35A and length 162L may be in the range from 40 mm to 80 mm, in the range from 45 mm to 50 mm, in the range from 50 mm to 55 mm, 55 mm to 60 mm, 60 mm to 65 mm, 65 mm to 72 mm, 72 mm to 80 mm or in the range from 40 mm to 85 mm in some instances. It is noted that the foregoing measurements also apply to the anterior segment 162 of device 10.

In one specific, non-limiting embodiment, at least two devices 10 are provided in a kit, the first device having a length 162L different from a length 162L of a second device 10 and the first and second devices have equal width measurements 160. In another non-limiting embodiment, at least two devices 10 are provided in a kit, the first device having a length 162L equal to a length 162L of a second device 10 and the first and second devices have unequal width measurements 160. In another non-limiting embodiment, at least two devices 10 are provided in a kit, the first device having a length 162L different from a length 162L of a second device 10 and the first and second devices have unequal width measurements 160. In one specific, non-limiting embodiment, at least two pairs of devices 10 are provided wherein a first pair has equal width measurements 160 and unequal length measurements, and the second pair has equal width measurements 160 to each other (but unequal to the width measurement 160 of the first pair) and unequal length measurements. 162L. In at least one embodiment, the unequal length measurements 162L are also unequal to each of the length measurements 162L of the second pair. In at least one embodiment, at least one of the unequal measurements 162L is equal to one of the unequal measurements 162L of the second pair. More than a pair of devices 10 having the same width measurement 160 may be provided, with each having a length measurement 162L different from the others. More than two different width 160 sizes of devices may also be provided, wherein multiple ones of each particular width size 160 each have a different length 162L: In one specific example, two devices 10 having a width of 35 mm were provided with a first of these devices 10 having a length 162L of 55 mm and the second having a length of 48 mm; two devices 10 having a width of 40 mm were provided with a first of these devices 10 having a length 162L of 63 mm and the second having a length of 56 mm; two devices 10 having a width of 45 mm were provided with a first of these devices 10 having a length 162L of 70 mm and the second having a length of 63 mm; and two devices 10 having a width of 50 mm were provided with a first of these devices 10 having a length 162L of 78 mm and the second having a length of 70 mm. Optionally, a third device 10 having a width of 50 mm had a length 162L of 63 mm.

Figure 36A:
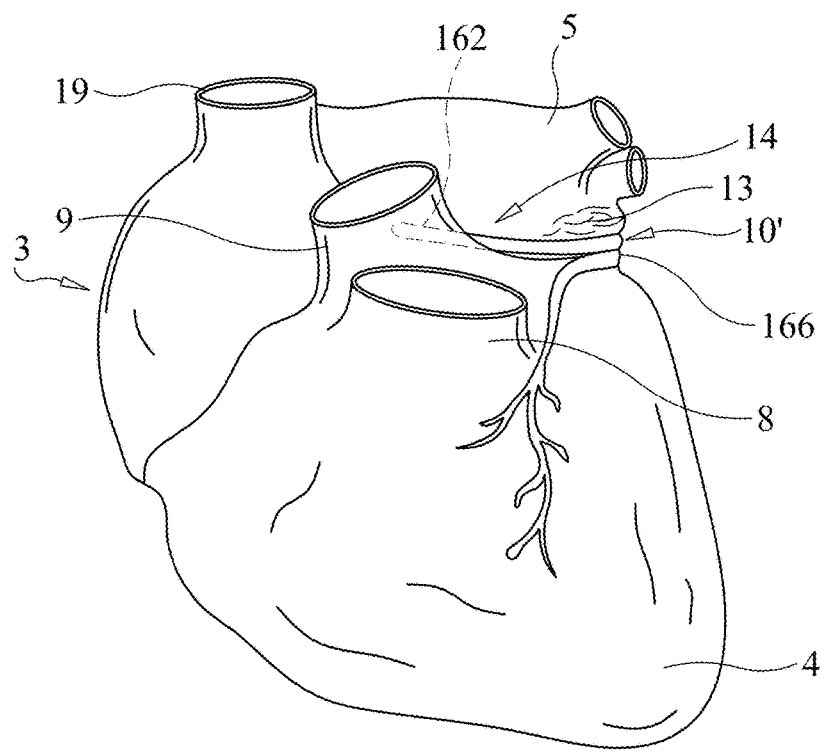
FIG. 36A is an anterior view of the heart, with the device of FIG. 35A placed on an epicardial surface thereof.

FIG. 36A is an anterior view of the heart 3, with the device 10' of FIG. 35A placed on the epicardial surface of the heart 3. As shown in FIG. 36A, the anterior segment 162 of the device 10' is positioned in the transverse sinus 14 posterior to the aorta 9 and the pulmonary trunk 8 and anterior to the left atrium 5 and the superior vena cava 19. The lateral segment 166 may extend around the left lateral side of the heart 3 at a location inferior to the left atrial appendage 13. In other embodiments, the lateral segment 166 may extend around the left lateral side of the heart 3 at a location superior to the left atrial appendage 13 or over the left atrium 5.

Figure 36B:
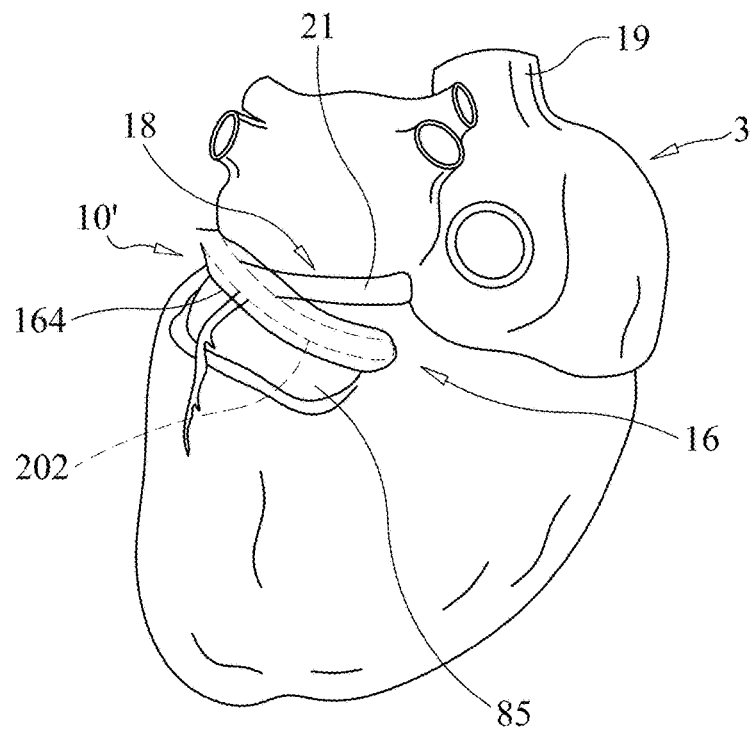
FIG. 36B is a posterior view of the heart with the device of FIG. 35A placed on an epicardial surface thereof.

FIG. 36B is a posterior view of the heart 3 with the device 10' of FIG. 35A placed on the epicardial surface of the heart 3. As shown in FIG. 36B, the posterior segment 164 of device 10 is positioned on the posterior of the heart 3 inferior of the atrioventricular groove 18. The posterior segment 164 may be positioned such that it is just below the circumflex artery 21. In other embodiments, the posterior segment 164 may be positioned such that it is just above the circumflex artery 21.

Thus, the anterior segment 162 may be located in the transverse sinus 14. The posterior segment 164 may be positioned on the posterior side of the heart 3, such as on or inferior to the atrioventricular groove 18 or in the oblique sinus 16. In some embodiments, the posterior segment 164 may be positioned inferior to the atrioventricular groove 18 on the posterior side of the heart 3. The lateral segment 166 may extend around the left lateral side of the heart 3 such that the anterior segment 162 is properly positioned in the transverse sinus 14 while the posterior segment 164 is properly positioned on the posterior side of the heart 3, such as on or inferior to the atrioventricular groove 18 or in the oblique sinus 16. In some embodiments, the lateral segment 166 may extend around the heart 3 at a location inferior to the left atrial appendage 13. However, in other embodiments the lateral segment 166 may extend around the heart 3 at a location superior to the left atrial appendage 13 or over the left atrium 5 to join the anterior segment 162 and the posterior segment 164. The anterior and posterior ends are spaced apart from one another by a predetermined distance and remain separated by a gap or opening after completion of implantation of the device 10'.

The devices 10, 10' of the present invention, when properly positioned, may reside on the epicardial surface of the heart 3, interior of the pericardium 15. Thus, positioning of the device 10, 10' may not require penetration of the heart into one or more of the chambers of the heart and/or may not require the device 10, 10' to come into contact with blood being located inside the chambers of the heart 3. By placing the device 10, 10' on the epicardial surface, exterior of the interior of the heart 3, complications associated with surgical procedures in which access is required to one or more of the chambers of the heart 3 are avoided. Furthermore, the time required to complete the surgical procedure may be greatly reduced from the time required for an open heart surgery or a surgical procedure requiring accessing the heart 3 through the vasculature.

When the device 10, 10' is properly positioned with the anterior segment 162 located in the transverse sinus 14 and the posterior segment 164 located on or inferior to the atrioventricular groove or in the oblique sinus 16, as described above, the device 10, 10' may apply an inward pressure/force on the walls of the heart 3. The inward pressure/force exerted by the device 10, 10' may alter the geometry of the annulus of the mitral valve located between the left atrium 5 and the left ventricle 4, thus reducing the anterior-posterior distance across the mitral valve and/or the septal-lateral distance across the mitral valve. The amount of force applied by the device 10, 10' to the heart to optimize the functionality of the mitral valve to reduce or eliminate mitral valve regurgitation is a function of the amount of deformation of the heart 3 walls that results by application of such force. The distance 160D needed for spacing between the contact surfaces of the anterior 162 and posterior 164 segments can be measured, for example with echocardiographic images, so that an appropriately sized device 10, 10' can be selected for implantation to optimize the functionality of the mitral valve.

Figure 37A:
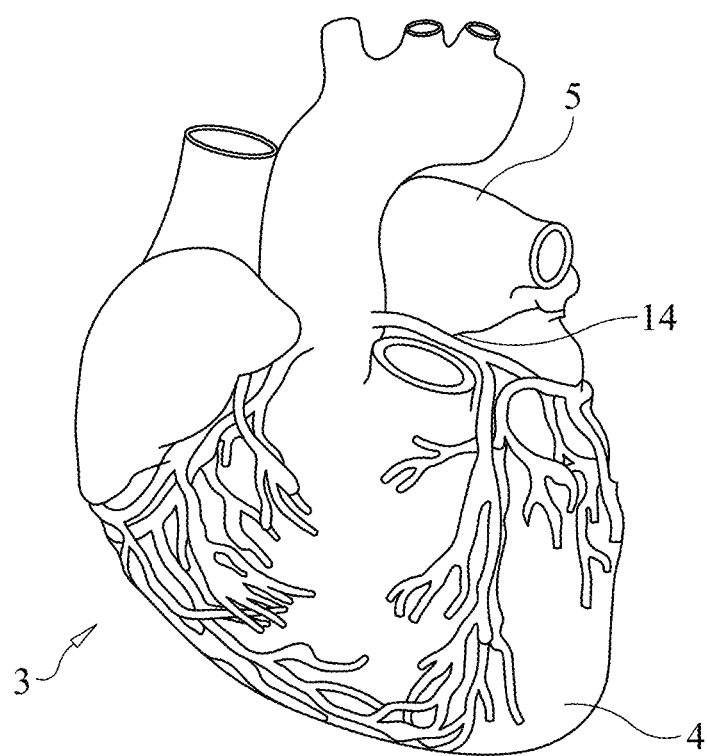
FIG. 37A illustrates an anterior view of a heart.

The device/clip 10, 10' of the present invention may be positioned on the epicardial surface of the heart 3 during a medical procedure. For example, in some embodiments the device/clip 10, 10' may be installed on the heart 3 during a beating heart surgery, without the need of a heart/lung bypass machine. For instance, the device/clip 10, 10' may be implanted on the heart 3 through an open chest procedure (sternotomy) or a lateral thoracotomy. In some embodiments, the device/clip 10, 10' may be positioned on the heart 3 through a less-invasive endoscopic approach. An exemplary, non-limiting embodiment of a procedure for installing the device/clip 10' of FIG. 35A is now described. In this embodiment, the heart 3 is exposed by way of an open chest procedure, via a sternotomy, according to known techniques. Upon opening the chest, an anterior view of the heart is directly visible to the surgeon. FIG. 37A illustrates an anterior view of the heart 3, with the left ventricle 4, left atrium and transverse sinus 14 labeled. The posterior surface of the heart 3, posterior surface of the ventricle 4, atrioventricular groove 18 and the oblique sinus 16 therefore cannot be seen by the eyes of the surgeon.

Figure 38A:
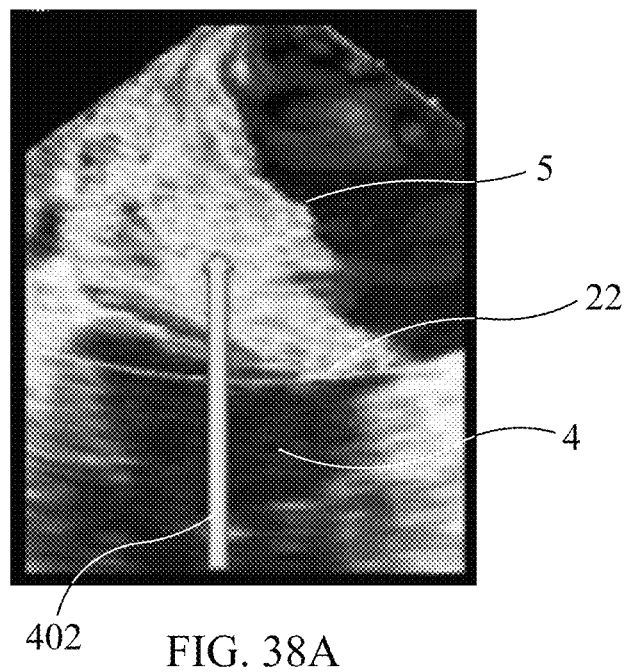
FIG. 38A shows an echocardiogram illustrating an occurrence of severe mitral valve regurgitation.
Figure 38B:
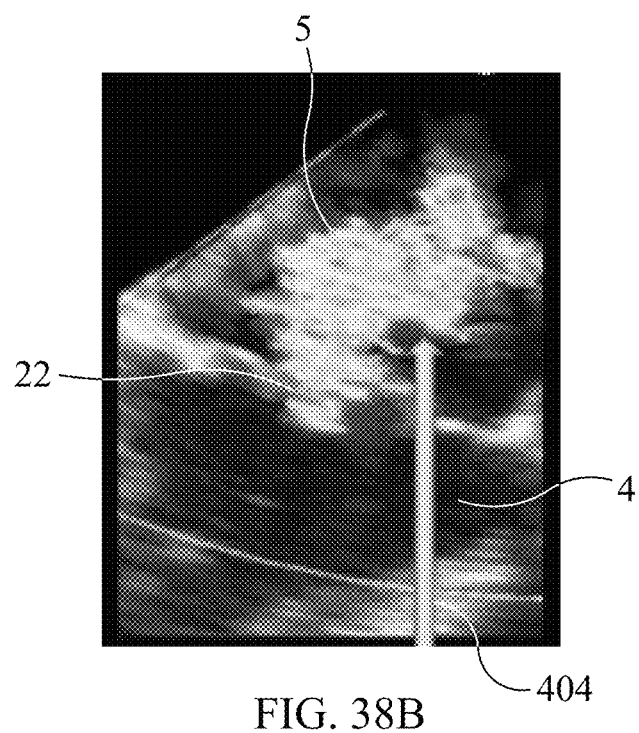
FIG. 38B shows an echocardiogram illustrating an occurrence of moderate mitral valve regurgitation.
Figure 38C:
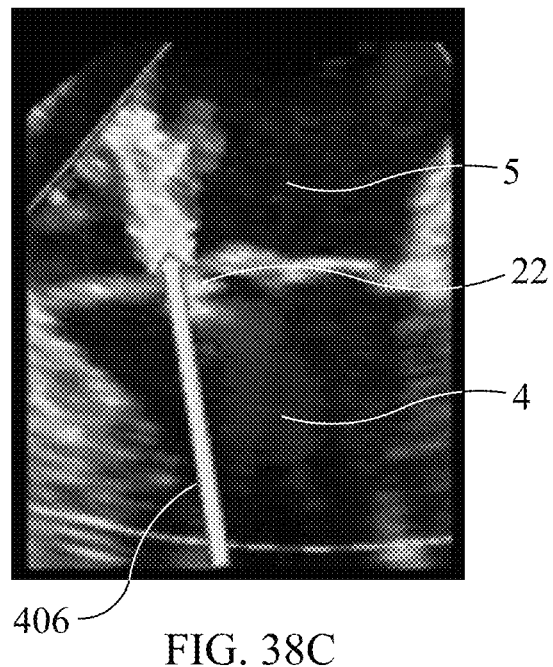
FIG. 38C shows an echocardiogram illustrating an occurrence of mild mitral valve regurgitation.
Figure 38D:
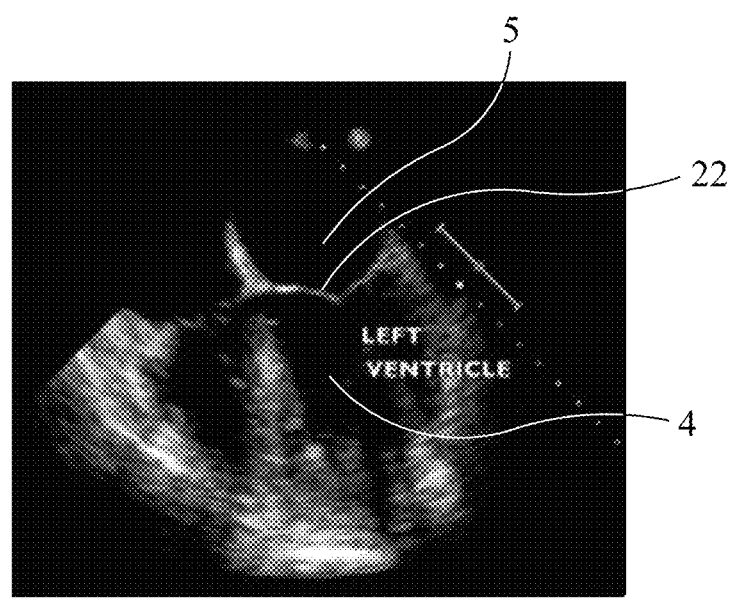
FIG. 38D shows an echocardiogram illustrating no occurrence of mitral valve regurgitation.

Visualization of the blood flow through the mitral valve 22 can be provided by echocardiography, for example to identify mitral valve regurgitation that may be occurring. The echocardiography provides images that show blood flowing from the left atrium 5 through the mitral valve 22 and into the left ventricle 4 (atrial systole) and also provides images that can identify when blood flows retrograde from the ventricle 4 through the mitral valve 22 and into the left atrium 5, a malady that typically occurs during ventricle systole. Ultrasound energy is applied to the heart 3 in the area of the left ventricle 4, mitral valve 22 and left atrium 5 to provide images that are transverse to the plane of the mitral valve annulus, which may or may not be normal to the plane, but are typically near to normal. However, other angles of visualization may also be used. FIG. 38A shows an echocardiogram illustrating occurrence of severe mitral valve regurgitation, where a large, brightly colored plume 402 indicates the retrograde blood flow through the mitral valve, thus indicating the large volume of regurgitation of blood from the ventricle. FIG. 38B shows an echocardiogram illustrating occurrence of moderate mitral valve regurgitation where plume 404 is somewhat smaller than plume 402 and less brightly colored overall, indicating that the amount of retrograde blood flow through the mitral valve 22 during ventricle systole is less than that shown in FIG. 38A. FIG. 38C shows an echocardiogram illustrating occurrence of mild mitral valve regurgitation 402, wherein plume 406 is clearly much smaller than 402 and much smaller than 404. FIG. 38D shows an echocardiogram where no mitral valve regurgitation occurs during ventricular systole, as it can be seen that the left atrium is dark in this echocardiogram. By providing real time cardiography as described, the surgeon/surgical team can visually ascertain the amount of mitral valve regurgitation as the heart 3 is manipulated in an effort to find a condition where optimal minimization or elimination of mitral valve regurgitation can be achieved.

Figure 37B:
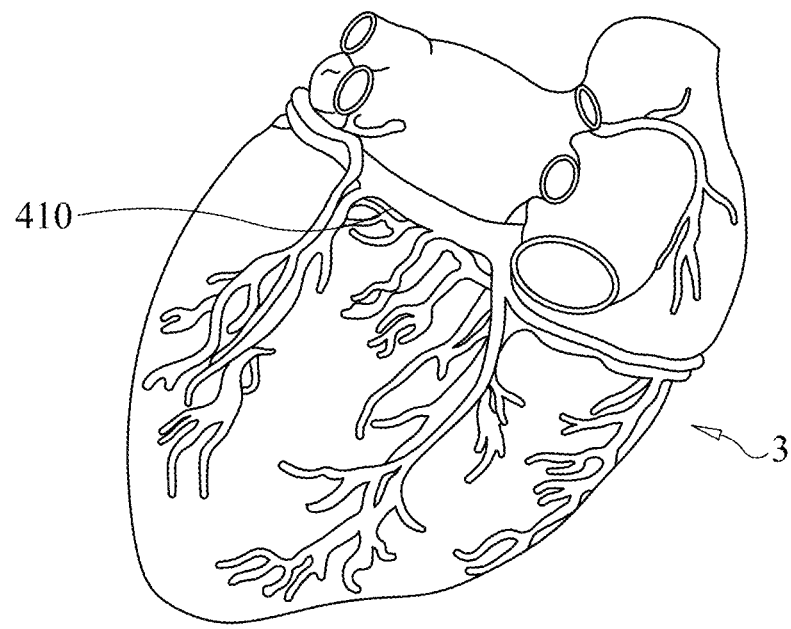
FIG. 37B illustrates a posterior view of the heart of FIG. 37A.

To perform such manipulation, force is applied posteriorly to the heart 3 on or inferior to the atrioventricular groove 18 or in the oblique sinus 16, in a location where the posterior segment 164 is intended to contact the heart 3 upon implantation of the device/clip 10. FIG. 37B indicates the general location where the force is applied. Note that because FIG. 37B is a posterior view of the heart 3, the surgeon cannot see where the force is being applied, but it needs to be applied through feel to locate the appropriate location to apply the force. The amount of force and/or location of application of force applied may be varied while viewing the echocardiographs provided in real time on a monitor until a location and amount of force are applied that achieve a result of optimal minimization or elimination of mitral valve regurgitation.

Figure 39:
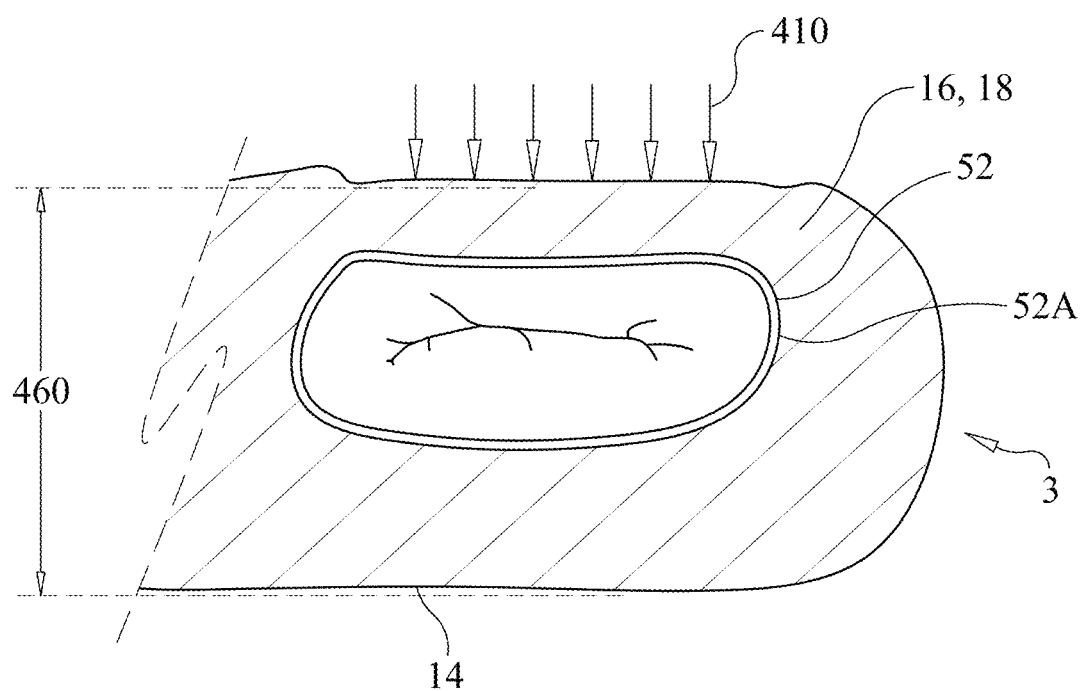
FIG. 39 is a schematic representation of an electrocardiogram used for taking a measurement for sizing a width of an epicardial clip to be used, according to an embodiment of the present invention.

When the location and amount of force applied for achieving a result of optimal minimization or elimination of mitral valve regurgitation are established, an echocardiogram taken in a plane (or approximating a plane) of the mitral valve annulus is provided, a schematic illustration of which is shown in FIG. 39. A measurement of distance 460 between the epicardial surface of the posterior heart 3 wall and the epicardial surface of the anterior heart wall in the transverse sinus 14, at locations corresponding to locations of distance 160D measured in FIG. 35A, on the heart 3 where those locations of the device/clip 10 are intended to be located, provides a measurement 460 that can be used to select a device/clip, wherein measurement 160D of device/clip 10 is equal to measurement 460 (or nearest to measurement 460, as selected from a kit of devices/clips having different measurement distances 160D.

Figure 40A:
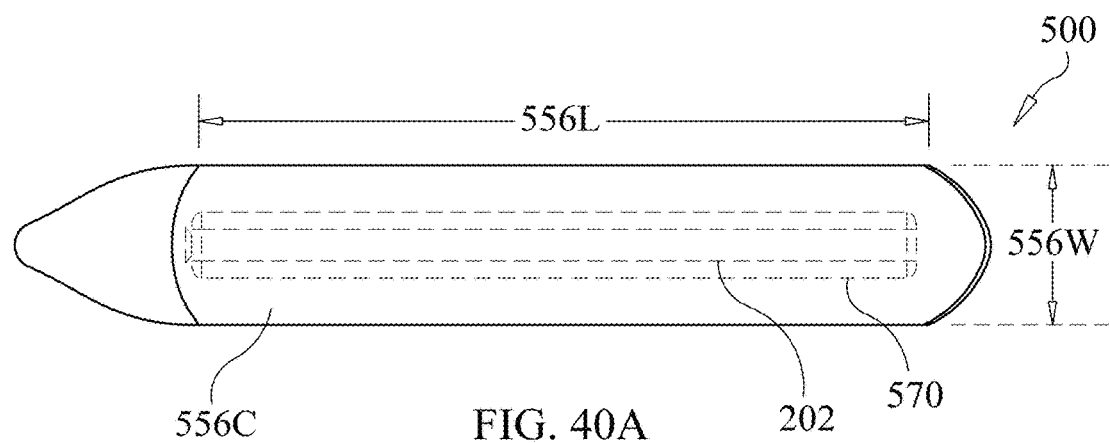
FIG. 40A is a top view of a width sizing instrument, according to an embodiment of the present invention.

FIG. 40A is a view of a width sizing instrument 500 with a view of the contact surface 556c according to an embodiment of the present invention. The width 556W and length 556L are preferably the same as the width 56W and length 56L of the contact surface 56 of device/clip 10 that is intended to be implanted, in order to provide a close simulation of the manner in which force will be applied through the contact surface 56 to the heart 3. Likewise, it is preferred that the curvature and conformation of the contact surface 556c be the same, or closely matching that of the curvature of contact surface 56c. At least the contact component 556 may be made from the same material as the pad 56. However, because silicone is not highly visible under echocardiography, it may be preferable to include one or more contrast agents such as air bubbles encapsulated in the contact component material, low solubility fluorocarbon gas, polymer shell and low solubility gas, or other contrast materials known in the art. Further optionally, a rod/rib 202 having the same characteristics (makeup, dimension, shape, etc.) of rod/rib 202 of the device 10 may be included as shown. Length 556L may be in a range from 25 mm to 70 mm, 30 mm to 60 mm, 40 mm to 50 mm, or 42 mm to 48 mm, for example. In one particular embodiment, length 556L was 45 mm. Width 556W may be in a range from 5 mm to 30 mm, 10 mm to 25 mm, 12 mm to 20 mm, or 13 mm to 17 mm, for example. In one particular embodiment, width 556W was 15 mm.

Figure 40B:
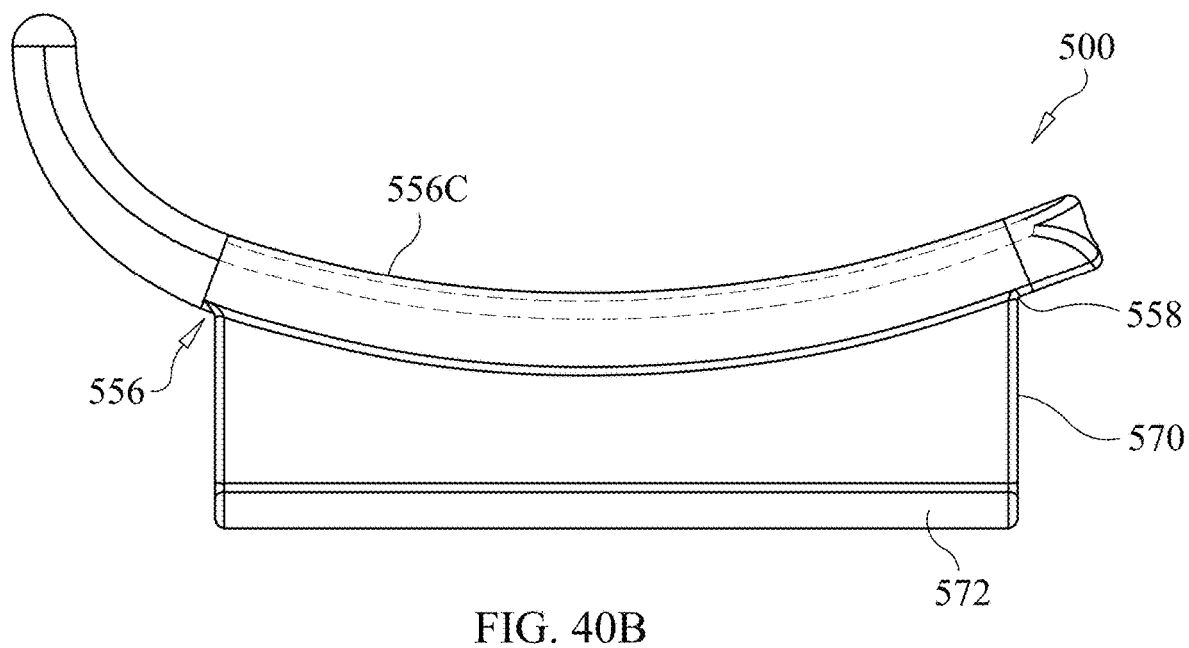
FIG. 40B is a side view of the instrument of FIG. 40A.
Figure 40C:
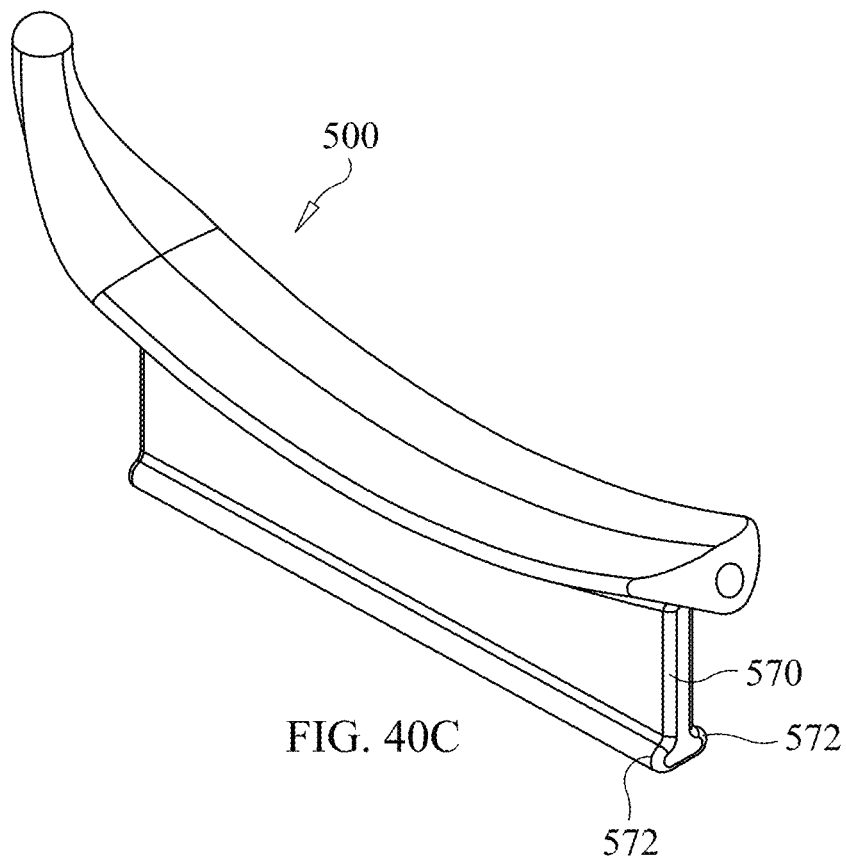
FIG. 40C is a perspective view of the instrument of FIG. 40A.
Figure 40D:
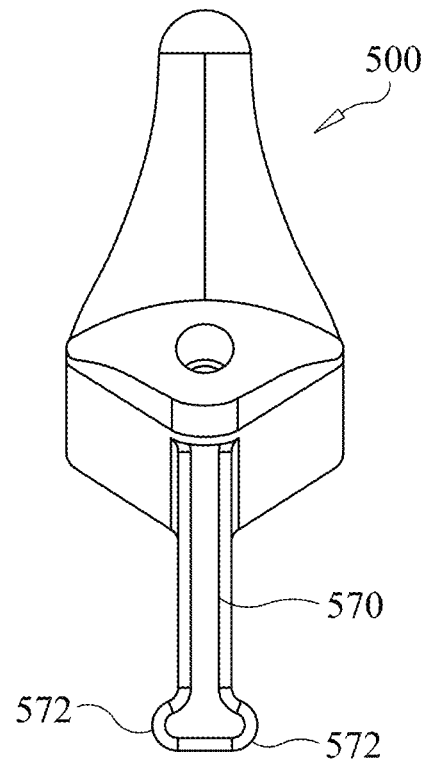
FIG. 40D is an end view of the instrument of FIG. 40A.
Figure 40E:
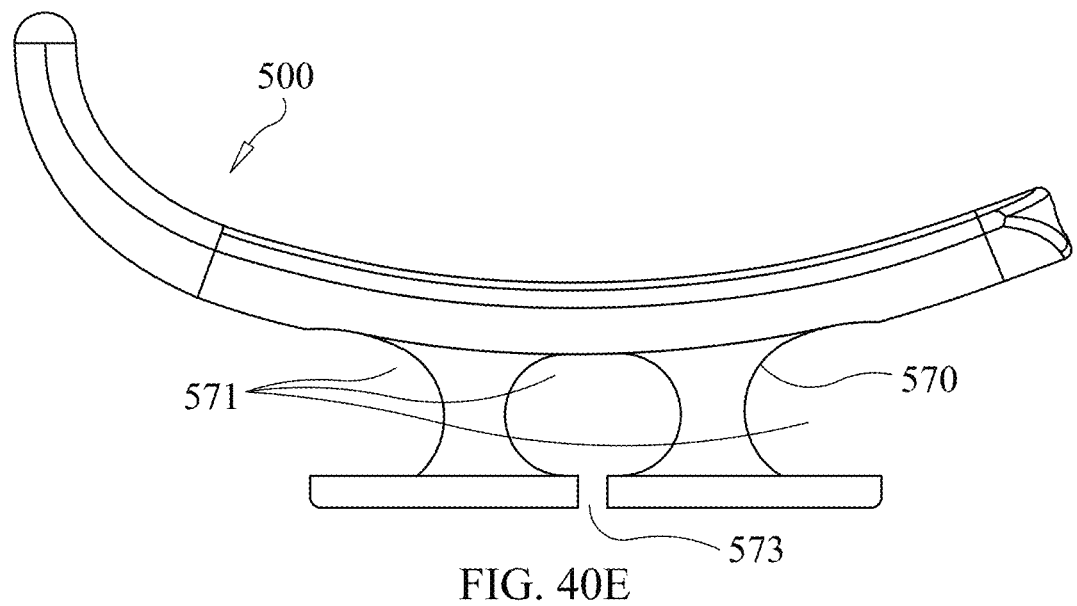
FIG. 40E is a side view of a variant of the instrument of FIG. 40A.

FIG. 40B is a side view of the width sizing instrument 500 of FIG. 40A after rotation about its longitudinal axis by ninety degrees. A fin 570 may be either attached to or integral with the back surface 558 of the contact component 556 and is configured to facilitate handling of the width sizing instrument 500 by the user. To use the width sizing instrument 500, the user cradles the back surface in the user's hand, with the fin 570 being inserted between two adjacent fingers. Thus fin 570 facilitates more positive grip and control over the operation of the sizer 500 relative to a sizer 500 having no such fin. To still further secure the control of the sizing instrument 500, the fin 570 may include flanges 572 or other enlargements at the free end thereof which serve as a further restriction or backstop against the user's fingers to prevent them from slipping away from the contact component 556. In the embodiment of FIGS. 40A-40D, the flanges 572 extend continuously along the full length and on both sides of the free end of the fin 570 as shown the perspective view of FIG. 40C and the end view (looking at the right end of FIGS. 40A-40B) of FIG. 40D. FIG. 40E shows a variant of the width sizing instrument of FIGS. 40A-40D, in which finger holes 571 have been cut into the fin 570 which allow the user's fingers to be inserted therethrough. The finger holes 571 facilitate handling of the instrument 500 are particularly useful in allowing the user to manipulate the instrument 500 from the apex of the heart. A cut 573 may optionally be provided with regard to any fully encompassing finger hole 571 to allow it to be manufactured slightly undersized, so that the cut 573 allows the hole 571 to expand slightly as a finger is inserted to it, thus providing a snug fit around the finger and maximizing the ability to control movements using the inserted finger.

By applying the contact surface 556c to the region 410 a relatively accurate simulation of the force that will be applied by contact surface 56c of device/clip 10 can be made. As noted however, this application of force is applied blindly, by feel by the surgeon as the surgeon cannot see the posterior surface of the heart at this stage of the procedure. Accordingly, once the sizer 500 has been located in a position on the heart with an amount of force applied by the user through the surface 556c against the heart to achieve a result of optimal minimization or elimination of mitral valve regurgitation, a surgical marker can be used to mark the surface of the heart by drawing around all or a portion of the perimeter of the contact surface 556c. Because this process of marking is cumbersome and may provide difficulty in accurately outlining all or a portion of the contact surface 556c where it is optimally located on the heart, the width sizing device 500 may be configured to directly mark the heart surface when desired, to accurately show all or a portion of the outline of the perimeter of the contact surface 556c, and/or another reference marking which can be used for alignment of the contact surface, such as a line along the central axis of the contact surface 556c or other reference mark.

Figure 40F:
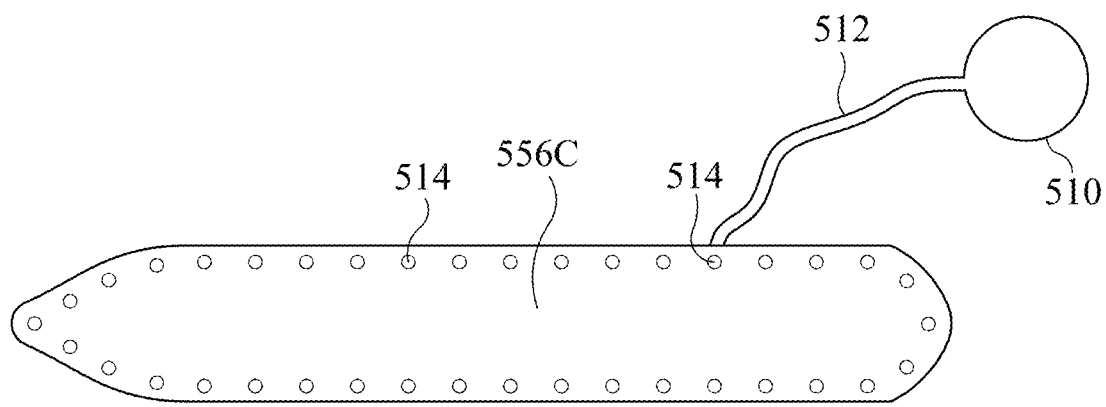
FIG. 40F schematically illustrates a width sizing instrument configured to mark a surface of the heart, according to an embodiment of the present invention.

FIG. 40F schematically illustrates a width sizing instrument 500A configured to mark the surface of the heart, according to an embodiment of the present invention. In this embodiment, a source of marking fluid, which may be any of liquid surgical marking fluids currently known and used, is contained within a squeezable reservoir 510. The reservoir is in fluid communication with pores, nozzles, openings or slots 514 (hereinafter referred to generally as "openings") formed around all or a portion of the perimeter of the contact surface 556c (or any other specified reference location or pattern) via one or more conduits 512. The one or more conduits 512 connect to the openings 514 from the back surface 558 of the device 500a and may include a manifold for distribution individually or in groups of openings 514 each being a subset of the total number of openings, or may connect to 558 at a single location for delivery of the marking fluid though channels interconnecting the openings 514. Conduit 512 extends over a sufficient length for the reservoir 510 to be located outside of the patient while the contact surface 556c is forcibly contacted to the posterior surface of the heart 3 in a manner as described above. When it is determined that the contact surface 556c has been optimally located on the heart 3, the surgeon, or an assistant, squeezes the reservoir 510 to deliver marking agent through openings 514, thereby forming a marking on the heart that traces the perimeter of the contact surface 556c. Alternatively, the squeezable reservoir may be replaced by a syringe, motorized pump and reservoir, or other reservoir and driver configured to drive the surgical marking agent out of the openings 514.

Figure 40G:
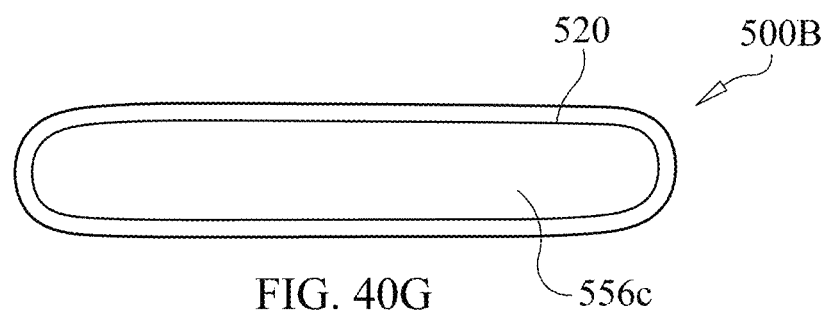
FIGS. 40G-40H schematically illustrate top and side views of a width sizing instrument configured to mark a surface of the heart, according to another embodiment of the present invention.
Figure 40H:
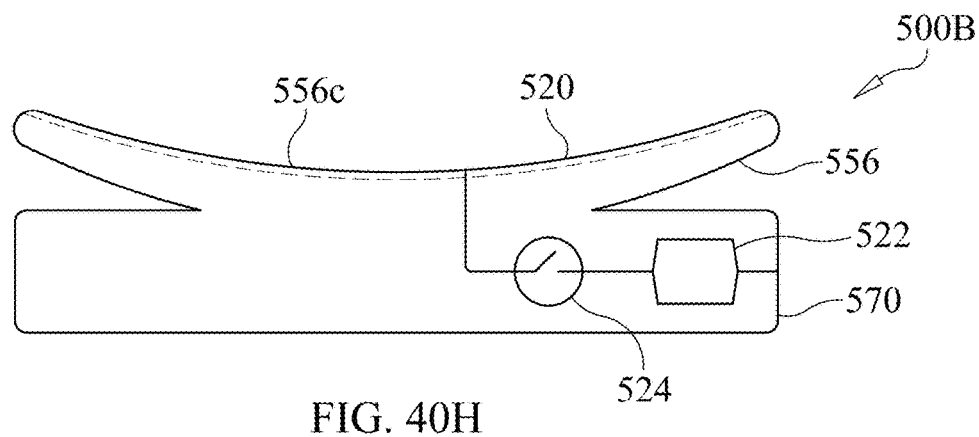

FIGS. 40G-40H schematically illustrate top and side views of a width sizing instrument 500B configured to mark the surface of the heart 3, according to an embodiment of the present invention. In this embodiment, a resistive wire, coil or other resistive element configured to heat up, when current is supplied thereto, by an amount sufficient to singe the heart 3 tissue (hereinafter referred to generally as resistive wire 520) is located on the contact surface 556c (or flush therewith) around all or a portion of the perimeter of the contact surface 556c (or any other specified reference location or pattern on or flush with the contact surface 556c) and is in electrical communication with a switched source of electrical power. For example, fin 570 may have a battery 522 located therein or thereon as the source of electrical power, with a switch 524 electrically connecting the power source 522 with the resistive wire when switch 524 is closed. In one embodiment, switch 524 can be a push button actuatable by the user by squeezing together the fingers holding the fin 570 so as to depress the push button to the closed (on) position. In this embodiment, the push button 524 can be biased outwardly to the open (off) position, so that if the user is not squeezing her/his fingers together, the switch is off. Alternative types of switches could be substituted as would be apparent to those of ordinary skill in the art. Further alternatively, the power source 522 and/or switch 524 may be located externally of the patient while the contact surface 556c is in contact with the posterior surface of the heart 3. Further alternatively, an external power source may be an AC or DC source supplied by a wall socket, generator, or the like. When it is determined that the contact surface 556c has been optimally located on the heart 3, the surgeon, or an assistant (which may depend upon the embodiment used), closes the switch 524 to apply electrical power to the resistive wire, in an amount and over a time sufficient to singe the tissue to form a reference mark, while ensuring that the amount and/or time is not so great as to result in unnecessary amounts of burning or damage to the tissue. For example, a circuit may be provided that limits the time and power of the application of electricity to the resistive wire 520, by predetermined amounts that are sufficient to establish the reference mark and are minimized to prevent unnecessary damage to the tissue.

Figure 40I:
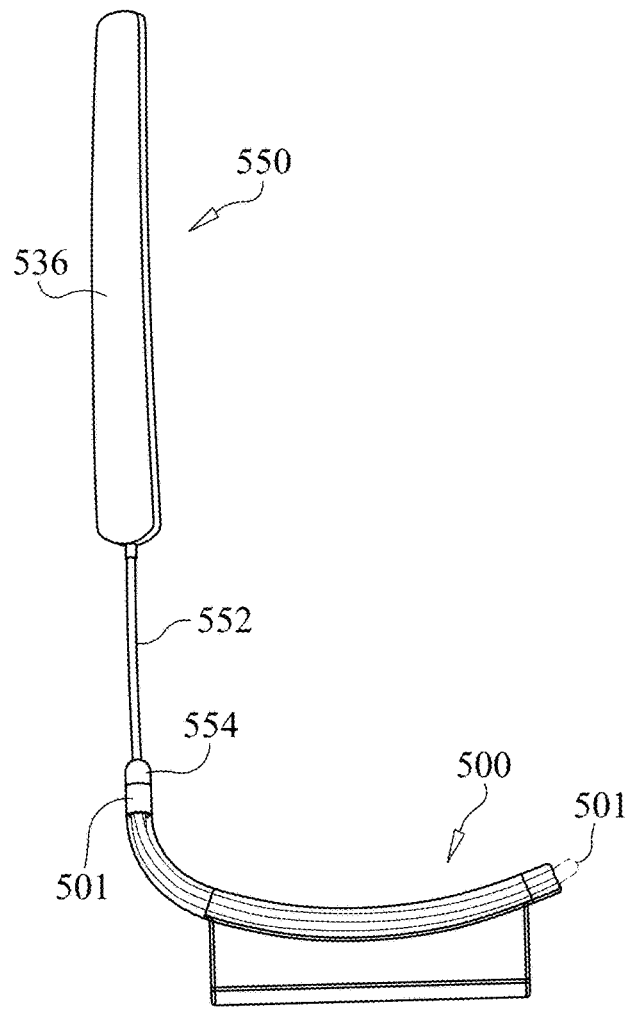
FIG. 40I illustrates a width sizing instrument provided with an extension handle according to an embodiment of the present invention.

FIG. 40I illustrates width sizing instrument 500 provided with an extension handle 550 according to an embodiment of the present invention. Handle 550 is rigid and may have a metal shaft 552 made of titanium or steel or any of the other metals and metal alloys described herein for use in making the clip. The distal end of the shaft 552 includes a connector 554 that mates with a connector 501 provided on the width sizing instrument 500. In at least one embodiment, the connectors 554, 501 are mating threads and in at least one embodiment the threads and threaded tips making up the connectors 554, 501 are made of titanium. Alternate types of connectors may be substituted, including, but not limited to, bayonet fittings, ball and detent connectors, etc. Further alternatively, although not preferred, the extension handle 550 could be permanently fixed to the sizing instrument 500 such as by adhesive, welding, etc., or could be integral with the sizing instrument. The handle portion 556 of the extension handle 550 can be straight or curved and made of polymer or metal, but typically has a greater cross-sectional area than that of the shaft 552 to make it easier to grasp by the hand of the user. The extension handle 550 has a length sufficient to allow the user to manipulate the sizing instrument from a location anterior to the posterior wall of the heart 3. The extension handle 550 extends at least to the level of the anterior wall of the left ventricle 4 when the sizing instrument is contacting the posterior wall of the left ventricle to perform a size measurement. In open chest procedures, the length of the extension handle 550 may be sufficient to extend the proximal end of the handle portion 556 out of the chest of the patient. For example, the length of shaft 552 may be in the range from about 5 cm to 15 cm, or from 7.5 cm to 13 cm, and in at least one embodiment was about 10 cm. The length of the handle 550 may be in a range from 7.5 cm to 26 cm, typically from 10 cm to 20 cm, and in at least one embodiment was about 15 cm. Optionally a second connector 501 may be provided at the opposite end of the sizing instrument, as shown in phantom lines in FIG. 40I, to permit extension handle 550 to be attached at the opposite end portion of the device 500.

Figure 40J:
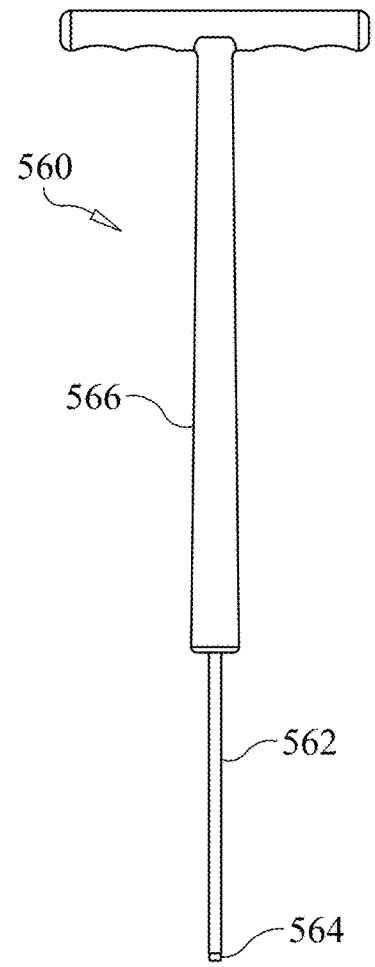
FIG. 40J illustrates an extension handle for use with a width sizing instrument, according to another embodiment of the present invention.
Figure 40K:
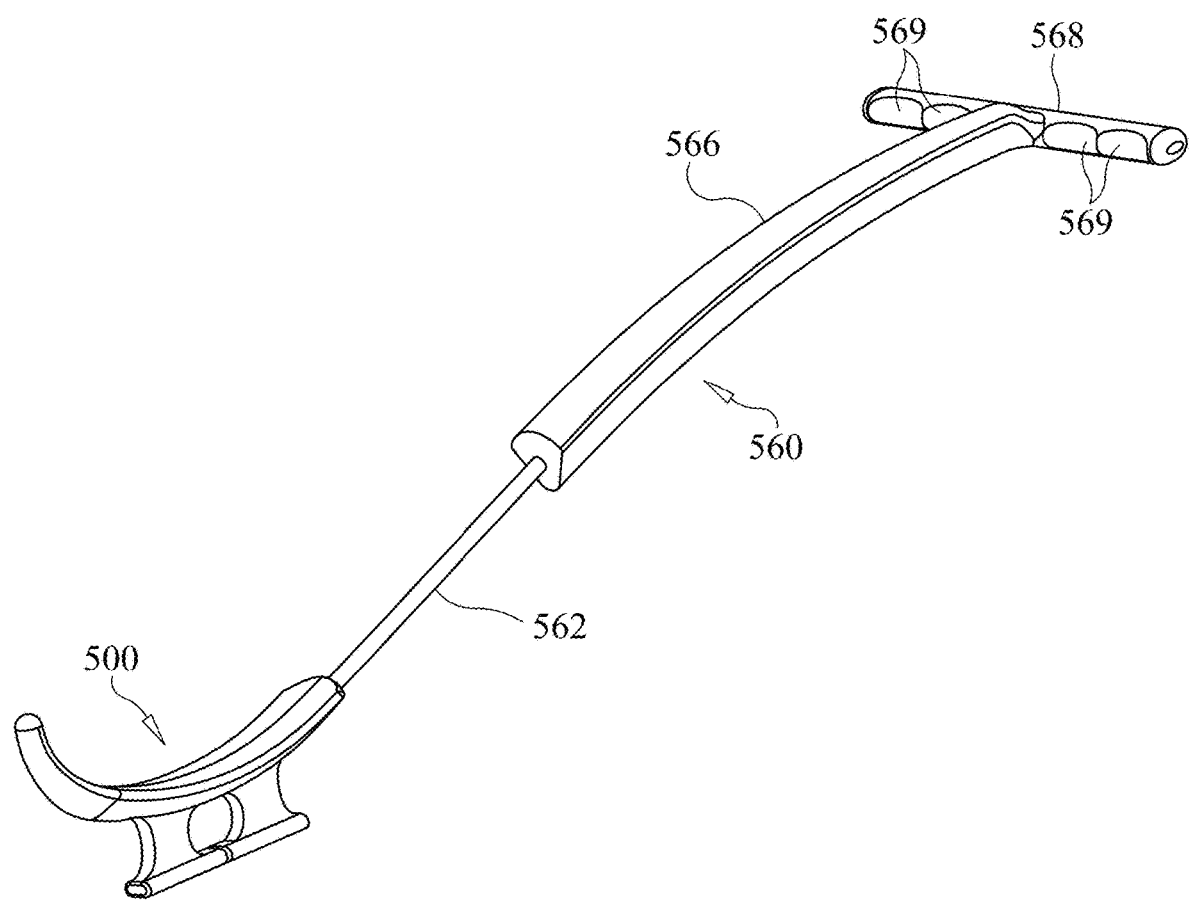
FIG. 40K illustrates a width sizing instrument provided with the extension handle of FIG. 40J.

FIG. 40J illustrates an extension handle 560 according to another embodiment of the present invention, and FIG. 40K illustrates width sizing instrument 500 provided with extension handle 560 attached thereto. Handle 560 is rigid and may have a metal shaft 562 having any or all of the same characteristics of shaft 552 described above. The distal end of the shaft 562 includes a connector 564 that mates with a connector 501 provided on the width sizing instrument 500, and which may have any or all of the same characteristics of connector 554 described above. Further alternatively, although not preferred, the extension handle 560 could be permanently fixed to the sizing instrument 500 such as by adhesive, welding, etc., or could be integral with the sizing instrument. The handle portion 566 of the extension handle 560 is curved as shown in FIG. 40K, but could alternatively be straight, and can have any or all of the same characteristics of the handle 556 described above. Additionally, handle 566 is provided with a T-bar 568 that extends transverse to main body 566 and longitudinal axis of the handle. Preferably, although not necessarily, the T-bar 568 is oriented normal to the longitudinal axis of handle 566 and preferably, although not necessarily, the T-bar 568 is fixed or mounted across the proximal end of the main body 566 as shown in FIG. 40K. Optionally, finger indents 569 can be formed in the T-bar to facilitate grasping thereof by the hand of a user. Grasping of the T-bar facilitates the user's ability to torque the handle 566 about its longitudinal axis, as well as rock, angulate, or other maneuvers of the handle to effect movements and positioning of the width sizing instrument 500. The T-bar may have a length in a range from 3.5 cm to 12.5 cm, typically from five cm to ten cm, and in at least one embodiment was 7.5 cm.

After measuring the width 460 as described above and establishing a reference mark on the posterior surface of the heart 3 manually, or using any of the features for marking with the width sizing device 500, 500A, 500B as described above, the heart 3 can be lifted so that at least a portion of the posterior surface of the heart 3 can be seen by the surgeon, including at least the reference mark. However, prior to this it may be desirable to perform a length measuring procedure to establish an optimum length or length range for the length 162L of the anterior segment 162 of the device/clip 10 that is to be used for the procedure. An optimal length 162L of the anterior segment 162 is one which extends as far as possible into the transverse sinus 14 as possible, without obstructing or potentially causing any damage to any structures that may lie in the path of the transverse sinus 14 and which does not extend as far as to intersect with or obstruct the right atrium or tricuspid valve. This provides the greatest amount of securement of the clip/device 10 by the anterior segment portion 162 without unduly risking damage or trauma to the surrounding tissues. Because the occurrence or existence of one or more structures (such as a pulmonary vein or other vessel or structure) lying in the path of the transverse sinus can vary from patient to patient, because the length of the transvers sinus from the left atrial appendage to the end of the left atrium between the aorta and the mitral valve, where the left atrium ends and transitions to the right side of the heart can vary from patient to patient, and because it is not possible to directly view such occurrences, it may be advantageous to perform a length measurement of the transverse sinus 14, to the extent that it is unobstructed, to determine the maximum length of anterior segment 162 of a clip/device 10 that can be safely used on a particular patient.

Figure 41A:
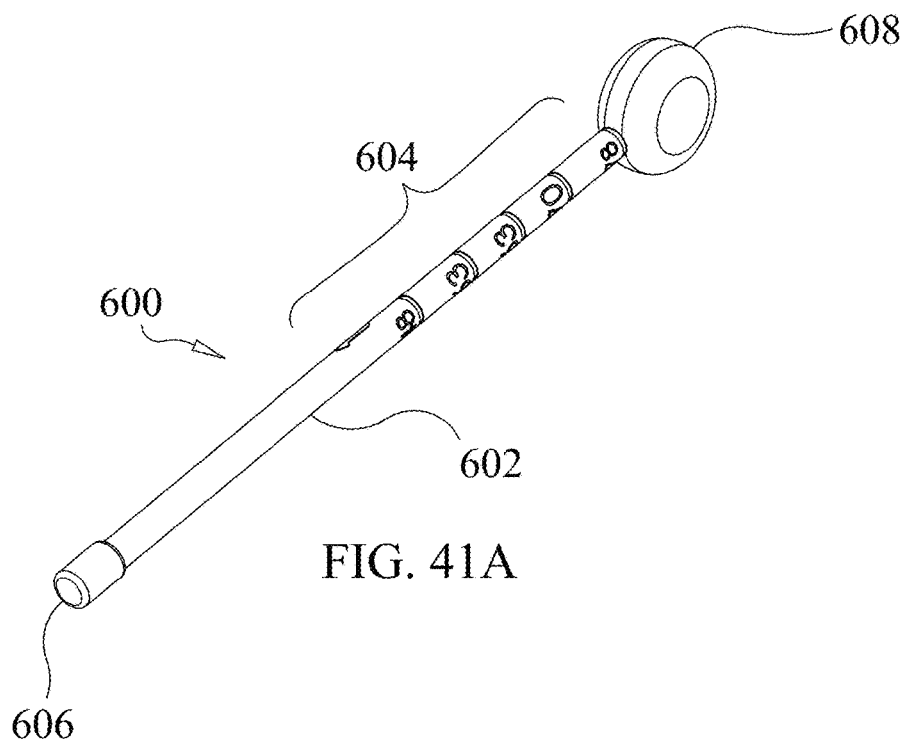
FIG. 41A is a perspective view of a length sizing instrument, according to an embodiment of the present invention.
Figure 41B:
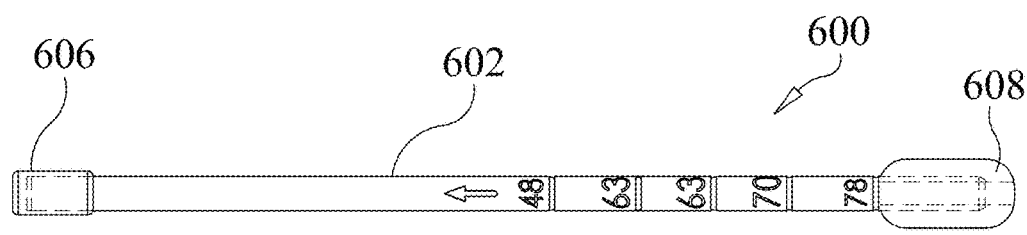
FIG. 41B is a plan view of the instrument of FIG. 41A.
Figure 41C:
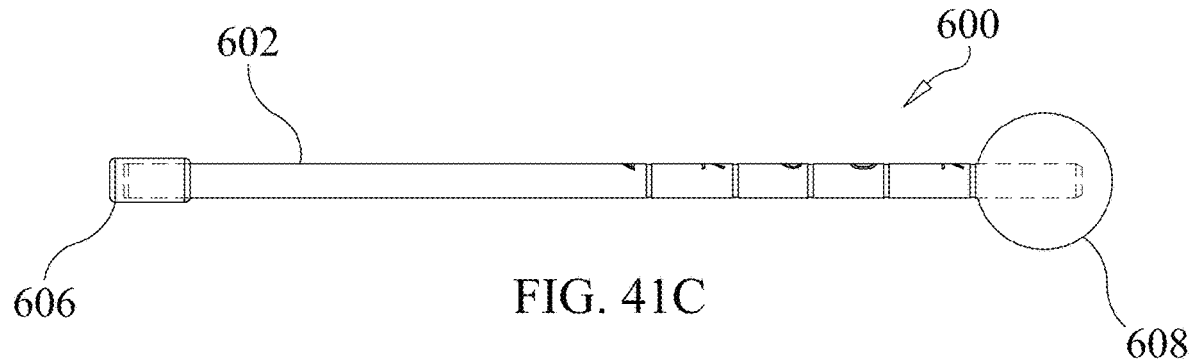
FIG. 41C is another plan view (rotated ninety degrees about the longitudinal axis of the view of FIG. 41B) of the instrument of FIG. 41A.

FIG. 41A is a perspective view, FIG. 41B is a plan view, and FIG. 41C is another plan view (rotated ninety degrees about the longitudinal axis of the view of FIG. 41B) of a length sizing instrument 600 according to an embodiment of the present invention. Instrument 600 includes a shaft 602 as the main body of the instrument. Shaft 602 is preferably a straight shaft and preferably has the same diameter as the diameter of the rod 202 used in making the device/clip 10. However, the diameter of 602 may be smaller, or even slightly larger than the rod 202 and still function. Graduated markings 604 are provided along the shaft 602 to be referenced for making measurements of the unobstructed transverse sinus 14. An atraumatic tip 606 may be formed at a distal end of the shaft 602 to prevent damage to tissues within the transverse sinus 14 (such as obstructions, or the walls of the tissue forming the transverse sinus) as the instrument 600 is being inserted into and advanced along the transverse sinus 14. Atraumatic tip 606 extends distally past the distal tip of the rigid shaft 602 and surrounds it to protect tissues from damage thereby. For example, the atraumatic tip may comprise silicone or other soft biocompatible material that is readily deformable so as not to cause trauma to tissues that it comes into contact with. Alternatively, atraumatic tip 606' may comprise a flexible coil 606 such as coil spring that may be made of metal or polymer and which readily deflects when it abuts tissue, so as to not cause trauma to the tissue contacted, see FIG. 41F. The coil 607 may be encapsulated with a polymer such as silicone or may be covered or enveloped in a sheath that could be made of any of the materials described above for making sheaths. A measuring guide 610 can be provided that can be slid along the shaft to facilitate reading a length measurement, as described in more detail below with regard to FIG. 41D. An enlargement 608 may be formed at the proximal end of the shaft 602 to function as a handle, facilitating the operation and manipulation of the instrument 600 by a user. In a preferred embodiment the instrument 600 is formed of the same materials used to make a device/clip 10, 10' of the present invention. For example, shaft 602 in one specific embodiment has a titanium shaft, and the atraumatic tip 606 and handle 608 are over-molds of silicone on the shaft 602. In another embodiment, atraumatic tip 606 and handle 608 are configured to form a friction fit with the shaft 602, such as by making the openings of the handle 608 and tip 608 of a smaller inside diameter than is the outside diameter of the shaft 602. In one particular non-limiting embodiment, these inside diameters were 0.381 mm less than the 3.175 mm outside diameter of shaft 602.

Figure 41D:
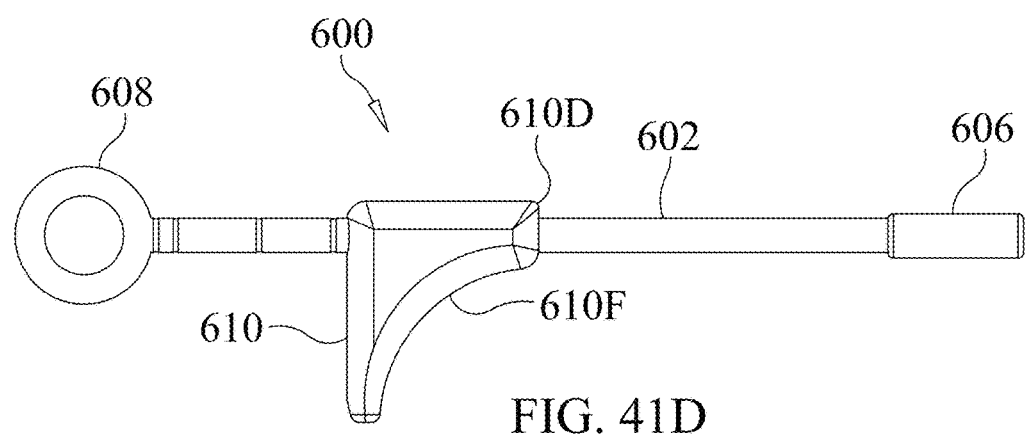
FIG. 41D shows a length sizing instrument according to another embodiment of the present invention.
Figure 41E:
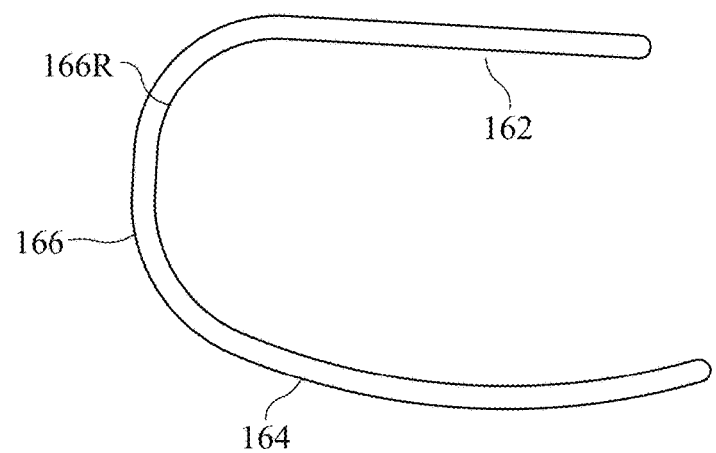
FIG. 41E illustrates a main body of a device, showing anterior, lateral and posterior segments of the main body, according to an embodiment of the present invention.
Figure 41F:
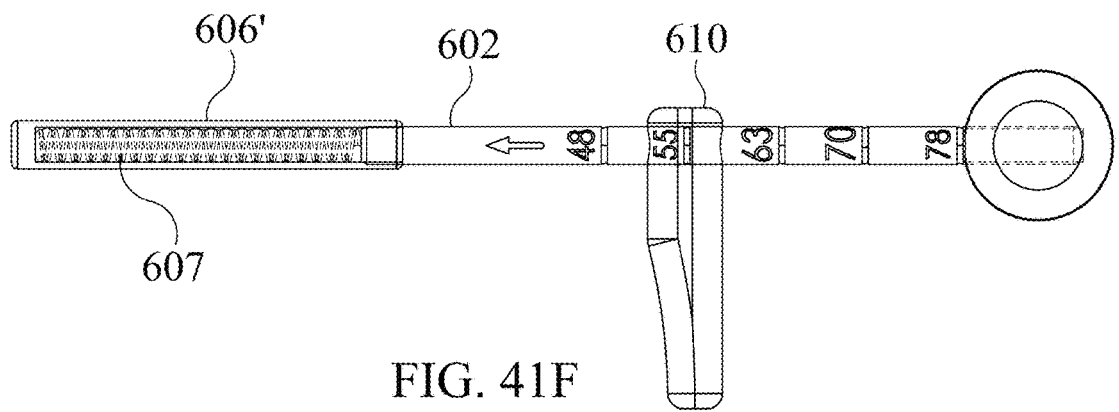
FIG. 41F shows a length sizing instrument according to another embodiment of the present invention.

Optionally the length sizing instrument 600 may include a measuring guide 610 that is slidable along the shaft 602, as shown in FIG. 41D. Measuring guide 610 can be used to identify the length measurement by inserting the tip 606 into the transverse sinus 14 as far as possible, without obstructing or potentially causing any damage to any structures that may lie in the path of the transverse sinus 14 and not to extend as far as to intersect with or obstruct the right atrium or tricuspid valve, in the same manner that the instrument of FIGS. 41A-41C is used. However, the measuring guide 610 helps to more accurately define where the anterior segment 162 will join the lateral segment 166 at the end of the transverse sinus 14 being measured, requiring less approximation by the user when reading the gradations on the shaft 602. The distal edge 510D of the measuring guide 610 can be used to identify the length of the anterior segment 162 needed by reading the gradation measurement that aligns with or is nearest to the distal edge 610D. The face 610F of the measuring guide 610 preferably has a radius of curvature that matches the radius of curvature of a lateral segment 166 of a device 10 in the vicinity of the lateral segment 166 where the lateral segment 166 joins the anterior segment 162, see 166R in FIG. 41E. In at least one embodiment, the radius of curvature in the plane of the drawing sheet on which face 610F is shown was about 17 mm. The radius of curvature of face 610F may be in a range from 14 mm to 20 mm, more preferably 15 mm to 19 mm even more preferably 16 mm to 18 mm. Accordingly, after inserting the tip 606 as far into the transverse sinus as indicated above, the measuring guide 610 can then be slid distally relative to the shaft until face 610F contacts the heart tissue in substantially the same location that the portion of lateral segment 166 connected to the anterior segment 162 will contact the heart when the clip 10 is installed. Next a length measurement can be made by reading the graduated marking that is closest to the distal edge 610D.

Figure 42:
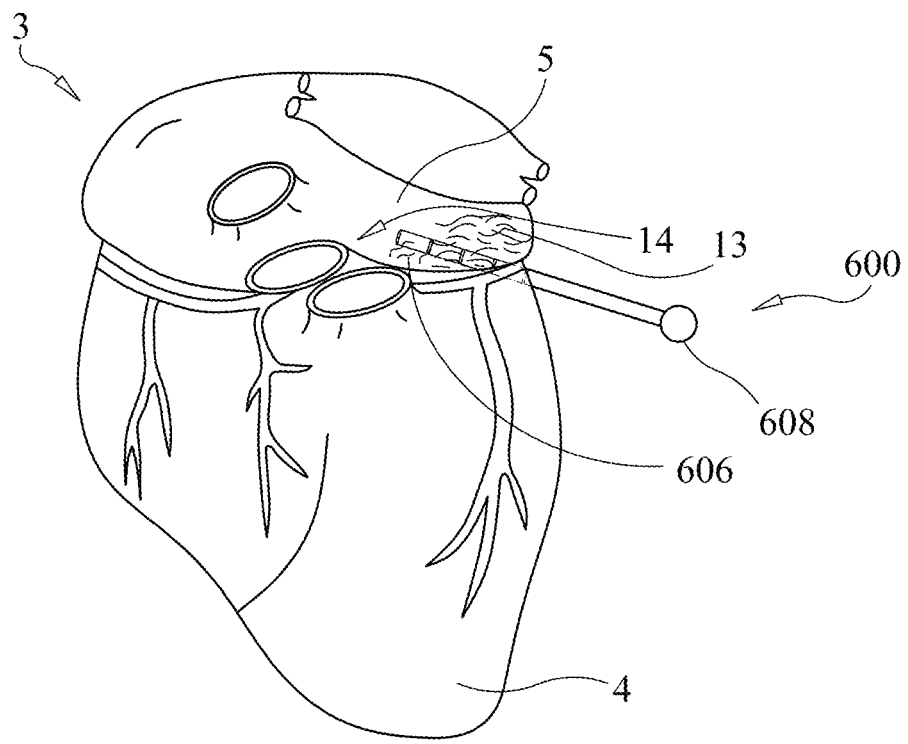
FIG. 42 illustrates insertion of a length sizing device into the transverse sinus of a heart to make a length sizing measurement, according to an embodiment of the present invention.

FIG. 42 illustrates insertion of a length sizing device 600 into the transverse sinus 14 of a heart 3 of a patient to be treated for mitral valve regurgitation. The user typically grips the instrument 600 via handle 608 and gently inserts the atraumatic tip 606 of the instrument through the opening of the transverse sinus 14. While carefully advancing the tip 606/instrument 600 into the transverse sinus 14, pressure may be applied against the shaft 602 toward the heart wall so as to keep the shaft 602 as far against the wall and the interior wall of the transverse sinus 14 as practical, as this will be the most secure location for the anterior segment 162. The instrument 162 is advanced until the usable end of the transverse sinus 14 (e.g., where the transvers sinus veers to the left at the location of the right atrium) is abutted by the atraumatic tip 606 or until the atraumatic tip 606 abuts a structure that extends into the transverse sinus 14. At this time, the graduated scale 604 is read by the user to measure the usable length of the transverse sinus. Alternatively, if the instrument 600 includes the measuring guide 610, the measuring guide 610 is slid to contact the face 610F to the surface of the heart at this time, after which the graduated scale 604 is read with the assistance of the distal edge 610D. For example, if the graduated scale reads 55 mm at the opening of the transverse sinus/edge 610D, then a device/clip 10 having the longest anterior segment that is not greater than 55 mm would be selected for use in this case. Thus, if devices 10 having anterior segment 162 lengths of 45 mm, 53 mm and 63 mm and 70 mm were available for selection, the device having the anterior segment length 162L of 53 mm would be selected for use in this case.

Once a preferred size (width 160 and length 162L) of device 10 has been selected, the anterior segment 162 can be inserted into the transverse sinus 14 and the posterior segment 164 can be positioned in the correct location on the posterior wall of the heart 3 identified during the width sizing procedure, and the posterior segment 164 can be anchored to the position with tissue anchors, tacks or the like, either driven through pad 56, or a flap extending from the pad. Optionally, the anterior segment 162 may also be anchored in the transverse sinus using tissue anchors, tacks or the like, inserted through a flap extending from the anterior segment 162.

Figure 43A:
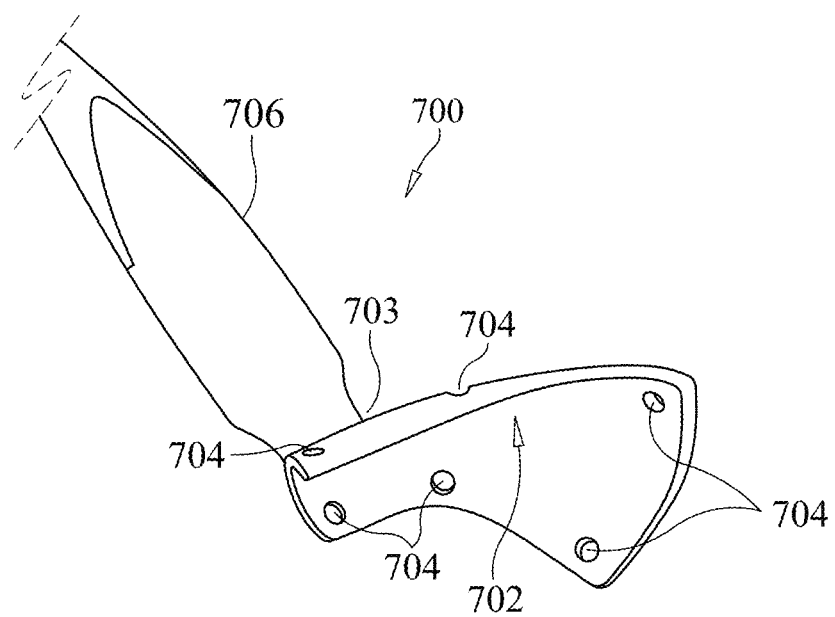

FIGS. 43A-43B show two different perspective views of an implant insertion cradle 700 according to an embodiment of the present invention. Implant insertion cradle may be made of any of the metals identified in this disclosure or of rigid plastic. Implant insertion cradle includes an implant interface surface 702 that has a concave conformation configured to match the convex curvature of a portion of the lateral segment 166 that it is designed to be attached to. A plurality of attachment features 704 are provided on or through the implant interface surface 702 to facilitate releasable attachment of the implant insertion cradle 700 to device 10' or 10 or a portion of 10. In the embodiment of FIG. 43A the attachment features are three pairs of suture holes 704 through which sutures 704S (FIG. 43C) can be threaded, wherein the sutures 702S can be further threaded around the device 10', 10 or portion of 10, to releasably fix the same to the implant insertion cradle 700. Of course the present invention is not limited to the use of three pairs of suture holes 704 and three sutures 702S, as more than three or even two could be used. Further alternatively, the attachment features could be other than sutures and suture holes. For example, the implant interface surface could be designed with edge shoulders dimensioned to form a snap fit over the portion of the device 10, 10; that it joins with. Further alternatively, straps could be wrapped around both the distal end 703 and device 10, 10' portion to releasably secure the two together. Still other releasable attachment features could be substituted, as would be apparent to one of ordinary skill in the art. A rigid handle 706 extends proximally from the distal end portion 703 that includes the implant interface surface 702. The rigid handle 706 extends away from the distal end portion 703 at an angle that is nearly a right angle, typically at an angle in a range from 70 to 110 degrees.

FIG. 43D shows implant insertion cradle 700 attached to a device 10' in preparation for inserting it and installing it around the heart 3 in a manner as described above. The rigid handle 703 is extended by attachment of an extension handle 710 thereto. Extension handle includes a shaft 712 that attaches to the handle 706 and a handle portion 714 that extends distally from the shaft 712 and has a larger cross-sectional area than that of the shaft to facilitate easier grasping thereof by a user. The shaft may be bendable or malleable to allow the angle of the shaft 710 relative to the shaft 706 to be changed, but should be sufficiently rigid so that it does not bend under the forces exerted upon it during a normal insertion procedure of the device 10. FIG. 43E is an enlarged view of the portion of FIG. 43D within box 43D. FIG. 43E shows the close conformity of the interface surface 702 to the curvature of the lateral segment 166. FIG. 43E further shows the sutures 704S wrapping around the lateral 166 segment to secure it to the distal end portion 703 of the implant insertion cradle 700. Implant insertion cradle facilitates delivering the device 10' (or lateral segment 166 of segmented device 10, for example) to the heart 3 and can be further used to manipulate the device 10, 10' or portion of 10' or 10" or 10''' to properly place it on the locations of the heart 3 that have already been described. Once the user has determined that the cradle 700 is no longer needed to continue the procedure, the cradle 700 is disconnected from the lateral segment 166 and withdrawn from the surgical site and patient. In the embodiment shown, where sutures 704S are used to secure the cradle 700 to the device 10', the user simply cuts the sutures 704S and then withdraws the cradle 700 and sutures 704S from the patient.

Figure 44A:
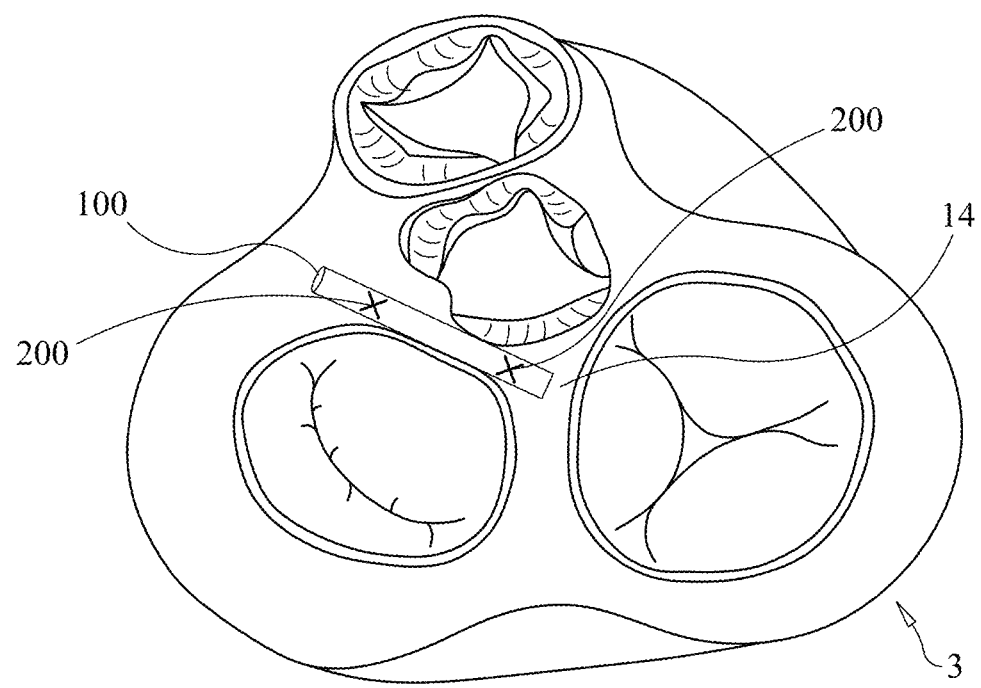
FIGS. 44A-44D schematically illustrate events that may be carried out during an implantation of a device according to an embodiment of the present invention.

FIGS. 44A-44D schematically illustrate events that may be carried out during an implantation of a device 10 according to an embodiment of the present invention. Initial measurements to determine a length of the anterior segment 162 and a distance 160D between the anterior segment 162 and the posterior segment 164 can be made in the same manner as described above, using any of the instruments and techniques described above with regard to FIGS. 39-41D. Once length and distance measurements have been made and a device 10 having the appropriate length and distance characteristics has been selected, sleeve 100 is anchored in the transverse sinus 14 as illustrated in FIG. 44A. Note that sectional views of the heart 3 are shown, absent the atria, for clearer identification of the implant sites. The sleeve 100 can be anchored by driving fixators 200 directly through the bottom wall of the sleeve 100 as illustrated in FIG. 44A, or by anchoring a flap 185, that is attached to the sleeve, to the bottom of the transverse sinus 14 and into the trigones 14T. Any of the fixator drivers described herein that can drive a fixator 200 in a direction normal to the longitudinal axis of the fixator driver can be used to anchor the sleeve 100 in the transverse sinus. The sleeve 100 can be cut to a desired length at this time, if needed.

Having already marked the posterior wall of the left ventricle 4 during the distance measurement procedure, the heart 3 is next lifted out of the chest of the patient to expose the posterior surface of the left ventricle. The pad 56 and flap 85 are positioned in alignment with the markings having been previously made and then a fixator driver is used to drive fixators 200 into the flap 85 and underlying heart tissue to anchor the flap 85, and therefore also the pad 56 to the posterior surface of the left ventricle 4, see FIG. 44B. Any of the fixator drivers described herein can be used to drive the fixators 200 into the flap 85.

Figure 44B:
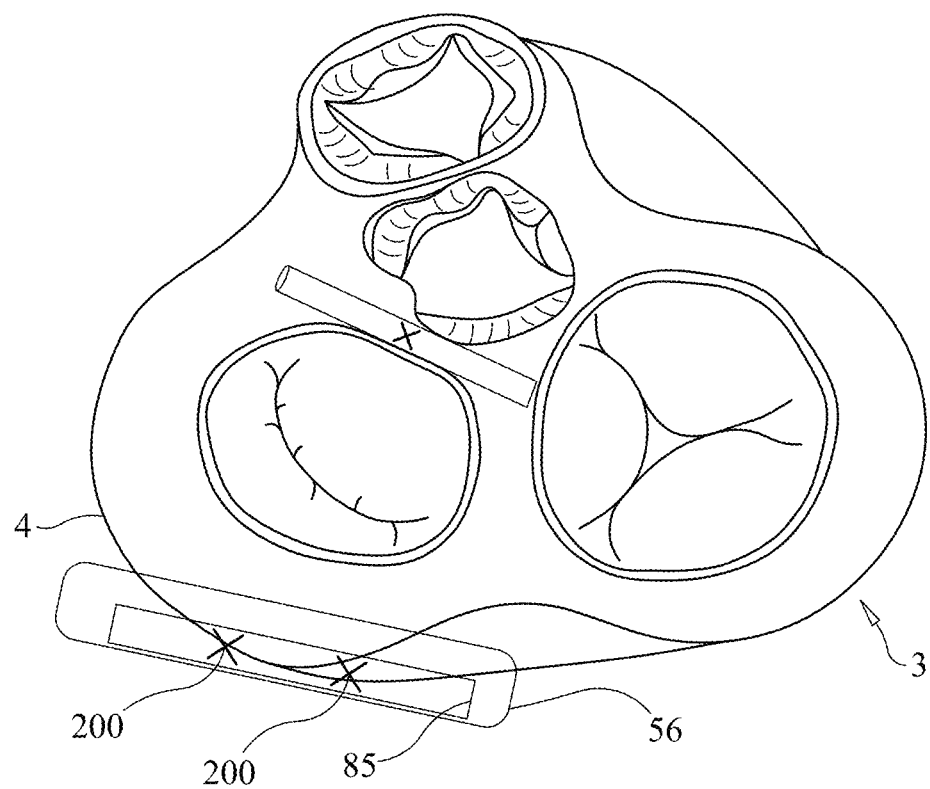
Figure 44C:
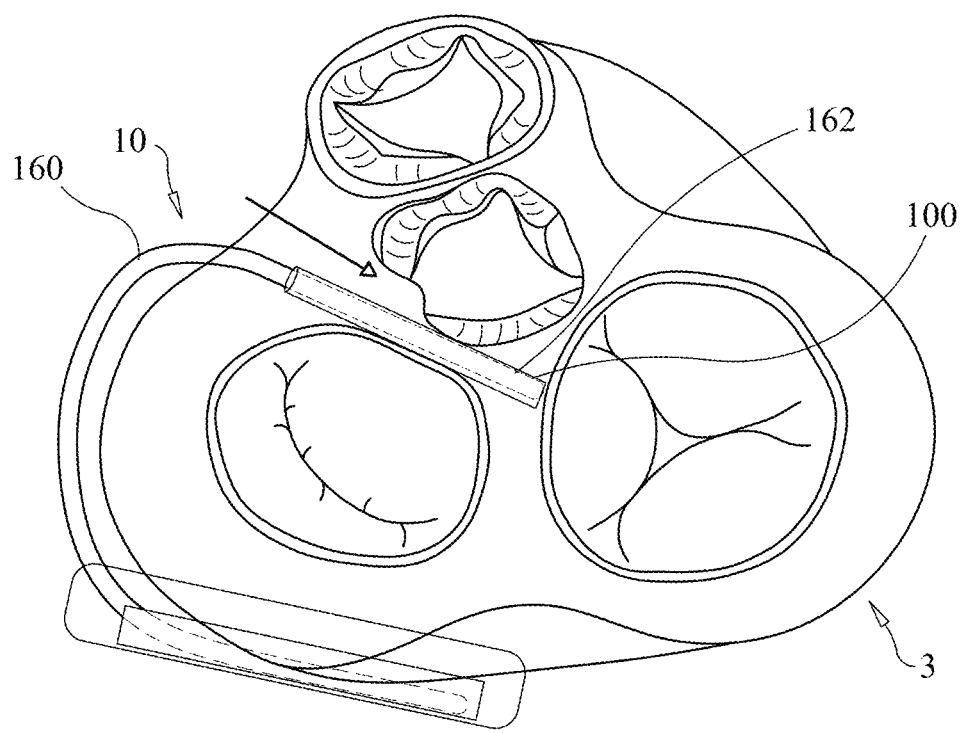

At FIG. 44C, the main body 160 of the device 10 is next delivered to the surgical target location, where the anterior segment 162 is inserted into the sleeve 100. The anterior segment 162 is preferably inserted all the way into the sleeve 100 until it abuts the closed end of the sleeve. Optionally, the implant insertion cradle 700 can be fixed to the main body 160 and used to insert it both to the location of the heart and to insert the anterior segment 162 into the sleeve 100.

Figure 44D:
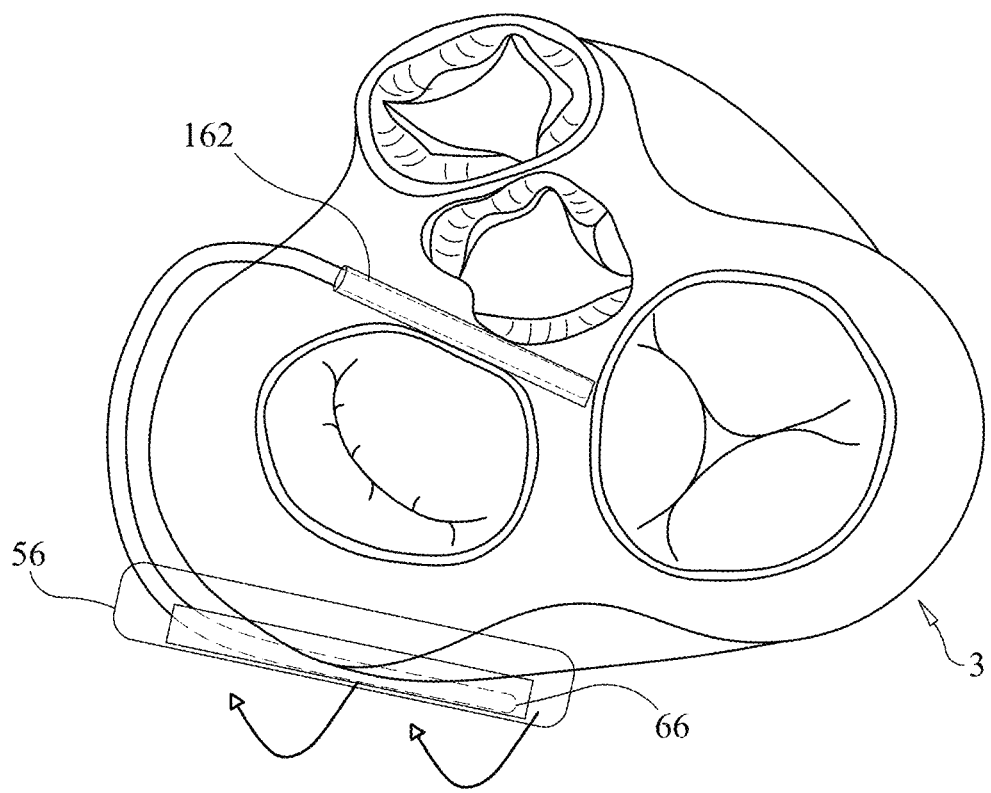

Next, at FIG. 44D the main body 160 is rotated about the longitudinal axis of the anterior segment 162 to rotate the posterior segment 164 down past and inferior to the engagement feature 66. Once the posterior segment 164 is inferior to the engagement feature it moves inwardly toward the heart and is rotated slight upwardly to be captured by the engagement feature 66, as illustrated in FIG. 44D.

Figure 45A:
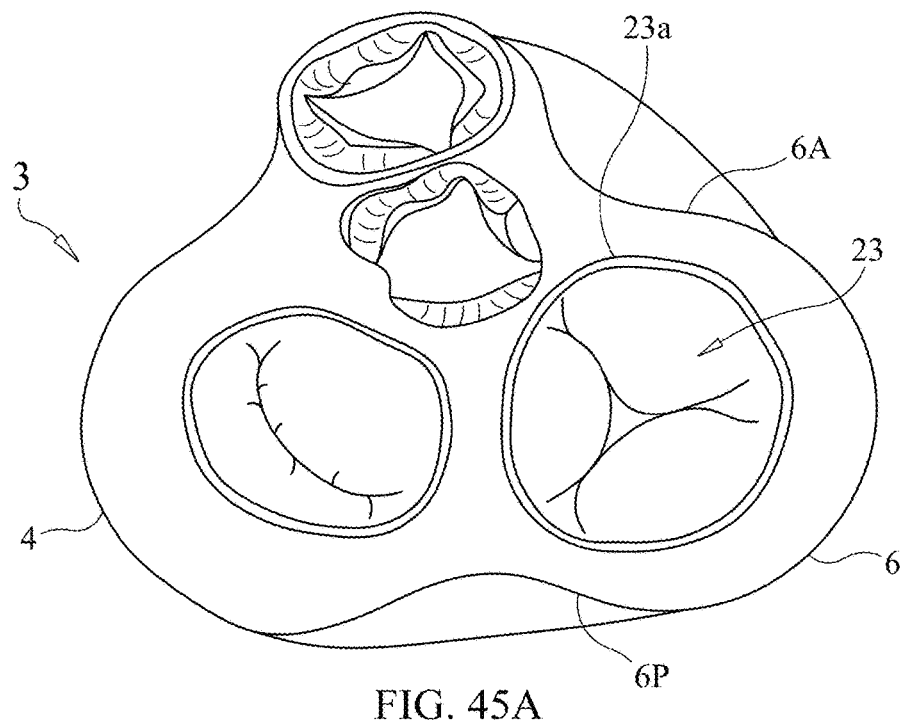

FIGS. 45A-44B schematically illustrate events that may be carried out during an implantation of a device 10" according to an embodiment of the present invention. Optionally, an initial measurement to determine a distance between an epicardial surface 6P of the posterior wall of the right ventricle at a level in or about a plane of the tricuspid valve 23 and an epicardial surface 6A of the anterior wall of the right ventricle 6 at a level in or about the plane of the tricuspid valve 23 can be made in a manner like that described above when measuring the distance 160D for use on the left side of the heart, using any of the instruments and techniques described above with regard to FIGS. 39-41K, except the forces applied are forces to the right ventricle 6 to measure the distance needed for treatment of the tricuspid valve 23. Alternatively, this measurement step can be skipped. In either case, the device 10" that is implanted for the treatment can be adjusted during or after implantation to change the amount of force/displacement of the wall of the ventricle 6 and thus to the annulus of the tricuspid valve. During this force adjustment, visualization, such as by transesophageal electrocardiography (TEE), for example, can be used to monitor the tricuspid valve 23 and visualize the amount of regurgitation therethrough, to determine when the optimum amount of force/displacement has been reached.

Figure 45B:
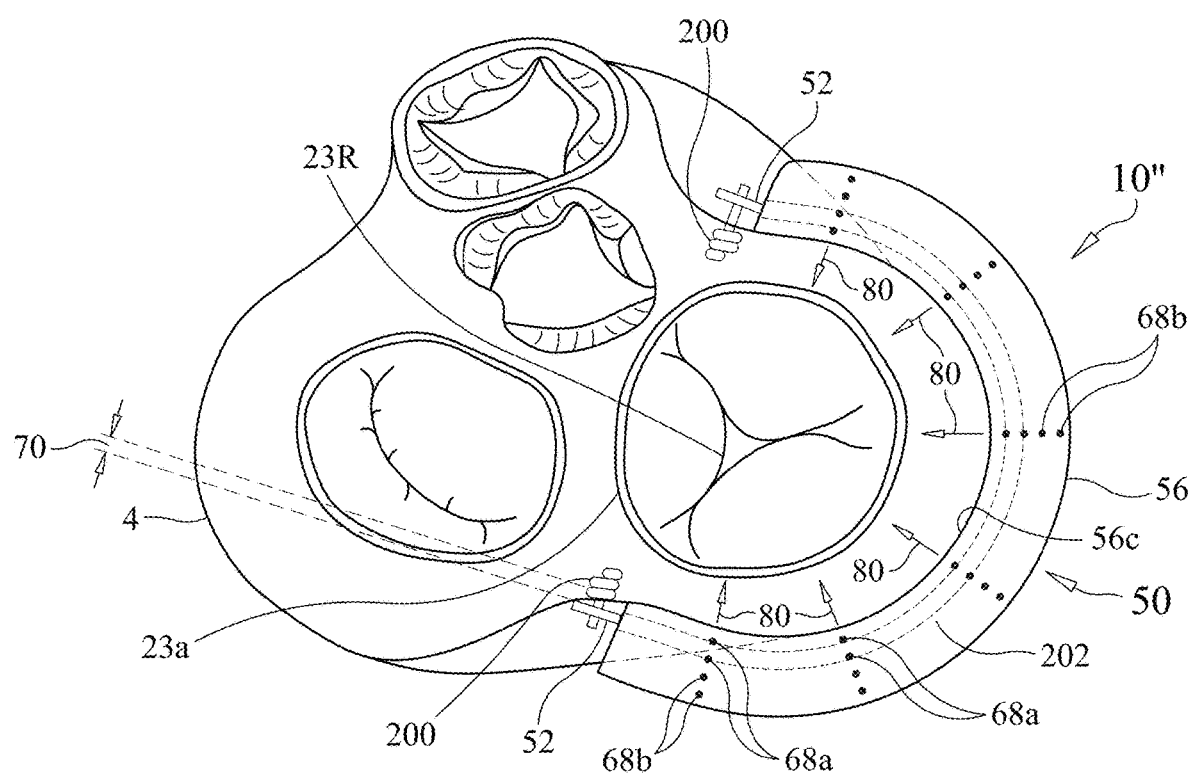

Once a distance measurement has been made, if that option is chosen, a device 10" having appropriate distance characteristics is attached epicardially, in or about the plane of the tricuspid valve 23, as illustrated in FIG. 45B. FIG. 45B illustrates device 10" having been installed epicardially on the heart 3 of a patient for treatment of tricuspid valve regurgitation as one of the preferred embodiments of location of implantation. In this preferred embodiment, device 10" can be installed epicardially on the heart 3 over a target location to effect reshaping of the tricuspid valve annulus 23a. The device 10" (as well as the device 10'" of FIG. 46) can be installed with the fixators 200 pre-mounted to the device so that the device is attached to the target tissue simultaneously with the anchoring of the fixators 200. Alternatively the fixators 200 can be anchored prior to introducing the device and the device can subsequently be attached to the implanted fixators 200 to anchor the device to the target tissue. Preferably, the contact pad 56 of the device is as long as can be fitted to the heart 3 at this location, so that the contact surface 56C of the pad contacts the heart wall around as much of the tricuspid valve annulus 23a as possible. FIG. 45B shows that the pad 56 of the device 10" surrounds greater than 50% of the annulus 23a and can apply forces to three sides of the heart wall (anterior, posterior and lateral). Preferably the pad 56 extends as far as is physically possible before it is prevented by heart structures from extending any further. Thus, the pad may surround a percentage of the annulus in a range from 30% to 70%, preferably 40% to 70%, more preferably 50% to 70%, even more preferably 60% to 70%. The device 10" may be anchored to the wall of the heart at the level of the tricuspid valve 23 via fixators 200 in a manner as described with regard to previous embodiments described.

Rod/rib 202 extends through the main body 50 of device 10" and forms extension rods 52 that extend from both ends of main body 50. Rod/rib 202 is preferably substantially curved as shown, with a curvature configured to conform to the curvature of the epicardial walls of the right atrium 6 at the level of the tricuspid valve 23 and extend around the tricuspid valve as far as the heart structure allows without obstructing the placement thereof. The main body is formed by pad 56 which surrounds or encases the portion of the rod/rib 202 extending therethrough.

Extension rods 52 can be configured to engage with fixators 200. Optionally, one or more fixators 200 could be applied through the pad 56, intermediate the ends of the device 10" to further secure the device 10" to the tissue. As noted above, rod/rib 202 (which includes extension rods 52) is rigid. By rigid, what is meant is that the rod/rib 202 has sufficient rigidity to maintain its shape without deformation under normal operating conditions. Thus, application of a typical external force on the rod/rib 202, such as forces applied by the beating heart in embodiments installed on the heart, will not appreciatively alter the shape thereof. The accumulated mechanical loads for reshaping the heart are dominated by the filling pressure of the right side of heart which is often below 60 mmHg and right atrial pressures below 20 mmHg. For example, in some embodiments an external force of 5 Newtons or less, 10 Newtons or less, 15 Newtons or less, 20 Newtons or less, or 25 Newtons or less applied to the rod/rib 202 would not result in appreciable deflection, deformation or bending thereof. Furthermore, the rod/rib 202, unlike a cord or cable, may be capable of withstanding axially compressive forces without collapsing and/or may be capable of withstanding bending forces without deflection. In some embodiments, the rod/rib 202 may have a modulus of rigidity (bending and/or compression) of greater than 25 GPa, greater than 30 GPa, greater than 40 GPa, greater than 50 GPa, greater than 60 GPa, greater than 70 GPa, or greater than 80 GPa.

In some embodiments, the extension rod portions 52 of the rod 202 may be curved or straight. In some embodiments the contact surface 56c and rod 202 may have a curvature approximating the curvature of the external curvature of a wall of a heart. In some embodiments, the extension shafts 52 may be eliminated altogether, such that the main body 50 extends over the lengths occupied by the extension shafts 52 in FIG. 45B.

In FIG. 45B, the rod/rib 202 is shown captured by the stops 68a, such that the normal distance measurement between rod/rib 202 and the location of the contact surface 56C is 70 and a force 80 applied to the external wall of the heart 3 results in a deformation of the heart wall and annulus 23a of the mitral valve 23. Note that forces 80 are applied all along the heart wall where the contact surface 56C extends. For exemplary purposes, FIG. 45B illustrates that the valve leaflets of the tricuspid valve 23 have not been completely closed by this reshaping of the tricuspid valve annulus 23a, where a small separation 23R remains between the leaflets to allow some tricuspid valve regurgitation.

Figure 45C:
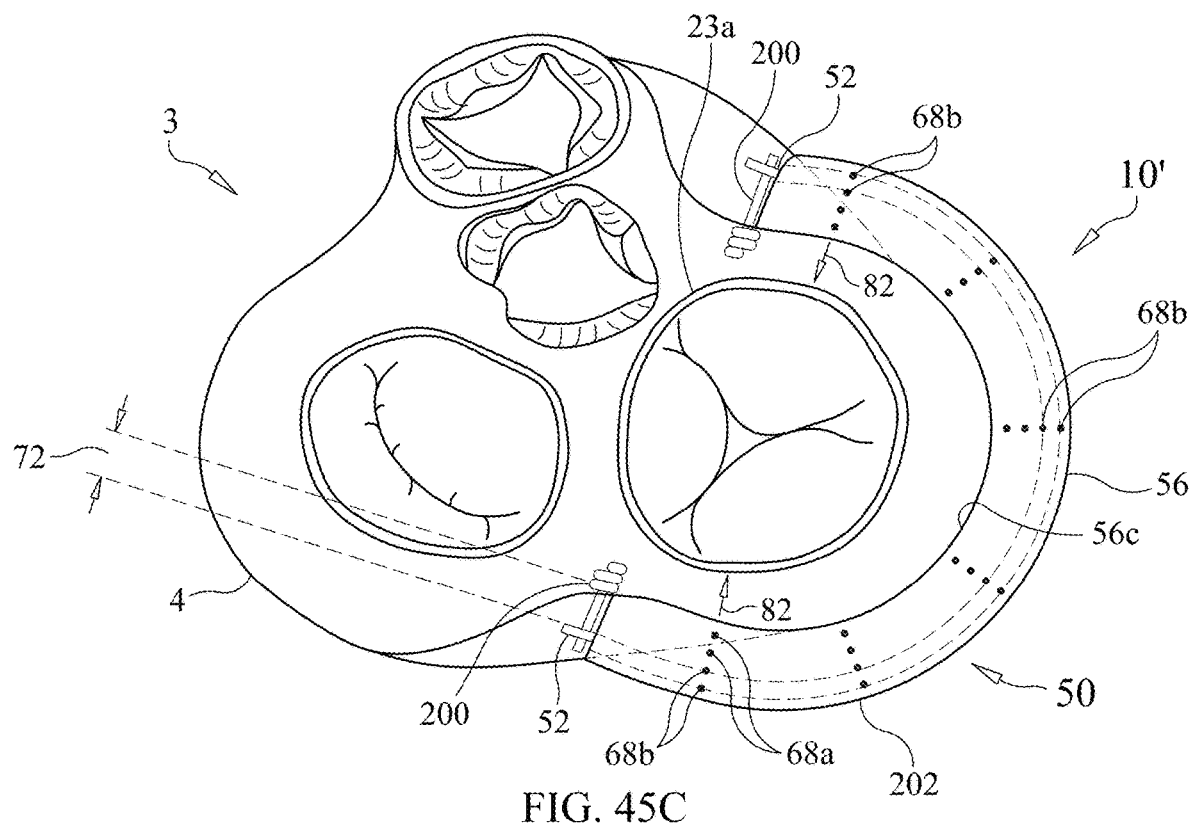
FIG. 45C illustrates the implanted device of FIG. 45B, after manual adjustment of the device, according to an embodiment of the present invention.

FIG. 45C illustrates the implanted device 10" of FIG. 45B, after manual adjustment of the device to move rod/rib 202 relative to pad 56 so that rod/rib 202 is captured by stops 68b. After this adjustment the normal distance measurement between rod/rib 202 and the contact surface 56C is 72 and this greater distance (relative to distance 70) results in application of a force 82 that is greater than force 80 applied to the external wall of the heart 3, therefore resulting in greater deformation of the heart wall and annulus 23a of the mitral valve. Also, because the distance 72 is greater than 70 at both opposing locations 6A and 6P on the surfaces of the right ventricle 6 and because the distance between the rod portions at these locations does not change (due to the rigidity of the rod/rib 202) this results in the distance between the portions of the contact surface 56C at locations 6P and 6A being less than it was in FIG. 45B by an amount of 2(72−70) and therefore the tricuspid annulus 23 is deformed due to the deformation of the ventricular walls surrounding it. Similarly, the change in position of the rod/rib 202 relative to the contact surface 56C by repositioning the rod/rib 202 in the stops 68b at the intermediate locations cause an increase in force and deformation applied to the heart wall and tricuspid annulus apposite the intermediate locations. As illustrated in FIG. 45C this greater deformation/reshaping of the annulus 23a has resulted in the complete closing of the valve leaflets of the tricuspid valve 23 so that tricuspid valve regurgitation no longer occurs.

Figure 45D:
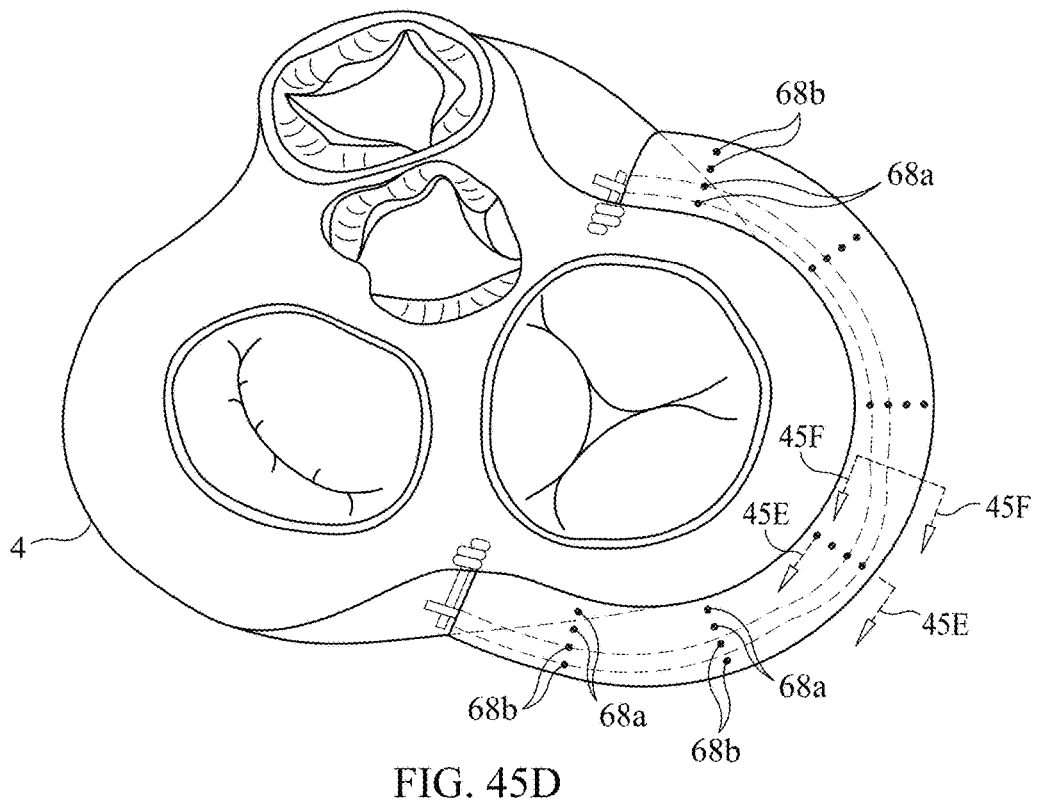
FIG. 45D illustrates the implanted device of FIG. 45B after a manual adjustment of the device that differs from the manual adjustment shown in FIG. 45C.

It is further noted that the device 10" is not limited to the amount of adjustment provided by the change in position of the rod/rib 202 from that shown in FIG. 45B to that shown in FIG. 45C and vice versa. Further variations in forces applied, and distances between opposing contact surfaces can be achieved by various partial adjustments of the rod/rib 202 relative to the stops 68a and 68b. That is, any individual portion of the rod/rib 202 can be adjusted from positioning within stops 68a to positioning within stops 68b, independently from the positioning of all other portions of the rod/rib 202 relative to its corresponding stops. As just one example, FIG. 45D shows only the posterior portion of the rod/rib 202 having been repositioned in the channel to be held by stops 68b, while the portions of the rod/rib 202 that apply forces at the anterior wall are positioned in the stops 68a in the channel, as are the portions of the rod/rib 202 intermediate of the posterior and anterior portions. In this instance, the reduction in distance between the contact surfaces 56C at 6P and 6A is only the difference between distance 72 and distance 70. However, in this instance, this was sufficient reduction to close the tricuspid valves and eliminate tricuspid valve regurgitation as illustrated in FIG. 45D. As noted, there are many other combinations of modification of relative positioning of the rod/rib in each of the sets of stops provided, so that the force profile about the tricuspid valve, to the extent that it is surrounded by the device 10" can be customized.

FIG. 45E is a cross-sectional illustration of the device 10" of FIG. 45D taken along line 45E-45E, along the location where some of the stops/restrictions 68a, 68b are located. FIG. 45F is a cross-sectional illustration of the device 10" of FIG. 45D taken along line 45F-45F, along a section where no restrictions/stops 68a, 68b are located. Thus, FIG. 45F illustrates the full depth/thickness of the channel 66 that extends through the pad 56 for location of the rod/rib 202 and shows the restricted depth/thickness of the next set of stops (in phantom) further along the length of the channel 66. As shown in solid lines in FIG. 45E, the restrictions/stops 68a, 68b reduce the depth (thickness) of the channel 66 to a depth/thickness that is sufficiently less that the diameter of the rod/rib 202 to retain it between the stops 68a or 68b, wherein a force required to move the rod/rib 202 from a location captured by stops 68a to a location captured by stops 68b or vice versa is greater than a force that will be applied by the contact surface 56C of the pad 56 against the wall of the heart when the device 10' is in use. However, the force required to move the rod/rib 202 from one predefined location (e.g., 68a or 68b) to another predefined location (e.g., 68b or 68a, respectively) is one that can be readily exceeded by manual application of forces by a surgeon or other person involved in installation of the device 10". Further details about manually adjustable devices such as 10" can be found in U.S. application Ser. No. 16/258,519, titled "Manually Adjustable Device", filed on Jan. 25, 2019. U.S. application Ser. No. 16/258,519 is hereby incorporated herein in its entirety, by reference thereto.

FIG. 46 illustrates a device 10''' having been installed epicardially of the heart 3 of a patient for treatment of tricuspid valve regurgitation according to an embodiment of the present invention. Like device 10", a measurement between the anterior and posterior locations 6A and 6P of the right ventricle can optionally be made, during visualization of the tricuspid valve 23 to watch for regurgitation amounts occurring under various force and deformation levels, so as to identify an optimum distance between the contact surfaces 56c of the device that will be applied to the locations where the measurement was taken. Alternatively the device 10''' can be installed without taking the preliminary measurement and the device 10''' can then be adjusted under visualization to reduce and/or eliminate tricuspid valve regurgitation. This adjustment after implantation can be performed whether or not the preliminary measurement has been taken. As with the device 10", the device 10''' is attached epicardially, in or about the plane of the tricuspid valve 23, as illustrated in FIG. 46. FIG. 46 illustrates device 10''' having been installed epicardially on the heart 3 of a patient for treatment of tricuspid valve regurgitation as one of the preferred embodiments of location of implantation. In this preferred embodiment, device 10''' can be installed epicardially on the heart 3 over a target location to effect reshaping of the tricuspid valve annulus 23a. Preferably, the contact pad 56 of the device is as long as can be fitted to the heart 3 at this location, so that the contact surface 56C of the pad contacts the heart wall around as much of the tricuspid valve annulus 23a as possible. FIG. 46 shows that the pad 56 of the device 10''' surrounds greater than 50% of the annulus 23a and can apply forces to three sides of the heart wall (anterior, posterior and intermediate between the anterior an posterior walls). Preferably the pad 56 extends as far as is physically possible before it is prevented by heart structures from extending any further. Thus, the pad may surround a percentage of the annulus in a range from 30% to 70%, preferably 40% to 70%, more preferably 50% to 70%, even more preferably 60% to 70%. The device 10''' may be anchored to the wall of the heart 3 at the level of the tricuspid valve 23 via fixators 200 in a manner as described with regard to previous embodiments described.

Rod/rib 202 is provided in two parts, an first part 202a and a second part 202b that, extend through the main body 50 of device 10''' and form extension rods 52 that extend from both ends of main body 50. Rod/rib portions 202a, 202b are preferably substantially curved as shown, with a curvature configured to conform to the curvature of the epicardial walls of the right atrium 6 at the level of the tricuspid valve 23. The main body is formed by pad 56 which surrounds or encases the portion of the rod/ribs 202a, 202b extending therethrough. As shown, the portions 202a, 202b are about equal in length, but this need not be the case. In FIG. 46, the portions 202a, 202b are joined together by an actuator 206, which may be a gearbox, one-way ratchet mechanism, or other mechanical component that allows the portions 202a, 202b to be driven therethrough in at least one direction. By driving the portions 202a, 202b through actuator 206, this effectively decreases or increases the distance between the contact surfaces 56C contacting the anterior and posterior walls 6A and 6P of the heart 3 on opposite sides of the tricuspid valve 23 as illustrated in FIG. 46. For example, by relatively driving the portions 202a, 202b so that 202b moves upward through the actuator 206 and or 202a moves downward through the actuator 206 in FIG. 46, this causes the distance between contact at 6A and 6P to be reduced, thereby increasing the force and deformation on the walls of the heart 3 and on annulus 23a. Of course, movement in the opposite directions would have the opposite effect of reducing the force and decreasing the deformation, Actuator 206 may be manually adjustable, particularly in the directions for increasing the force/deformation, by manually forcing the ends of the device toward one another so that the described movement occurs. In the case of a one way ratchet mechanism, the mechanism would then prevent the ends from moving away from the new positions. Actuator 206 may be a motorized gearbox, with battery power, for example, which could be actuated either directly by an actuation switch on the device 10''', or preferably can be configured for remote wireless actuation. The motorized actuator 206 can be actuated to either increase or decrease the forces/deformation applied by the device 10''' to the heart 3.

Figure 47:
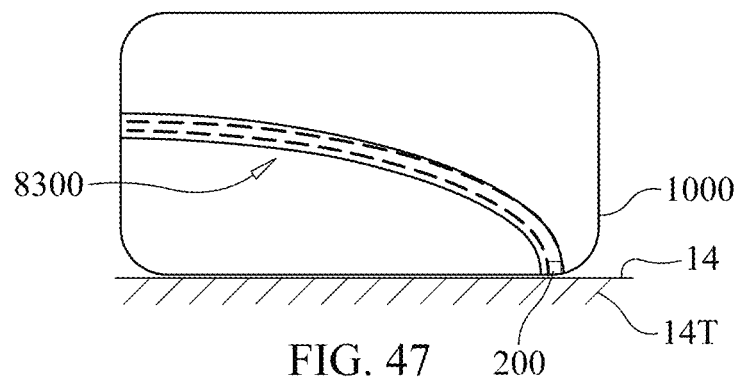
FIG. 47 schematically illustrates a high torque wire configured to drive a fixator into the floor of the transverse sinus, according to an embodiment of the present invention.

FIG. 47 schematically illustrates high torque wire 8300 configured to drive a fixator 200 into the floor of the transverse sinus 14, into the trigones 14T or "backbone" of the transverse sinus. As shown, this permits the fixator 200 to be orientated in the transverse sinus 14 to be deployed into the cartilaginous backbone 14T of the transverse sinus and away from the left atrium 5 and the aortic valve. The backbone 14T sits at the base of the transverse sinus 14 and allows good purchase from a fixator 200. The pad 1000 has minimal width (less than 2 cm) and a height (greater than 2 cm) that orientates one edge of the fixator 200 towards the base of the transverse sinus 14. The pad 1000 should have rounded edges to prevent trauma upon insertion and may be made from a variety of biocompatible rigid (steel, aluminum, titanium, Delrin, etc.) or a semi-rigid material (silicone, polyurethane, etc.). The high torque wire 8300 can be twisted within the pad 1000 to deliver the fixator 200. Multiple fixators 200 may be loaded into the pad 1000 for delivery. The torque wire 8300 could be replaced by any mechanism that allows for rotation to be delivered across a distance in a direction perpendicular to the insertion angle of the fixator, such as some of the fixator drivers already described above. For further examples, a right hand screw would work and so would a worm gear. The fixator 200 can be made from a number of biocompatible materials including steel, aluminum, titanium or a bioabsorbable polymer. The device may also include markers to allow imaging in various modalities. The device may also include imaging modalities such a CMOS chip or fiber optic cables or an IVUS catheter to ensure proper delivery location of the fixators 200.

Figure 48:
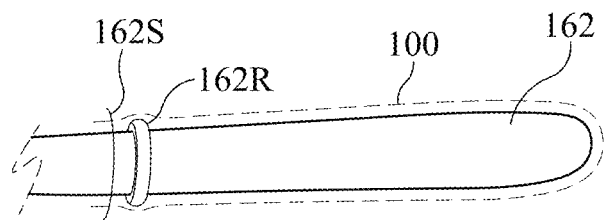
FIG. 48 schematically illustrates attachment of a sleeve to an anterior segment according to an embodiment of the present invention.
Figure 49:
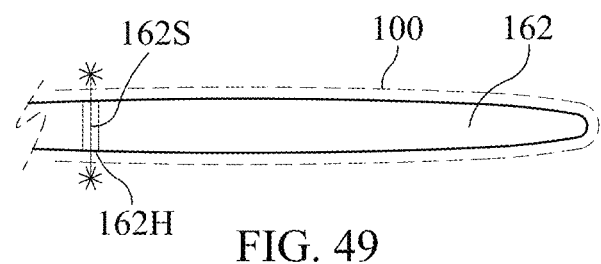
FIG. 49 schematically illustrates attachment of a sleeve to an anterior segment according to another embodiment of the present invention.
Figure 50:
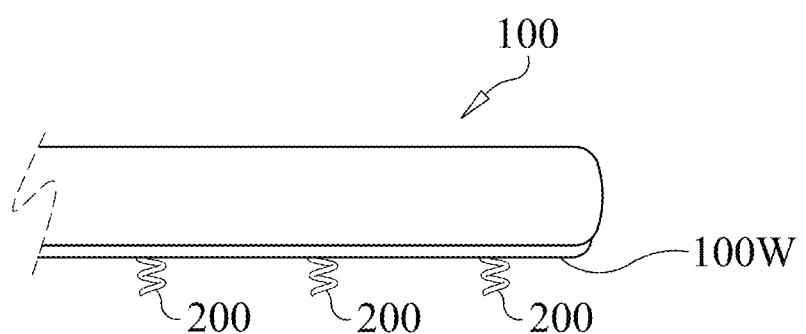
FIG. 50 illustrates a sleeve with a wire backbone and fixators attached to one side that can be deployed into the transverse sinus, according to an embodiment of the present invention.

The securement of the anterior arm 162 in the transverse sinus 14 within a fabric sleeve 100 has been described. This approach first secures the sleeve 100 to the base of the transverse sinus 14 and allows the anterior arm 162 to move relative to the sleeve 100 but minimizes movement relative to the sleeve 100 and the transverse sinus 14. This is accomplished by inserting a fabric (woven, knit or non-woven from materials such as but not limited to polyester, silk, polyurethane, polyvinylchloride, nylon, Teflon, Dacron, Orlon, and Lycra) sleeve 100 with a hollow space in the center (diameter at least as large the outside diameter of the anterior segment 162) into the transverse sinus 14 all the way to the right atrium, then securing it in place with one or more fixators 200, such as tacks, screws, hooks and/or glue, etc. Then the anterior segment 162 is inserted into the sleeve 100. A method to attach the sleeve 100 to the anterior segment 162 may be included, such as a method of tying a suture 162S around or adjacent to a ridge 162R provided in the anterior segment (see FIG. 48) or a suture through a hole 162H (see FIG. 49) in the anterior arm to keep it locked into the sleeve 100. Further alternative embodiments may include, but are not limited to: a sleeve 100 with a wire backbone 100W and one or more fixators 200 or hooks attached to one side that can be deployed into the transverse sinus 14, see FIG. 50; a backbone 100W that is partially flexible; a sleeve 100 that has a catch for the anterior segment 162 so that once inserted it cannot be removed; or a sleeve 100 that is glued to the base of the transverse sinus 14 instead of mechanically fixed or anchored thereto, or in addition to mechanical anchoring.

Although many of the above descriptions apply specifically to treatment of the mitral valve to reduce or eliminate mitral valve regurgitation, it is noted that many of these techniques and devices are applicable for treatment of other valves of the heart, such as the tricuspid valve, aortic valve or pulmonary valve for example, further to the specific descriptions already provided for treatment of the tricuspid valve, such as the descriptions for FIGS. 45A-46. For example a width sizing instrument could be made similarly to those described above, but to mimic forces applied by a posterior segment of a device (such as 10' or 10") to be used to treat tricuspid valve regurgitation, wherein force could be applied to a posterior wall of the heart adjacent the tricuspid valve and visualization techniques as described could be used to determine a width of a device to be selected for use in treating the tricuspid valve. As noted above a tricuspid procedure for epicardial annuloplasty may include two anchors and a bridging mechanism such as a backbone, e.g., rod/rib 202 or 202a, 202b. In addition to, or alternative to the adjustment features described above with regard to FIGS. 45A-46, a device may include an expandable member such as they type 56B described with regard to FIG. 1C above, or other expandable member. The adjustment feature provided may provide for step-wise adjustment perpendicular to the epicardial surface reducing the chord length between the two anchors on the end portions of the device and therefore reduce the tricuspid circumference to improve coaptation. Further additionally or alternatively, the device body or backbone may be adjustable parallel/tangent to the epicardial surface allowing reduction of the distance between the two or more anchors to reduce the tricuspid regurgitation.

Further optionally, with regard to the procedures described above for treatment of the mitral valve, a sleeve such as any of those described herein may be secured or anchored in the transverse sinus 14, by any of the techniques shown and/or described herein, prior to inserting the anterior segment 162 of any of the devices described herein into the sleeve/transverse sinus. Further optionally the sleeve may, but need not have a flap extending therefrom to be used for anchoring. The sleeve may be cut to a length measured by the length sizing instrument 600, or, alternatively, a plurality of sleeves having different lengths matching the anterior segment lengths 162L of devices may be provided in a kit.

As further noted, rather than providing a pad 56 integral with the posterior segment 164 as in device 10', a separate pad, such as shown in any of the embodiments of device 10 may be anchored to the posterior wall of the heart 3 in a location identified during the width sizing procedure, and a posterior segment can subsequently be hooked or otherwise attached to the separate pad using any of the techniques shown or described above.

Figure 51:
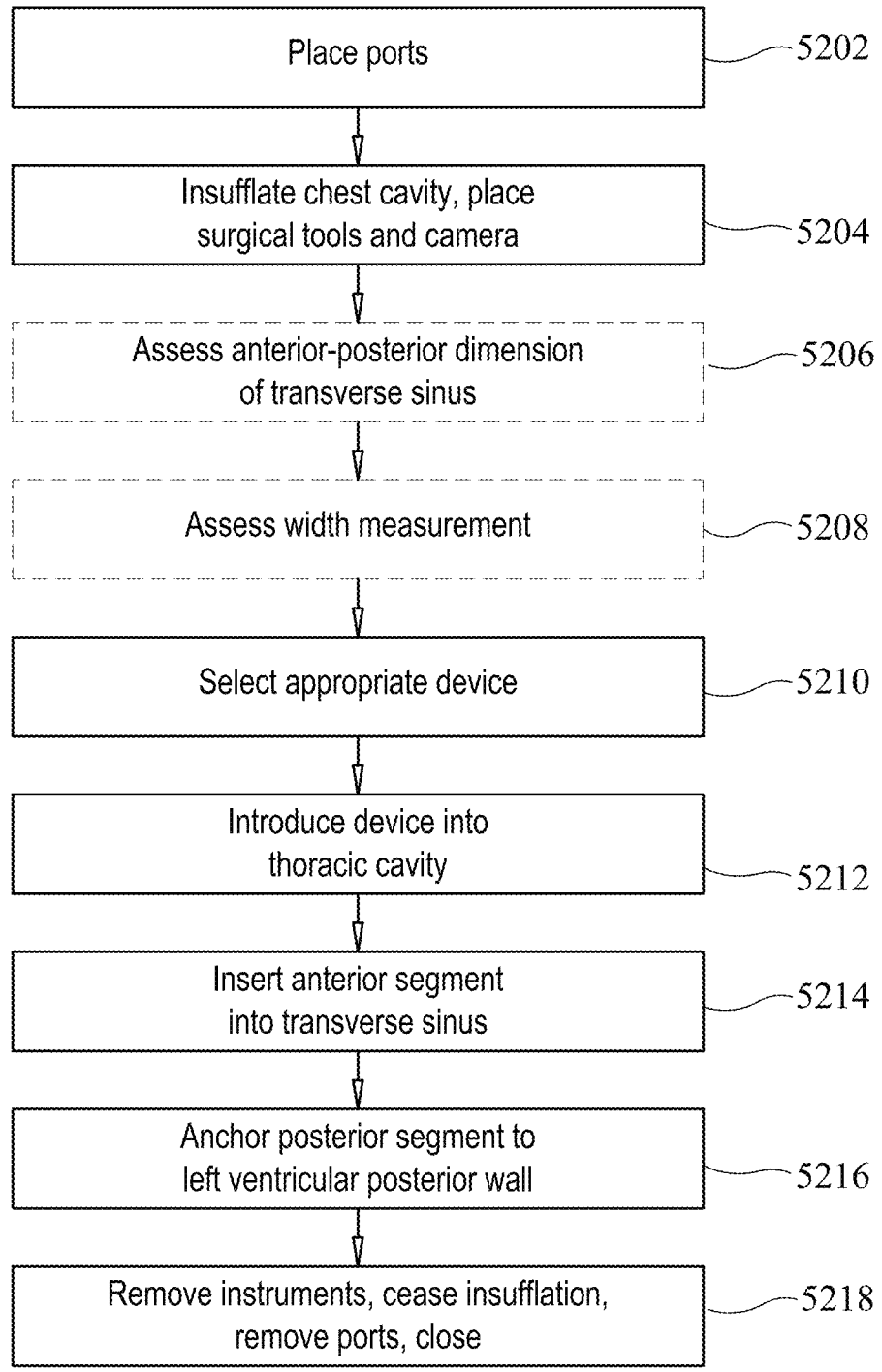
FIG. 51 illustrates events that may be carried out in the performance of a minimally invasive procedure for epicardial implantation of a device for treatment of valve regurgitation according to an embodiment of the present invention.

FIG. 51 illustrates events that may be carried out in the performance of a minimally invasive procedure for epicardial implantation of a device for treatment of valve regurgitation according to an embodiment of the present invention. Although this embodiment is specifically directed to a procedure for treatment of mitral valve regurgitation, it can be readily adapted to similar procedures for treatment of other valves, such as the tricuspid valve, aortic valve or pulmonary valve for example.

Figure 52:
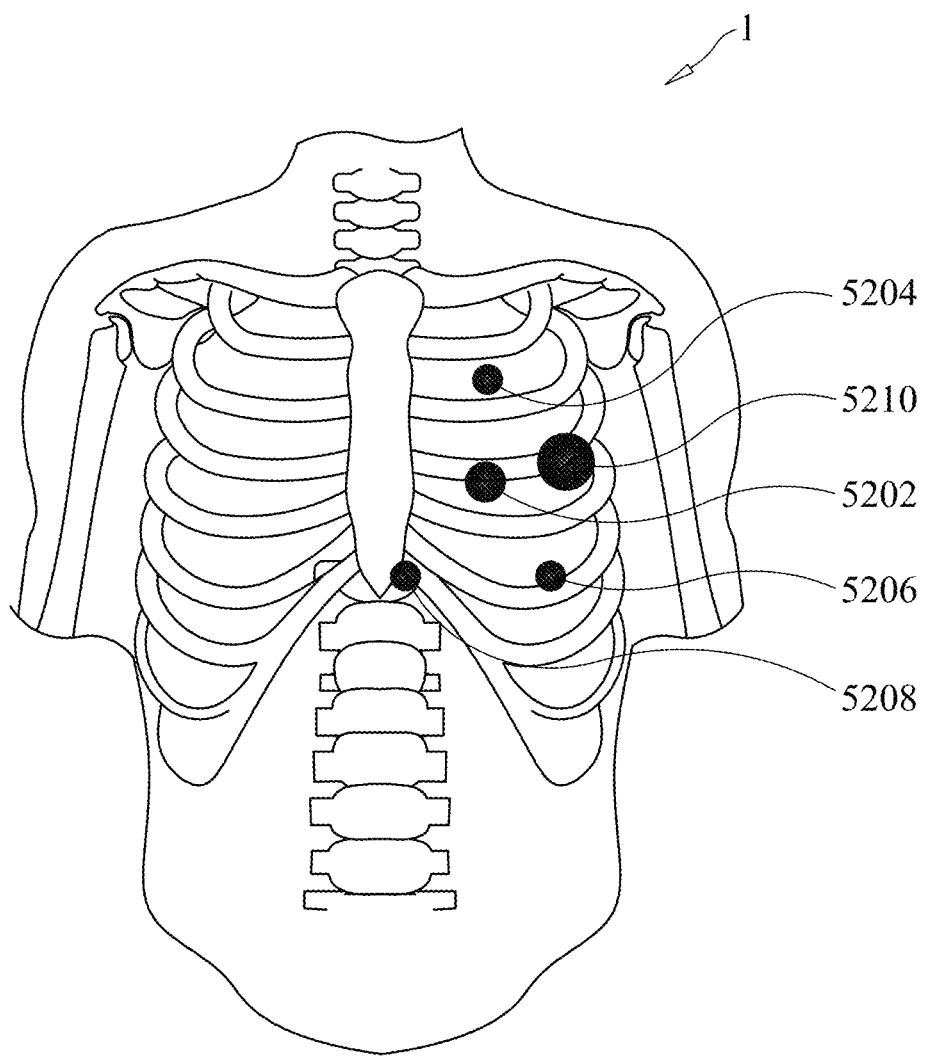
FIG. 52 illustrates locations of port placement in a patient for performing a minimally invasive procedure, according to an embodiment of the present invention.

At event 5102, ports are placed and trocars may be installed for facilitating the procedures that follow. FIG. 52 illustrates locations of port placement in a patient 1 according to one embodiment of the present invention. The port locations and number of ports are not to be considered limiting to the present invention, as the number and locations of the ports may vary. In the embodiment shown in FIG. 52, a camera port 5202, which may be a size 8 port is placed in the $4^{th}$ intercostal space, midclavicular line. A superior tool port 5204, which may be a size 6 port, is placed in the $2^{nd}$ intercostal space. An inferolateral tool port 5206, which may be a size 6 port, is placed in the $6^{th}$ intercostal space, midaxillary line. An inferomedial tool port 5208, which may be a size 6 port, is placed subxyphoid, and a device placement port 5210, which is sufficiently large to allow device 10' of FIG. 35A to pass therethrough, is placed in the $4^{th}$ intercostal space, midaxillary line. In a preferred embodiment, the device placement port 5210 may be an Alexis O Wound Protector/Retractor, available from Applied Medical. However, other ports having sufficient size and similar features may be substituted. Furthermore a smaller port 5210 may be used when the implantation procedure use device 10 as in FIGS. 1A-2B or a device using a main body 160M having separate segments 162M, 164M and/or 166M that can be assembled after they have been passed through the port and into the chest cavity.

At event 5104 the chest cavity of the patient 1 is insufflated and surgical tools and camera are placed through the appropriate ports. Insufflation may be to a pressure in a range of ten to fifteen atmospheres, for example. The pericardium is accessed and opened sufficiently to allow placement of the device 10' (or alternatively, another device as described herein). Optionally, event 5106 may be carried out to assess the anterior posterior dimension (usable length) of the transverse sinus 14, in order to provide a length measurement for the anterior segment 162 of a device to be implanted, as described in detail above. A length sizing instrument 600 can be inserted through one of the tool ports such as 5204 using graspers and manipulated via the graspers to insert it into the transverse sinus for measurement thereof. Using a robotic arm, the sizing tool 600 is grasped at its anterior dimension where it joins the end of the transverse sinus 14 and then the tool is withdrawn from the transverse sinus. The camera can be used not only for the procedures described previously, but also to read the anterior-posterior dimension, or length where the robotic arm grasps the tool 600 as indicated by gradations 604. The sizing tool 600 can then be withdrawn from the chest cavity using the graspers.

Optionally, a width measurement may be performed at event 5108 to assess a width 160D to use for selecting a device that has a width 160D that most closely matches the measurement. To perform this assessment, a width measuring instrument 500 may be placed through the device port 5210 and positioned and manipulated using handle 550 or 560. Forces are applied by the instrument 500, with repositioning as necessary, while visualizing the mitral valve as described previously to determine when the instrument 500 is positioned in the best location and with the best force applied for minimizing or eliminating mitral valve regurgitation. The width measurement can be made at this time using the same visualization techniques described above. After the width measurement has been determined, the instrument 500 can be removed from the chest cavity through the device port 5210.

At event 5110, a device is selected for implantation if it has not already been selected. In instances where one or both of the optional events 5106, 5108 are carried out, the device can be selected to have an optimum anterior segment 162 length and/or distance 160D from various devices that are available for selection and which have varying anterior segment lengths and distances 160D. At event 5112, the selected device is introduced into the thoracic cavity through the device port 5210, using implant insertion cradle 700 and/or graspers or forceps. The device port 5210 may be sealed with wetted gauze at the time of placement. If a width sizing procedure is performed (optional event 5108) then the wetted gauze can be removed at that time. If event 5108 is not performed, or if the wetted gauze was replaced after performing event 5108, then the wetted gauze is removed at this time to open the port 5210 to allow the device to be delivered therethrough. The device is typically angled in orientation to allow it to be passed through the port 5210. For example the device may be angled to insert the anterior segment 162 first. After passing the device through the port 5210, the wetted gauze may be replaced over the port 5210 to help maintain the insufflation pressure.

At event 5114 the device is manipulated via graspers, forceps and/or insertion cradle 700 to insert the anterior segment 162 into the transverse sinus 14. Visualization via the camera can be used to ensure that force on the transverse sinus 14 is directed toward the lateral wall. Optionally, transesophageal echocardiography (TEE) may be used to evaluate the left ventricle dimensions and ensure that left atrial perforation does not occur. At event 5116 the device is anchored to the left ventricular posterior wall, such as by use of fixators 200. For example a fixator driver such as 300, 3300", 5300 or 7300 may be used to anchor the posterior segment 164 to the left ventricular posterior wall, via insertion through one or both of tool ports 5206, 5208. The device may optionally be removed, if desired, by counter-rotating the fixators 200 to remove them and release the posterior segment 164 from its anchoring, rotating the posterior segment 164 out of contact with the left ventricle and retracting the anterior segment 162 out of the transverse sinus 14. The device can then be withdrawn out of the device port 5210 using an angled orientation like that used to first insert the device into the thoracic cavity through the device port.

At event 5118 after completion of the implantation procedure or completion of removal of the device, all instruments/tools are removed, insufflation is ceased, the ports are removed, and the patient is closed according to standard procedures to complete the surgical procedure.

While the present invention has been described with reference to the specific embodiments thereof, it should be understood by those skilled in the art that various changes may be made and equivalents may be substituted without departing from the true spirit and scope of the invention. For example, the invention can be used in other target tissues or organs, such as other valves of the heart, pulmonary tissues, the gastrointestinal system (including, but not limited to the stomach, small intestine, and/or large intestine), renal system, urinary system or any other tissues/organs that may be effectively treated with direct mechanical manipulation.

In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An epicardial device for placement on an epicardial surface of a heart in order to reshape an annulus of a valve of the heart, the epicardial device comprising:
   a main body having a generally U-shape or C-shape when viewed from a top or bottom view, said main body including a lateral segment interconnecting an anterior segment and a posterior segment;
   a sleeve provided separately of said main body, said sleeve being configured and dimensioned to receive said anterior segment; and
   a pad provided separately of said main body, said pad comprising an engagement feature configured to engage with said posterior segment;
   wherein said main body is configured to be non-flexible relative to forces applied thereto by the heart; and
   wherein said pad is molded, said device further comprising a flap extending inferiorly of said pad, wherein said flap is not molded and is configured to be anchored to the epicardial surface by passing one or more fixators through said flap.

2. The device of claim 1, wherein said sleeve is configured to be anchored to the epicardial surface of the heart prior to receiving said anterior segment.

3. The device of claim 1, wherein said pad is configured to be anchored to the epicardial surface of the heart prior to engagement with said posterior segment.

4. The device of claim 1, wherein the valve is the mitral valve, the mitral valve lying in a plane between the left atrium and the left ventricle of the heart, the anatomy of the heart includes an aorta, a pulmonary trunk, a superior vena cava, a transverse sinus, and an atrioventricular groove;
wherein the anterior segment is configured and dimensioned to at least partially occupy the transverse sinus epicardially and end at a location short of overlying the right atrium of the heart; and
wherein the pad is configured and dimensioned to contact the heart on or below a plane in which the mitral valve is located, and below a position of the anterior segment.

5. The device of claim 1, wherein said main body maintains said U-shape or C-shape after completion of placement of said epicardial device on the heart.

6. The device of claim 1, wherein said engagement feature comprises a hook extending from a surface of said pad.

7. The device of claim 6, wherein said surface is opposite a contact surface of said pad, wherein said contact surface of said pad is configured to contact the epicardial surface of the heart when said pad is anchored to the epicardial surface.

8. The device of claim 1, further comprising a reinforcing member within said pad.

9. The device of claim 1, wherein a contact surface of said pad is configured to expand after anchoring said pad to target tissue, to increase force applied to the target tissue.

10. The device of claim 1, wherein said engagement feature comprises a receptacle formed in said pad and configured to receive at least a portion of said posterior segment.

11. The device of claim 10, further comprising a locator clip in said receptacle, said locator clip configured to capture said posterior segment so that a predefined length of said posterior segment is received in said receptacle.

12. The device of claim 1, wherein said flap comprises multiple flaps extending inferiorly of said pad.

13. The device of claim 1, wherein a contact surface of said pad has a roughness exceeding a roughness of a surface of said pad opposite said contact surface.

14. The device of claim 1, wherein said sleeve is a tubular structure having a flat surface extending along a length thereof, said flat surface configured to engage the heart at a bottom of a transverse sinus.

15. The device of claim 1, wherein said sleeve comprises a tubular structure and further comprises a sleeve pad within said tubular structure, said sleeve pad being placed to reside between a bottom surface of said sleeve and said anterior segment.

16. The device of claim 15, wherein said sleeve pad is a contoured paid having a receptacle formed therein, wherein said receptacle generally conforms to a shape of the anterior segment to be received therein.

17. The device of claim 1, wherein said sleeve is tubular and comprises a first surface configured to be oriented as a bottom surface when anchoring the sleeve to the epicardial surface of the heart, and a second surface opposite said first surface, wherein said second surface comprises at least one opening configured to permit a fixator to be passed therethrough to enable said fixator to be driven through the first surface to anchor the sleeve.

18. The device of claim 1, wherein said sleeve comprises a tubular structure, said device further comprising a flap extending radially or tangentially outwardly from said sleeve and also extending along a length of said sleeve.

19. The device of claim 1, wherein said main body is provided in multi-part segments, wherein said segments are configured to be assembled in the body of a patient to form said non-flexible main body.

20. The device of claim 19, wherein said segments are connectable via mechanical connectors.

21. The device of claim 19, wherein said segments are connectable via magnetic connectors.

22. An epicardial device for reducing or preventing regurgitation of blood through a tricuspid valve of a heart, said device comprising:
a main body adapted to apply force to an epicardial surface of the heart;
a member that applies counterforce to said force applied by said segment; and
an adjuster that is operable to change the force applied by said segment;
wherein said adjuster can be operated before or after anchoring of said device to the epicardial surface; and
wherein said main body comprises two segments comprising rods that extend through opposite end portions of said main body and are joined together by an actuator configured so that said segments are drivable in opposite directions to one another, to increase or decrease a distance between ends of said main body.

23. The epicardial device of claim 22, wherein said adjuster is manually operable.

24. The epicardial device of claim 22, wherein said adjuster is remotely operable.

25. The epicardial device of claim 22, wherein said main body is configured and dimensioned to surround greater than 50% of an annulus of the tricuspid valve.

26. The epicardial device of claim 22, wherein said actuator is motorized.

27. An epicardial device for placement on an epicardial surface of a heart in order to reshape an annulus of a valve of the heart, the epicardial device comprising:
a main body having a generally U-shape or C-shape when viewed from a top or bottom view, said main body including a lateral segment interconnecting an anterior segment and a posterior segment;
a sleeve provided separately of said main body, said sleeve being configured and dimensioned to receive said anterior segment; and
a pad provided separately of said main body, said pad comprising an engagement feature configured to engage with said posterior segment;
wherein said main body is configured to be non-flexible relative to forces applied thereto by the heart; and
wherein said engagement feature comprises a hook extending from a surface of said pad.

28. An epicardial device for reducing or preventing regurgitation of blood through a tricuspid valve of a heart, said device comprising:
a main body having a segment adapted to apply force to an epicardial surface of the heart;
a member that applies counterforce to said force applied by said segment; and
an adjuster that is operable to change the force applied by said segment;
wherein said adjuster can be operated before or after anchoring of said device to the epicardial surface;

wherein said segment comprises a rigid structural rib contained within a pad;
wherein said pad comprises a contact surface configured to apply said force to the epicardial surface;
wherein said adjuster comprises a channel having stops formed therein;
wherein a first set of said stops maintains said rib at a first predetermined distance from said contact surface; and
wherein a second set of said stops maintains said rib at a second predetermined distance from said contact surface, said second predetermined distance being unequal to said first predetermined distance.

29. The epicardial device of claim 28, wherein said device is operable to change a location of at least a portion of said rib from being held by said first set of stops to a location where said at least a portion of said rib is held by said second set of stops, by manually pushing against said rib, via application of pressure to said body at locations apposite said first set of stops, while applying counter-pressure to said contact surface at locations that are not apposite to said first set of stops.

\* \* \* \* \*